US012773446B2

(12) United States Patent
Yarar et al.

(10) Patent No.: US 12,773,446 B2
(45) Date of Patent: Oct. 27, 2026

(54) METHODS TO STIMULATE IMMUNE RESPONSES TO MUTANT RAS USING NUCLEATED CELLS

(71) Applicant: STEMCELL TECHNOLOGIES CANADA INC., Vancouver (CA)

(72) Inventors: Defne Yarar, Watertown, MA (US); Howard Bernstein, Cambridge, MA (US); Katherine Seidl, Watertown, MA (US); Amritha Ramakrishnan, Watertown, MA (US); Carolyne Kelly Smith, Waltham, MA (US); Anita Venkitaraman, Watertown, MA (US); Scott Loughhead, Watertown, MA (US)

(73) Assignee: STEMCELL TECHNOLOGIES CANADA INC., Vancouver (CA)

( * ) Notice: Subject to any disclaimer, the term of this patent is extended or adjusted under 35 U.S.C. 154(b) by 554 days.

(21) Appl. No.: 18/007,287

(22) PCT Filed: Jul. 28, 2021

(86) PCT No.: PCT/US2021/043567
§ 371 (c)(1),
(2) Date: Jan. 27, 2023

(87) PCT Pub. No.: WO2022/026620
PCT Pub. Date: Feb. 3, 2022

(65) Prior Publication Data

US 2025/0255961 A1 Aug. 14, 2025

Related U.S. Application Data

(60) Provisional application No. 63/058,441, filed on Jul. 29, 2020.

(51) Int. Cl.
*C12N 15/85* (2006.01)
*A61K 39/00* (2006.01)
*A61K 40/42* (2025.01)
*C12N 5/078* (2010.01)
*C12N 9/14* (2006.01)

(52) U.S. Cl.
CPC .. *A61K 39/001164* (2018.08); *A61K 40/4253* (2025.01); *C12N 5/0634* (2013.01); *C12N 9/14* (2013.01); *A61K 2039/6006* (2013.01)

(58) Field of Classification Search
None
See application file for complete search history.

(56) References Cited

FOREIGN PATENT DOCUMENTS

| | | | | |
|---|---|---|---|---|
| WO | WO-2013149167 A1 * | 10/2013 | ............. A61P 31/20 |
| WO | 2015123532 A1 | 8/2015 | |
| WO | 2015169804 A1 | 11/2015 | |
| WO | 2016070136 A1 | 5/2016 | |
| WO | 2019178006 A1 | 9/2019 | |
| WO | 2020/072833 | 4/2020 | |

OTHER PUBLICATIONS

Guang Tan et al., Induction of CTLs by DCs pulsed with K-ras mutant peptide on the surface of nanoparticles in the treatment of pancreatic cancer, Oncology Reports. 2011, vol. 26, pp. 215-221.
Boris Kubuschok et al., Use of Spontaneous Epstein-Barr Virus-Lymphoblastoid Cell Lines Genetically Modified to Express Tumor Antigen as Cancer Vaccines: Mutated p21 ras Oncogene in Pancreatic Carcinoma as a Model, Human Gene Therapy, 2002, vol. 13, No. 7, pp. 815-827.
Uprety Dipesh et al, "KRAS: From undruggable to a druggable Cancer Target", Jul. 15, 2020 (Jul. 15, 2020, vol. {0} 89, XP086252172.
Antoun Toubaji et al, "Pilot study of mutant ras peptide-based vaccine as an adjuvant treatment in pancreatic and colorectal cancers", Cancer Immunology, Immunotherapy, Springer, Berlin, DE,vol. {0} 57, No. {0} 9, Feb. 23, 2008 (Feb. 23, 2008), p. 1413-1420, XP019624400.
Gregory Lee Szeto et al, "Microfluidic squeezing for intracellular antigen loading in polyclonal B-cells as cellular vaccines", Scientific Reports,vol. {0} 5, No. {0} 1, May 22, 2015 (May 22, 2015), XP055565958.
Armon Sharei et al, "Cell Squeezing as a Robust, Microfluidic Intracellular Delivery Platform", Journal of Visualized Experiments,No. {0} 81, Nov. 7, 2013 (Nov. 7, 2013), p. 1-7, XP055543723.
Myint Melissa et al, "Vector-Free Engineering of Antigen Presenting Cells for Adoptive Immunotherapies for the Treatment of Cancer", The Journal of Immunology; Annual Meeting of the American-Association-Of-Immunologists (AAI); Washington, DC, USA; May 12-16, 2017, Williams & Wilkins Co, US,vol. {0} 198, No. {0} 1, Suppl. S, May 1, 2017 (May 1, 2017), p. 73.18, XP009530828.
Blagovic Katarina et al, "Engineering Antigen Presenting Cell (APC) Cancer Therapies Using the SQZ Platform", Molecular Therapy; 22nd Annual Meeting of the American-Society-Of-Gene-And-Cell-Therapy (ASGCT); Washington, DC, USA; Apr. 29-May 2, 2019, Elsevier Inc, US,vol. {0} 27, No. {0} 4, Suppl. 1, Apr. 22, 2019 (Apr. 22, 2019), p. 386, XP009530827.
Yarar D et al, "Peripheral blood mononuclear cells engineered via microfluidic Cell Squeeze technology to generate APCs that drive mutant-KRas-specific CD8+ T cell responses", vol. {0} 81, No. {0} 13 Suppl, Issn: 1538-7445; Jul. 2021 (Jul. 2021), Cancer Research, American Association for Cancer Research, US, Retrieved from the Internet: URL:https://cancerres.aacrjournals.org/content/81/13_Supplement/1524.

(Continued)

*Primary Examiner* — Celine X Qian
(74) *Attorney, Agent, or Firm* — Smart & Biggar LP; Micheline Gravelle

(57) ABSTRACT

The present application provides nucleated cells comprising a mutated Ras antigen (such as a mutated K-Ras antigen), methods of manufacturing such nucleated cells comprising the mutated Ras antigen, and methods of using such modified nucleated cells (e.g., immune cells) for stimulating an immune response, treating, and/or vaccinating an individual with a cancer associated with Ras mutation.

18 Claims, 11 Drawing Sheets

Specification includes a Sequence Listing.

(56) References Cited

OTHER PUBLICATIONS

Ozay E et al, "Microfluidics cell squeezing enables potent cellular vaccines in murine models through direct cytosolic loading and direct cd8 t cell priming", vol. {0} 8, No. {0} Suppl 3, ISSN:2051-1426, Nov. 1, 2020 (Nov. 1, 2020), p. A102, Journal for Immunotherapy of Cancer, Biomed Central, London, GB, Retrieved from the Internet: URL:https://jitc.bmj.com/content/jitc/8/Suppl_3/A102.2.full.pdf, XP009530830.
Wan Yuhua et al, "Recombinant KRAS G12D Protein Vaccines Elicit Significant Anti-Tumor Effects in Mouse CT26 Tumor Models", Frontiers in Oncology,vol. {0} 10, Aug. 12, 2020 (Aug. 12, 2020), p. 1-14, XP055854515.
David P. Carbone et al., "Immunization with Mutant p53- and K-ras-Derived Peptides in Cancer Patients: Immune Response and Clinical Outcome", Journal of Clinical Oncology, 2005, vol. 23, No. 22, pp. 5099-5107.

* cited by examiner

FIG. 10
HLA-A11*+ Donor -spin only-1-16&2-29
SFU / 1 x $10^6$ cells
15000
10000
5000
Vehicle SQZ
E7.6 SLP SQZ
FF G12D$^{1-16}$
Endo G12D$^{1-16}$
SQZ G12D$^{1-16}$
FF G12D$^{2-29}$
Endo G12D$^{2-29}$
SQZ G12D$^{2-29}$
WT$^{7-16}$ (Spike)
G12D$^{7-16}$ (Spike)

METHODS TO STIMULATE IMMUNE RESPONSES TO MUTANT RAS USING NUCLEATED CELLS

CROSS-REFERENCE TO RELATED APPLICATIONS

This application claims priority to U.S. Provisional Application Nos. 63/058,441 filed on Jul. 29, 2021, the contents of which are incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750322002840SEQLIST. TXT, date recorded: Jul. 28, 2021, size: 5 KB).

FIELD OF THE INVENTION

The present disclosure relates generally to nucleated cells comprising a mutated Ras antigen, methods of manufacturing such modified nucleated cells, and methods of using such modified nucleated cells for treating a cancer associated with mutated Ras protein.

BACKGROUND OF THE INVENTION

Ras is one of the most well-known proto-oncogenes. Its gain-of-function mutations occur in approximately 30% of all human cancers. As the most frequently mutated Ras isoform, K-Ras has been intensively studied in the past years. Despite its well-recognized importance in cancer malignancy, continuous efforts in the past three decades have failed to develop therapies for K-Ras mutant cancer, and to date, no therapy for such malignancy has been approved. K-Ras has thus long been considered undruggable.

Members of the Ras superfamily are divided into families and subfamilies based on their structure, sequence and function. K-Ras belongs to a group of small guanosine triphosphate (GTP) binding proteins known as the Ras superfamily or RAS-like GTPases. In humans, three RAS genes encode highly homologous RAS proteins, H-Ras, N-Ras and K-Ras. K-Ras is one of the front-line sensors that initiate the activation of an array of signaling molecules, allowing the transmission of transducing signals from the cell surface to the nucleus, and affecting a range of essential cellular processes such as cell differentiation, growth, chemotaxis and apoptosis. The K-Ras isoform is the isoform most frequently mutated, and constitutes 86% of RAS mutations. There are two known isoform splice variants within the K-Ras isoform: K-Ras4A and K-Ras4B. The K-Ras4B splice variant is the dominant isoform with mutations in human cancers, and it is present in approximately 90% of pancreatic cancers, 30% to 40% of colon cancers, and 15% to 20% of lung cancers, mostly non-small-cell lung cancer (NSCLC) (Liu, P. et al., *Acta Pharmaceutica Sinica B,* 2019, 9 (5): 871-879). It is also present in biliary tract malignancies, endometrial cancer, cervical cancer, bladder cancer, liver cancer, myeloid leukemia and breast cancer. Despite its prevalence, decades long efforts in the discovery of RAS targeted therapies have repeatedly failed to produce clinically approved drugs.

Immunotherapy can be divided into two main types of interventions, either passive or active. Passive protocols include administration of pre-activated and/or engineered cells (e.g., CAR T cells), disease-specific therapeutic antibodies, and/or cytokines. Active immunotherapy strategies are directed at stimulating immune system effector functions in vivo. Several current active protocols include vaccination strategies with disease-associated peptides, lysates, or allogeneic whole cells, infusion of autologous dendritic cell (DCs) as vehicles for tumor antigen delivery, and infusion of immune checkpoint modulators. See Papaioannou, Nikos E., et al. *Annals of translational medicine* 4.14 (2016). Adoptive immunotherapy can be employed to modulate the immune response, enhance antitumor activity, and achieve the goal of treating or preventing cancers associated with Ras mutations.

$CD8^+$ cytotoxic T lymphocytes (CTL) and $CD4^+$ helper T (Th) cells stimulated by disease-associated antigens have the potential to target and destroy diseased cells; however, current methods for inducing endogenous T cell responses have faced challenges. The methods described herein are used to generate nucleated cells comprising mutated Ras antigens efficiently in a high throughput manner, which can be utilized in inducing a robust T cell response to mutated Ras antigens.

All references cited herein, including patent applications and publications, are incorporated by reference in their entirety. The patent publications WO 2016070136, US 20180142198, WO 2017/008063, US20180201889, WO 2019/178005, and WO 2019178006 and PCT/US2020/020194 are hereby expressly incorporated by reference in their entirety.

BRIEF SUMMARY OF THE INVENTION

In some aspects, the invention provides methods for stimulating an immune response to a mutated Ras protein in an individual, the method comprising administering an effective amount of a composition comprising nucleated cells to an individual, wherein the nucleated cells comprise a mutated Ras antigen; wherein the mutated Ras antigen is delivered to the nucleated cell intracellularly. In some aspects, the invention provides methods for reducing tumor growth in an individual, the method comprising administering an effective amount of a composition comprising nucleated cells to an individual, wherein the nucleated cells comprise a mutated Ras antigen; wherein the mutated Ras antigen is delivered to the nucleated cell intracellularly. In some aspects, the invention provides methods for vaccinating an individual in need thereof, the method comprising administering an effective amount of a composition comprising nucleated cells to an individual, wherein the nucleated cells comprise a mutated Ras antigen; wherein the mutated Ras antigen is delivered to the nucleated cell intracellularly. In some embodiments, the individual has cancer. In some aspects, the invention provides methods for treating cancer in an individual, the method comprising administering an effective amount of a composition comprising nucleated cells to an individual, wherein the nucleated cells comprise a mutated Ras antigen; wherein the mutated Ras antigen is delivered to the nucleated cell intracellularly. In some embodiments, the cancer is a pancreatic cancer, a colon cancer, a small intestine cancer, a biliary tract cancer, an endometrial cancer, a lung cancer, a skin cancer, an ovarian cancer, a stomach cancer, an esophageal cancer, a cervical cancer or a urinary tract cancer.

In some embodiments of the methods described herein, the mutated Ras antigen is a mutated K-Ras antigen, a mutated H-Ras antigen, or a mutated N-Ras antigen. In some embodiments, the mutated Ras antigen is a mutated K-Ras4A antigen or a mutated K-Ras4B antigen. In some embodiments, the mutated Ras antigen is a single polypeptide that elicits a response against the same and or different mutated Ras antigens. In some embodiments, the mutated Ras antigen is a pool of multiple polypeptides that elicit a response against the same and or different mutated Ras antigens. In some embodiments, the mutated Ras antigen is a polypeptide comprising one or more antigenic mutated Ras epitopes and one or more heterologous peptide sequences. In some embodiments, the mutated Ras antigen complexes with other antigens or with an adjuvant. In some embodiments, the mutated Ras antigen comprises a G12D mutation, a G12V mutation, a G12C mutation or a G13D mutation. In some embodiments, the mutated Ras antigen comprises an amino acid sequence with at least 90% similarity to any one of SEQ ID NOs: 9-15. In some embodiments, the mutated Ras antigen comprises an amino acid sequence of SEQ ID NOs: 9-15. In some embodiments, the mutated Ras antigen is one or more of a $G12D^{1-16}$, a $G12D^{2-19}$, a $G12D^{2-22}$, a $G12D^{2-29}$, a $G12V^{1-16}$, a $G12V^{2-19}$, a $G12V^{3-17}$, or a $G12V^{3-42}$ antigen. In some embodiments, the mutated Ras antigen comprises an amino acid sequence with at least 90% similarity to any one of SEQ ID NOs: 1-8. In some embodiments, the mutated Ras antigen comprises an amino acid sequence of SEQ ID NOs: 1-8. In some embodiments, the mutated Ras antigen is a polypeptide comprising one or more antigenic mutated Ras epitopes that is flanked on the N-terminus and/or the C-terminus by one or more heterologous peptide sequences. In some embodiments, the mutated Ras antigen is capable of being processed into an MHC class I-restricted peptide. In some embodiments, the mutated Ras antigen is capable of being processed into an MHC class II-restricted peptide.

In some embodiments of the methods described herein the composition further comprises an adjuvant. In some embodiments, the composition is administered in conjunction with an adjuvant. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist.

In some embodiments of the methods described herein the nucleated cells comprising the mutated Ras antigen are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mutated Ras antigen to pass through to form a perturbed input nucleated cells; and b) incubating the perturbed input nucleated cells with the mutated Ras antigen for a sufficient time to allow the mutated Ras antigen to enter the perturbed input nucleated cells; thereby generating nucleated cells comprising the mutated Ras antigen. In some embodiments, the nucleated cells comprising the mutated Ras antigen are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for a nucleic acid encoding the mutated Ras antigen to pass through to form a perturbed input nucleated cells; and b) incubating the perturbed input nucleated cells with the nucleic acid encoding the mutated Ras antigen for a sufficient time to allow the nucleic acid encoding the mutated Ras antigen to enter the perturbed input nucleated cells; wherein the nucleic acid encoding the mutated Ras is expressed thereby generating nucleated cells comprising the mutated Ras antigen. In some embodiments, the width of the constriction is about 10% to about 99% of the mean diameter of the input nucleated cells. In some embodiments, the width of the constriction is about 3.5 μm to about 4.2 μm or about 3.5 μm to about 4.8 μm or about 3.5 μm to about 6 μm or about 4.2 μm to about 4.8 μm or about 4.2 μm to about 6 μm. In some embodiments, the width of the constriction is about 3.5 μm. In some embodiments, the width of the constriction is about 4.5 μm. In some embodiments, the cell suspension comprising the plurality of input nucleated cells are passed through multiple constrictions wherein the multiple constrictions are arranged in series and/or in parallel.

In some embodiments of the methods of the invention, the nucleated cells are immune cells. In some embodiments, the nucleated cells are human cells with a haplotype of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16. In some embodiments, the nucleated cells are a plurality of peripheral blood mononuclear cells (PBMCs). In some embodiments, the plurality of PBMCs comprise two or more of T cell, B cell, NK cell, monocytes, dendritic cells or NK-T cells.

36. In some embodiments, the nucleated cells are one or more of T cells, B cells, NK cells, monocytes, dendritic cells and/or NK-T cells. In some embodiments, the nucleated cells are conditioned with an adjuvant to form conditioned cells. In some embodiments, the nucleated cells are incubated with the adjuvant for about 1 hour to about 24 hours, about 2 hours to about 10 hours, about 3 hours to about 6 hours, or about 4 hours for the cells to condition. In some embodiments, the nucleated cells are conditioned before or after introducing the mutated Ras antigen into the nucleated cells. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist. In some embodiments, the adjuvant is a CpG oligodeoxynucleotide (ODN). In some embodiments, the adjuvant is CpG 7909. In some embodiments, the conditioned cells are a conditioned plurality of PBMCs.

In some embodiments of the methods described herein, the plurality of PBMCs are modified to increase expression of one or more of co-stimulatory molecules. In some embodiments, the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112. In some embodiments, the plurality of PBMCs are modified to increase expression of one or more cytokines. In some embodiments, the cytokine is IL-15, IL-12, IL-2, IFN-α, or IL-21. In some embodiments, one or more co-stimulatory molecules is upregulated in the B cells of the conditioned plurality of PBMCs compared to the B cells in the plurality of nonconditioned PBMCs, wherein the co-stimulatory molecule is CD80 and/or CD86. In some embodiments, the plurality of PBMCs have increased expression of one or more of IFN-γ, IL-6, MCP-1, MIP-1β, IP-10, or TNF-α compared to a plurality of unconditioned PBMCs. In some embodiments, the expression of one or more of IFN-γ, IL-6, MCP-1, MIP-1β, IP-10, or TNF-α is increased by more than about 1.2-fold, 1.5-fold, 1.8-fold, 2-fold, 3-fold, 4-fold, 5-fold, 8-fold, or more than 10-fold compared to the plurality of unconditioned PBMCs.

In some embodiments of the methods described herein, the composition comprising nucleated cells is administered a plurality of times. In some embodiments, the composition is administered intravenously. In some embodiments, the individual is a human.

In some embodiments of the methods described herein, the composition is administered prior to, concurrently with, or following administration of another therapy. In some embodiments, another therapy is a chemotherapy, a radiation therapy, an antibody, a cytokine, an immune checkpoint inhibitor, or a bispecific polypeptide used in immune-oncology therapy.

In some aspects, the invention provides compositions comprising conditioned nucleated cells, wherein the nucleated cells comprise a mutated Ras antigen; wherein the mutated Ras antigen antigen is delivered to the nucleated cell intracellularly. In some embodiments, the nucleated cells are conditioned with an adjuvant to form conditioned cells. In some aspects, the invention provides compositions comprising conditioned nucleated cells comprising a mutated Ras antigen, wherein the conditioned nucleated cells comprising the mutated Ras antigen are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mutated Ras antigen to pass through to form a perturbed input nucleated cells; b) incubating the perturbed input nucleated cells with the mutated Ras antigen for a sufficient time to allow the mutated Ras antigen to enter the perturbed input nucleated cells; thereby generating nucleated cells comprising the mutated Ras antigen; and c) incubating the nucleated cells with the adjuvant for the nucleated cells to condition. In some aspects, the invention provides compositions comprising conditioned nucleated cells comprising a mutated Ras antigen, wherein the conditioned nucleated cells comprising the mutated Ras antigen are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for a nucleic acid encoding the mutated Ras antigen to pass through to form a perturbed input nucleated cells; b) incubating the perturbed input nucleated cells with the nucleic acid encoding the mutated Ras antigen for a sufficient time to allow the nucleic acid encoding the mutated Ras antigen to enter the perturbed input nucleated cells; thereby generating nucleated cells comprising the nucleic acid encoding mutated Ras antigen, wherein the nucleic acid encoding the mutated H-Ras antigen is expressed thereby generating a nucleated cell comprising a mutated H-Ras antigen; and c) incubating the nucleated cells with the adjuvant for the nucleated cells to condition. In some embodiments, the nucleated cells are incubated with the adjuvant for about 1 hour to about 24 hours, about 2 hours to about 10 hours, about 3 hours to about 6 hours, or about 4 hours for the cells to condition. In some embodiments, the nucleated cells are conditioned before or after introducing the mutated Ras antigen or the nucleic acid encoding the mutated Ras antigen into the nucleated cells. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist. In some embodiments, the adjuvant is a CpG oligodeoxynucleotide (ODN). In some embodiments, the adjuvant is CpG 7909.

In some embodiments of the compositions described herein, the nucleated cells are immune cells. In some embodiments, the nucleated cells are human cells with a haplotype of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16. In some embodiments, the conditioned cells are a conditioned plurality of PBMCs. In some embodiments, the plurality of PBMCs comprise two or more of T cell, B cell, NK cell, monocytes, dendritic cells or NK-T cells. In some embodiments, the nucleated cells are one or more of T cells, B cells, NK cells, monocytes, dendritic cells and/or NK-T cells. In some embodiments, the plurality of PBMCs are modified to increase expression of one or more of co-stimulatory molecules. In some embodiments, the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112. In some embodiments, the plurality of PBMCs are modified to increase expression of one or more cytokines. In some embodiments, the cytokine is IL-15, IL-12, IL-2, IFN-α, or IL-21. In some embodiments, one or more co-stimulatory molecules is upregulated in the B cells of the conditioned plurality of PBMCs compared to the B cells in the plurality of nonconditioned PBMCs, wherein the co-stimulatory molecule is CD80 and/or CD86. In some embodiments, the conditioned plurality of PBMCs have increased expression of one or more of IFN-γ, IL-6, MCP-1, MIP-1β, IP-10, or TNF-α compared to a unconditioned plurality of PBMCs. In some embodiments, the expression of one or more of IFN-γ, IL-6, MCP-1, MIP-1β, IP-10, or TNF-α is increased by more than about 1.2-fold, 1.5-fold, 1.8-fold, 2-fold, 3-fold, 4-fold, 5-fold, 8-fold, or more than 10-fold compared to the plurality of unconditioned PBMCs.

In some aspects, the invention provides compositions comprising nucleated cells, wherein the nucleated cells comprise a mutated Ras antigen; wherein the mutated Ras antigen is delivered to the nucleated cell intracellularly. In some aspects, the invention provides compositions comprising nucleated cells comprising a mutated Ras antigen, wherein the nucleated cells comprising the mutated Ras antigen are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mutated Ras antigen to pass through to form perturbed input nucleated cells; and b) incubating the perturbed input nucleated cells with the mutated Ras antigen for a sufficient time to allow the mutated Ras antigen to enter the perturbed input nucleated cells; thereby generating nucleated cells comprising the mutated Ras antigen. In some aspects, the invention provides compositions comprising nucleated cells comprising a mutated Ras antigen, wherein the nucleated cells comprising the mutated Ras antigen are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for a nucleic acid encoding the mutated Ras antigen to pass through to form perturbed input nucleated cells; and b) incubating the perturbed input nucleated cells with the nucleic acid encoding the mutated Ras antigen for a sufficient time to allow the nucleic acid encoding the mutated Ras antigen to enter the perturbed input nucleated cells, wherein the nucleic acid expressed the mutated Ras antigen; thereby generating nucleated cells comprising the mutated Ras antigen. In some embodiments, the width of the constriction is about 10% to about 99% of the mean diameter of the input nucleated cells. In some embodiments, the width of the constriction is about 4.2 μm to about 6 μm, about 4.2 μm to about 4.8 μm, or about 3.5 μm to about 6 μm or about 4.2 μm to about 4.8 μm or about 4.2 μm to about 6 μm. In some embodiments, the width of the constriction is about 3.5 μm. In some embodiments, the width of the constriction is about 4.5 μm. In some embodiments, the cell suspension comprising the input nucleated cells are passed through multiple constrictions wherein the multiple constrictions are arranged in series and/or in parallel.

In some embodiments of the compositions described herein, the nucleated cells are immune cells. In some embodiments, the nucleated cells are human cells with a haplotype of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16. In some embodiments, the nucleated cells are a plurality of peripheral blood mononuclear cells (PBMCs). In some embodiments, the plurality of PBMCs comprise two or more of T cell, B cell, NK cell, monocytes, dendritic cells or NK-T cells. In some embodiments, the nucleated cells are one or more of T cells, B cells, NK cells, monocytes, dendritic cells and/or NK-T cells.

In some embodiments of the compositions described herein, the mutated Ras antigen is a mutated K-Ras antigen, a mutated H-Ras antigen, or a mutated N-Ras antigen. In some embodiments, the mutated Ras antigen is a mutated K-Ras4A antigen or a mutated K-Ras4B antigen. In some embodiments, the mutated Ras antigen is a single polypeptide that elicits a response against the same and or different mutated Ras antigens. In some embodiments, the mutated Ras antigen is a pool of multiple polypeptides that elicit a response against the same and or different mutated Ras antigens. In some embodiments, the mutated Ras antigen is a polypeptide comprising one or more antigenic mutated Ras epitopes and one or more heterologous peptide sequences. In some embodiments, the mutated Ras antigen complexes with other antigens or with an adjuvant. In some embodiments, the mutated Ras antigen comprises a G12D mutation, a G12V mutation, a G12C mutation or a G13D mutation. In some embodiments, the mutated Ras antigen comprises an amino acid sequence with at least 90% similarity to any one of SEQ ID NOs: 9-15. In some embodiments, the mutated Ras antigen comprises an amino acid sequence of SEQ ID NOs: 9-15. In some embodiments, the mutated Ras antigen is one or more of a $G12D^{1-16}$, a $G12D^{2-19}$, a $G12D^{2-22}$, a $G12D^{2-29}$ antigen, a $G12V^{1-16}$, a $G12V^{2-19}$, a $G12V^{3-17}$, or a $G12V^{3-42}$ antigen. In some embodiments, the mutated Ras antigen comprises an amino acid sequence with at least 90% similarity to any one of SEQ ID NOs: 1-8. In some embodiments, the mutated Ras antigen comprises an amino acid sequence of SEQ ID NOs: 1-8. In some embodiments, the mutated Ras antigen is a polypeptide comprising one or more antigenic mutated Ras epitopes that is flanked on the N-terminus and/or the C-terminus by one or more heterologous peptide sequences. In some embodiments, the mutated Ras antigen is capable of being processed into an MHC class I-restricted peptide. In some embodiments, the mutated Ras antigen is capable of being processed into an MHC class II-restricted peptide.

In some embodiments of the compositions described herein the composition further comprises an adjuvant. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist.

In some aspects, the invention provides kits for use in any of the methods described herein. In some aspects, the invention provides kits comprising any of the compositions described herein. In some embodiments, the kit further comprises one or more of buffers, diluents, filters, needles, syringes, or package inserts with instructions for administering the composition to an individual to stimulate an immune response to a mutated K-Rad, reduce tumor growth and/or treat cancer.

In some aspects, the invention provides methods for producing a composition of nucleated cells comprising a mutated Ras antigen; the method comprising introducing the mutated Ras antigen to the nucleated cell intracellularly. In some embodiments, introducing the mutated Ras antigen to the nucleate cell intracellularly comprises a) passing a cell suspension comprising input nucleated cells through a cell-deforming constriction, wherein a diameter of the constriction is a function of a diameter of the input nucleated cells in the suspension, thereby causing perturbations of the input nucleate cells large enough for the mutated Ras antigen to pass through to form a perturbed input nucleated cells; and b) incubating the perturbed input nucleated cells with the mutated Ras antigen for a sufficient time to allow the mutated Ras antigen to enter the perturbed input nucleated cells; thereby generating nucleated cells comprising the mutated Ras antigen. In some embodiments, introducing the mutated Ras antigen to the nucleated cell intracellularly comprises a) passing a cell suspension comprising input nucleated cells through a cell-deforming constriction, wherein a diameter of the constriction is a function of a diameter of the input nucleated cells in the suspension, thereby causing perturbations of the input nucleated cells large enough for a nucleic acid encoding the mutated Ras antigen to pass through to form a perturbed input nucleated cells; and b) incubating the perturbed input nucleated cells with the nucleic acid encoding the mutated Ras antigen for a sufficient time to allow the nucleic acid encoding the mutated Ras antigen to enter the perturbed input nucleated cells, wherein the nucleic acid expressed the mutated Ras antigen; thereby generating nucleated cells comprising the mutated Ras antigen. In some embodiments, the width of the constriction is about 10% to about 99% of the mean diameter of the input nucleated cells. In some embodiments, the width of the constriction is about 3.5 μm to about 4.2 μm or about 3.5 μm to about 4.8 μm or about 3.5 μm to about 6 μm or about 4.2 μm to about 4.8 μm or about 4.2 μm to about 6 μm. In some embodiments, the width of the constriction is about 3.5 μm. In some embodiments, the width of the constriction is about 4.5 μm. In some embodiments, the cell suspension comprising the plurality of input nucleated cells are passed through multiple constrictions wherein the multiple constrictions are arranged in series and/or in parallel.

In some embodiments of the methods of producing compositions of nucleated cell comprising a mutated Ras antigen, the method further comprising conditioning the nucleated cells with an adjuvant to form conditioned cells. In some embodiments, the nucleated cells are incubated with the adjuvant for about 1 hour to about 24 hours, about 2 hours to about 10 hours, about 3 hours to about 6 hours, or about 4 hours for the cells to condition. In some embodiments, the nucleated cells are conditioned before or after introducing the mutated Ras antigen into the nucleated cells.

DETAILED DESCRIPTION OF THE INVENTION

Figure 1:
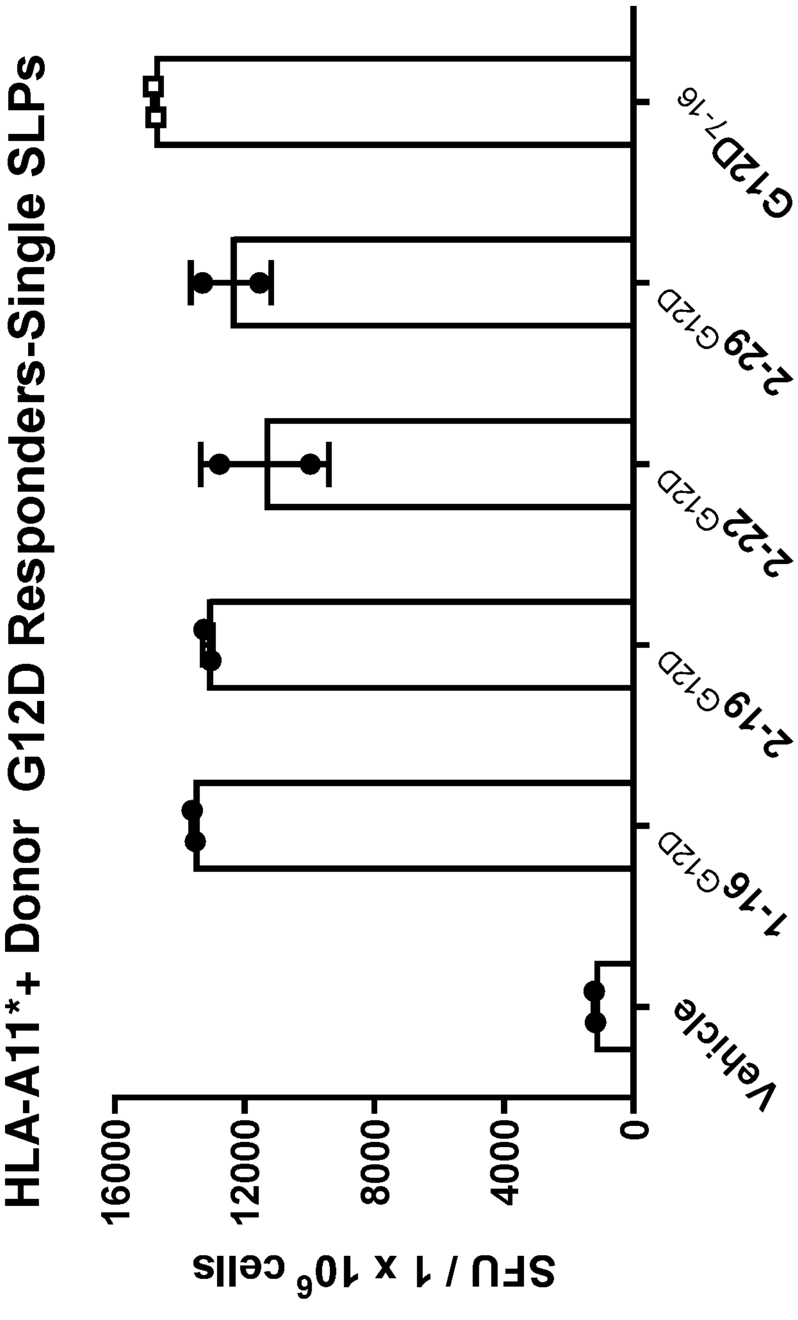
FIG. 1 is a graph showing increased amount of IFN-γ expressing K-Ras-G12D responder T cells upon co-culture with PBMCs loaded with mutated K-Ras antigens G12D$^{1-16}$, G12D$^{2-19}$, G12D$^{2-22}$, and G12D$^{2-29}$.

In some aspects, the present invention provides methods for treating or preventing a cancer associated with a Ras mutation, and/or stimulating an immune response in an individual with a cancer associated with a Ras mutation, comprising administering to the individual a composition comprising nucleated cells (e.g. PBMCs) comprising a mutated Ras antigen. In some aspects, the present invention provides methods for treating a cancer associated with a Ras mutation, and/or stimulating an immune response in an individual with a cancer associated with a Ras mutation, the method comprising administering to the individual an effective amount of a composition comprising nucleated cells comprising a mutated Ras antigen delivered intracellularly; wherein the nucleated cells are prepared by first passing a cell suspension comprising an input cell through a cell-deforming constriction, wherein a diameter of the constriction is a function of a diameter of the input nucleated cells in the suspension, thereby causing perturbations of the input nucleated cells large enough for the mutated Ras antigen to pass through to form perturbed input nucleated cells; and then incubating the perturbed input nucleated cells with the mutated Ras antigen for a sufficient time to allow the mutated Ras antigen to enter the perturbed input cell; thereby generating the modified nucleated cells comprising the mutated Ras antigen. Certain aspects of the present disclosure relate to methods for generating a composition comprising nucleated cells comprising a mutated Ras antigen delivered intracellularly, wherein a nucleated cell is passed through a constriction, wherein the constriction deforms the cell thereby causing a perturbation of the cell such that a mutated Ras antigen enters the immune cell to be modified.

In some aspects, the present invention provides methods for treating or preventing a cancer associated with a Ras mutation, and/or modulating the immune response in an individual with a cancer associated with a Ras mutation comprising administering to the individual a composition comprising modified immune cells, wherein the modified immune cells comprise intracellularly a mutated Ras antigen. In some aspects, the present invention provides methods for treating or preventing a cancer associated with a Ras mutation, and/or modulating the immune response in an individual with a cancer associated with a Ras mutation, the method comprising administering to the individual an effective amount of a composition comprising modified nucleated cells, wherein the modified immune cells comprise intracellularly a mutated Ras antigen, wherein the modified nucleated cells are prepared by first passing a cell suspension comprising an input cell through a cell-deforming constriction, wherein a diameter of the constriction is a function of a diameter of the input cell in the suspension, thereby causing perturbations of the input cell large enough for the antigen to pass through to form a perturbed input cell; and then incubating the perturbed input cell with the mutated Ras antigen for a sufficient time to allow the mutated Ras antigen to enter the perturbed input cell; thereby generating the modified nucleated cells. Certain aspects of the present disclosure relate to methods for generating a composition comprising modified nucleated cells, wherein the nucleated cell is passed through a constriction, wherein the constriction deforms the cell thereby causing a perturbation of the cell such that a mutated Ras antigen enters the nucleated cell to be modified. In some further embodiments, the method for treating a cancer associated with a Ras mutation, and/or stimulating the immune response to mutated Ras protein in an individual with a cancer associated with a Ras mutation further comprises administering an adjuvant to the individual.

General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4th ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); *PCR 2: A Practical Approach* (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6th ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty, ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 2011).

Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

As used herein, the singular form "a", "an", and "the" includes plural references unless indicated otherwise.

It is understood that aspects and embodiments of the invention described herein include "comprising," "consisting," and "consisting essentially of" aspects and embodiments.

The term "about" as used herein refers to the usual error range for the respective value readily known to the skilled person in this technical field. Reference to "about" a value or parameter herein includes (and describes) embodiments that are directed to that value or parameter per se.

As used herein, "treatment" is an approach for obtaining beneficial or desired clinical results. "Treatment" as used herein, covers any administration or application of a therapeutic for disease in a mammal, including a human. For purposes of this invention, beneficial or desired clinical results include, but are not limited to, any one or more of: alleviation of one or more symptoms, diminishment of extent of disease, preventing or delaying spread (e.g., metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods of the invention contemplate any one or more of these aspects of treatment.

As used herein, the term "prophylactic treatment" refers to treatment, wherein an individual is known or suspected to have or be at risk for having a disorder but has displayed no symptoms or minimal symptoms of the disorder. An individual undergoing prophylactic treatment may be treated prior to onset of symptoms. In some embodiments, an individual may be treated if they have a precancerous lesion, particularly a precancerous lesion with a Ras mutation.

As used herein, by "combination therapy" is meant that a first agent be administered in conjunction with another agent. "In conjunction with" refers to administration of one treatment modality in addition to another treatment modality, such as administration of a composition of nucleated cells as described herein in addition to administration of an immunoconjugate as described herein to the same individual. As such, "in conjunction with" refers to administration of one treatment modality before, during, or after delivery of the other treatment modality to the individual.

The T term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

In the context of cancer, the term "treating" includes any or all of killing cancer cells, inhibiting growth of cancer cells, inhibiting replication of cancer cells, lessening of overall tumor burden and ameliorating one or more symptoms associated with the disease.

The term "pore" as used herein refers to an opening, including without limitation, a hole, tear, cavity, aperture, break, gap, or perforation within a material. In some examples, (where indicated) the term refers to a pore within a surface of the present disclosure. In other examples, (where indicated) a pore can refer to a pore in a cell membrane.

The term "membrane" as used herein refers to a selective barrier or sheet containing pores. The term includes a pliable sheetlike structure that acts as a boundary or lining. In some examples, the term refers to a surface or filter containing pores. This term is distinct from the term "cell membrane".

The term "filter" as used herein refers to a porous article that allows selective passage through the pores. In some examples the term refers to a surface or membrane containing pores.

The term "exogenous" when used in reference to an agent, such as an antigen or an adjuvant, with relation to a cell refers to an agent outside of the cell or an agent delivered into the cell from outside the cell. The cell may or may not have the agent already present, and may or may not produce the agent after the exogenous agent has been delivered.

The term "heterogeneous" as used herein refers to something which is mixed or not uniform in structure or composition. In some examples the term refers to pores having varied sizes, shapes or distributions within a given surface.

The term "homogeneous" as used herein refers to something which is consistent or uniform in structure or composition throughout. In some examples, the term refers to pores having consistent sizes, shapes, or distribution within a given surface.

The term "homologous" as used herein refers to a molecule which is derived from the same organism. In some examples, the term refers to a nucleic acid or protein which is normally found or expressed within the given organism.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

The term "heterologous" as it relates to amino acid sequences such as peptide sequences and polypeptide sequences, denotes sequences that are not normally joined together, and/or are not normally associated with a particular cell. Thus, a "heterologous" region of a peptide sequence is a segment of amino acids within or attached to another amino acid molecule that is not found in association with the other molecule in nature. For example, a heterologous region of a peptide construct could include the amino acid sequence of the peptide flanked by sequences not found in association with the amino acid sequence of the peptide in nature. Another example of a heterologous peptide sequence is a construct where the peptide sequence itself is not found in nature (e.g., synthetic sequences having amino acids different as coded from the native gene). Similarly, a cell transformed with a vector that expresses an amino acid construct which is not normally present in the cell would be considered heterologous for purposes of this invention. Allelic variation or naturally occurring mutational events do not give rise to heterologous peptides, as used herein.

As used herein, the term "inhibit" may refer to the act of blocking, reducing, eliminating, or otherwise antagonizing the presence, or an activity of, a particular target. Inhibition may refer to partial inhibition or complete inhibition. For example, inhibiting an immune response may refer to any act leading to a blockade, reduction, elimination, or any other antagonism of an immune response. In other examples, inhibition of the expression of a nucleic acid may include, but not limited to reduction in the transcription of a nucleic acid, reduction of mRNA abundance (e.g., silencing mRNA transcription), degradation of mRNA, inhibition of mRNA translation, and so forth. In another example, inhibit may refer to the act of slowing or stopping growth; for example, retarding or preventing the growth of a tumor cell.

As used herein, the term "suppress" may refer to the act of decreasing, reducing, prohibiting, limiting, lessening, or otherwise diminishing the presence, or an activity of, a particular target. Suppression may refer to partial suppression or complete suppression. For example, suppressing an immune response may refer to any act leading to decreasing, reducing, prohibiting, limiting, lessening, or otherwise diminishing an immune response. In other examples, suppression of the expression of a nucleic acid may include, but not limited to reduction in the transcription of a nucleic acid, reduction of mRNA abundance (e.g., silencing mRNA transcription), degradation of mRNA, inhibition of mRNA translation, and so forth.

As used herein, the term "enhance" may refer to the act of improving, boosting, heightening, or otherwise increasing the presence, or an activity of, a particular target. For example, enhancing an immune response may refer to any act leading to improving, boosting, heightening, or otherwise increasing an immune response. In one exemplary example, enhancing an immune response may refer to employing an antigen and/or adjuvant to improve, boost, heighten, or otherwise increase an immune response. In other examples, enhancing the expression of a nucleic acid may include, but not limited to increase in the transcription of a nucleic acid, increase in mRNA abundance (e.g., increasing mRNA transcription), decrease in degradation of mRNA, increase in mRNA translation, and so forth.

As used herein, the term "modulate" may refer to the act of changing, altering, varying, or otherwise modifying the presence, or an activity of, a particular target. For example, modulating an immune response may refer to any act leading to changing, altering, varying, or otherwise modifying an immune response. In some examples, "modulate" refers to enhancing the presence or activity of a particular target. In some examples, "modulate" refers to suppressing the presence or activity of a particular target. In other examples, modulating the expression of a nucleic acid may include, but not limited to a change in the transcription of a nucleic acid, a change in mRNA abundance (e.g., increasing mRNA transcription), a corresponding change in degradation of mRNA, a change in mRNA translation, and so forth.

As used herein, the term "induce" may refer to the act of initiating, prompting, stimulating, establishing, or otherwise producing a result. For example, inducing an immune response may refer to any act leading to initiating, prompting, stimulating, establishing, or otherwise producing a desired immune response. In other examples, inducing the expression of a nucleic acid may include, but not limited to initiation of the transcription of a nucleic acid, initiation of mRNA translation, and so forth.

As used herein, a "peripheral blood mononuclear cells" or "PBMCs" refers to a heterogeneous population of blood cells having a round nucleus. Examples of cells that may be found in a population of PBMCs include lymphocytes such as T cells, B cells, NK cells (including natural killer T cells (NKT cells) and cytokine-induced killer cells (CIK cells)) and monocytes such as macrophages and dendritic cells. A "plurality of PBMCs" as used herein refers to a preparation of PBMCs comprising cells of at least two types of blood cells. In some embodiments, a plurality of PBMCs comprises two or more of T cells, B cells, NK cells, macrophages or dendritic cells. In some embodiments, a plurality of PBMCs comprises three or more of T cells, B cells, NK cells, macrophages or dendritic cells. In some embodiments, a plurality of PBMCs comprises four or more of T cells, B cells, NK cells, macrophages or dendritic cells. In some embodiments, a plurality of PBMCs comprises T cells, B cells, NK cells, macrophages and dendritic cells.

PBMCs can be isolated by means known in the art. For example, PBMCs can be derived from peripheral blood of an individual based on density of PBMCs compared to other blood cells. In some embodiments, PBMCs are derived from peripheral blood of an individual using Ficoll (e.g., a ficoll gradient). In some embodiments, PBMCs are derived from peripheral blood of an individual using ELUTRA® cell separation system. PBMCs can be obtained from an individual undergoing apheresis.

In some embodiments, a population of PBMCs is isolated from an individual. In some embodiments, a plurality of PBMCs is an autologous population of PBMCs where the population is derived from a particular individual, manipulated by any of the methods described herein, and returned to the particular individual. In some embodiments, a plurality of PBMCs is an allogeneic population of PBMCs where the population is derived from one individual, manipulated by any of the methods described herein, and administered to a second individual.

In some embodiments, a plurality of PBMCs is a reconstituted preparation of PBMCs. In some embodiments, the plurality of PBMCs may be generated by mixing cells typically found in a population of PBMCs; for example, by mixing populations of two or more of T cells, B cells, NK cells, or monocytes.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and phosphorothioates, and thus can be an oligodeoxynucleoside phosphoramidate (P—NH2), a mixed phosphorothioate-phosphodiester oligomer, or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

As used herein, the term "adjuvant" refers to a substance which modulates and/or engenders an immune response. Generally, the adjuvant is administered in conjunction with an antigen to effect enhancement of an immune response to the antigen as compared to antigen alone. Various adjuvants are described herein.

The terms "CpG oligodeoxynucleotide" and "CpG ODN" herein refer to DNA molecules of 10 to 30 nucleotides in length containing a dinucleotide of cytosine and guanine separated by a phosphate (also referred to herein as a "CpG" dinucleotide, or "CpG"). The CpG ODNs of the present disclosure contain at least one unmethylated CpG dinucleotide. That is, the cytosine in the CpG dinucleotide is not methylated (i.e., is not 5-methylcytosine). CpG ODNs may have a partial or complete phosphorothioate (PS) backbone.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

The term "Ras", as used herein refers to any member of the to a group of the small guanosine triphosphate (GTP) binding proteins known as Ras superfamily or Tas-like GTPases, and includes all homologues including those in mammals such as primates (e.g. humans), non-human primates (e.g. cynomolgus monkeys), and rodents (e.g. mice and rats), unless otherwise indicated. The term encompasses "full-length," unprocessed Ras as well as any form of Ras which results from processing in the cell. The term also encompasses wild-type occurring isoform variants of Ras, e.g., splice variants or allelic variants. In humans, three Ras genes encode highly homologous Ras proteins, H-as, N-Ras and K-Ras. K-RAS includes two forms: K-RasA and K-RasB. The amino acid sequence of human K-Ras is shown in UniProt (world wide web.uniprot.org) accession no. P01116 (version 241). Specifically, the amino acid sequence of human K-Ras isoform a (known as K-Ras4A) is shown in UniProt (world wide web.uniprot.org) accession no. P01116-1 (version 241) and NCBI (world wide web.ncbi.nlm.nih.gov/) RefSeq NP_203524.1. The amino acid sequence of human K-Ras isoform b (known as K-Ras4B) is shown in UniProt (world wide web.uniprot.org) accession no. P01116-2 (version 241) and NCBI (world wide web.ncbi.nlm.nih.gov/) RefSeq NP_004976.2. The N-terminal domain of human K-Ras extends from amino acid position 1 to 86.

For any of the structural and functional characteristics described herein, methods of determining these characteristics are known in the art.

Methods of Treatment of Diseases Associated with Ras Mutation

In some aspects, provided are methods for stimulating an immune response to a mutated Ras protein in an individual, the method comprising administering an effective amount of a composition comprising nucleated cells (e.g., PBMCs) to an individual, wherein the nucleated cells comprise a mutated Ras antigen; wherein the mutated Ras antigen is delivered to the nucleated cell intracellularly. In some embodiments, the method comprises administering an effective amount of any of the compositions described herein. In some embodiments, the individual has cancer.

In some aspects, provided are methods for reducing tumor growth in an individual, the method comprising administering an effective amount of a composition comprising nucleated cells (e.g., PBMCs) to an individual, wherein the nucleated cells comprise a mutated Ras antigen; wherein the mutated Ras antigen is delivered to the nucleated cell intracellularly. In some embodiments, the method comprises administering an effective amount of any of the compositions described herein. In some embodiments, the individual has cancer.

In some aspects, provided are methods for vaccinating an individual in need thereof, the method comprising administering an effective amount of a composition comprising nucleated cells (e.g., PBMCs) to an individual, wherein the nucleated cells comprise a mutated Ras antigen; wherein the mutated Ras antigen is delivered to the nucleated cell intracellularly. In some embodiments, the method comprises administering an effective amount of any of the compositions described herein. In some embodiments, the individual has cancer.

In some aspects, provided are methods for treating cancer in an individual, the method comprising administering an effective amount of a composition comprising nucleated cells (e.g., PBMCs) to an individual, wherein the nucleated cells comprise a mutated Ras antigen; wherein the mutated Ras antigen delivered to the nucleated cell intracellularly. In some embodiments, the method comprises administering an effective amount of any of the compositions described herein.

In some aspects, there is provided a method for stimulating an immune response to a mutated Ras protein in an individual, comprising: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mutated Ras antigen to pass through to form a perturbed input nucleated cells; b) incubating the perturbed input nucleated cells with the mutated Ras antigen for a sufficient time to allow the mutated Ras antigen to enter the perturbed input nucleated cells; thereby generating nucleated cells comprising the mutated Ras antigen; and c) administering an effective amount of the nucleated cells comprising the mutated Ras antigen to the individual.

In some embodiments according to any of the methods described herein, the methods comprises: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for a nucleic acid encoding the mutated Ras antigen to pass through to form a perturbed input nucleated cells; b) incubating the perturbed input nucleated cells with the nucleic acid encoding the mutated Ras antigen for a sufficient time to allow the nucleic acid encoding the mutated Ras antigen to enter the perturbed input nucleated cells, wherein the nucleic acid expressed the mutated Ras antigen; thereby generating nucleated cells comprising the mutated Ras antigen; and c) administering an effective amount of the nucleated cells comprising the mutated Ras antigen to the individual.

In some embodiments according to any of the methods described herein, the methods comprises: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mutated Ras antigen to pass through to form a perturbed input nucleated cells; b) incubating the perturbed input nucleated cells with the mutated Ras antigen for a sufficient time to allow the mutated Ras antigen to enter the perturbed input nucleated cells, thereby generating nucleated cells comprising the mutated Ras antigen; c) incubating the nucleated cells with the adjuvant for a sufficient time for the nucleated cells to condition, thereby generating conditioned nucleated cells comprising the mutated Ras antigen; and d) administering an effective amount of the conditioned nucleated cells comprising the mutated Ras antigen to the individual. In some embodiments, the method comprises: a) incubating the input nucleated cells with an adjuvant for a sufficient time for the nucleated cells to condition, thereby generating conditioned input nucleated cells; b) passing a cell suspension comprising the conditioned input nucleated cells through a cell-deforming constriction, wherein a diameter of the constriction is a function of a diameter of the conditioned input nucleated cells in the suspension, thereby causing perturbations of the conditioned input nucleated cells large enough for the mutated Ras antigen to pass through to form perturbed conditioned input nucleated cells; c) incubating the perturbed conditioned input nucleated cells with the mutated Ras antigen for a sufficient time to allow the mutated Ras antigen to enter the perturbed conditioned input nucleated cells; thereby generating conditioned nucleated cells comprising the mutated Ras antigen; and d) administering an effective amount of the conditioned nucleated cells comprising the mutated Ras antigen to the individual.

In some embodiments according to any of the methods described herein, the methods comprises: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for a nucleic acid encoding the mutated Ras antigen to pass through to form a perturbed input nucleated cells; b) incubating the perturbed input nucleated cells with the nucleic acid encoding the mutated Ras antigen for a sufficient time to allow the nucleic acid encoding the mutated Ras antigen to enter the perturbed input nucleated cells; thereby generating nucleated cells comprising the nucleic acid encoding mutated Ras antigen, wherein the nucleic acid encoding the mutated Ras antigen is expressed thereby generating nucleated cells comprising a mutated Ras antigen; and c) incubating the nucleated cells with the adjuvant for the nucleated cells for a sufficient time to condition, thereby generating the conditioned nucleated cells comprising the mutated Ras antigen; and d) administering an effective amount of the conditioned nucleated cells comprising the mutated Ras antigen to the individual. In some embodiments, the method comprises: a) incubating the input nucleated cells with an adjuvant for a sufficient time for the nucleated cells to condition, thereby generating conditioned input nucleated cells; b) passing a cell suspension comprising the conditioned input nucleated cells through a cell-deforming constriction, wherein a diameter of the constriction is a function of a diameter of the conditioned input nucleated cells in the suspension, thereby causing perturbations of the conditioned input nucleated cells large enough for a nucleic acid encoding the mutated Ras antigen to pass through to form perturbed conditioned input nucleated cells; c) incubating the perturbed conditioned input nucleated cells with the nucleic acid encoding the mutated Ras antigen for a sufficient time to allow the nucleic acid encoding the mutated Ras antigen to enter the perturbed input nucleated cells; thereby generating conditioned nucleated cells comprising the nucleic acid encoding mutated Ras antigen, wherein the nucleic acid encoding the mutated Ras antigen is expressed thereby generating conditioned nucleated cells comprising a mutated Ras antigen, thereby generating conditioned nucleated cells comprising the mutated Ras antigen; and d) administering an effective amount of the conditioned nucleated cells comprising the mutated Ras antigen to the individual.

In some embodiments, there is provided a composition for stimulating an immune response to mutated Ras protein in an individual, wherein the composition comprises an effective amount of any one of the compositions comprising nucleated cells comprising a mutated Ras described herein. In some embodiments, there is provided a composition for reducing tumor growth, wherein the composition comprises an effective amount of any one of the compositions comprising nucleated cells comprising mutated antigens described herein. In some embodiments, the individual has cancer. In some embodiments, there is provided a composition for treating cancer in an individual, wherein the composition comprises an effective amount of any one of the compositions comprising nucleated cells comprising a mutated Ras described herein. In some embodiments, the cancer is a pancreatic cancer, a colon cancer, a small intestine cancer, a biliary tract cancer, an endometrial cancer, a lung cancer, a skin cancer, an ovarian cancer, a stomach cancer, an esophageal cancer, a cervical cancer or a urinary tract cancer.

In some embodiments, there is provided the use of a composition comprising an effective amount of nucleated cells in the manufacture of a medicament for stimulating an immune response to mutated Ras protein, wherein the composition comprises an effective amount of any one of the compositions comprising nucleated cells comprising a mutated Ras antigen described herein. In some embodiments, there is provided the use of a composition comprising an effective amount of nucleated cells in the manufacture of a medicament for reducing tumor growth in an individual, wherein the composition comprises an effective amount of any one of the compositions comprising nucleated cells comprising a mutated Ras antigen described herein. In some embodiments, the individual has cancer. In some embodiments, there is provided the use of a composition comprising an effective amount of nucleated cells in the manufacture of a medicament for treating cancer in an individual, wherein the composition comprises an effective amount any one of the compositions comprising nucleated cells comprising a mutated Ras antigen described herein.

In some embodiments according to the methods, uses or compositions described herein, the individual has cancer. In some embodiments, the cancer is pancreatic cancer, colon cancer, lung cancer (including but not limited to non-small-cell lung cancer), biliary tract cancer, bladder cancer, liver cancer, myeloid leukemia and breast cancer. In some embodiments, the cancer is a pancreatic cancer, a colon cancer, a small intestine cancer, a biliary tract cancer, an endometrial cancer, a lung cancer, an ovarian cancer, a stomach cancer, an esophageal cancer, a skin cancer, a cervical cancer or a urinary tract cancer. In some embodiments, the cancer is a solid cancer. In some embodiments, the cancer is a liquid cancer. In some embodiments, the cancer is a hematologic cancer. In some embodiments, the cancer is a cancer associated with Ras mutation. In some embodiments, the mutated Ras antigen is a cancer antigen found in a cancer associated with Ras mutation. In some embodiments, the cancer is a localized cancer. In some embodiments, the cancer is a metastatic cancer.

In some embodiments, the width of the constriction is about 10% to about 99% of the mean diameter of the input nucleated cells. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input nucleated cells having the smallest diameter within the population of nucleated cells. In some embodiments, the width of the constriction about 3 μm to about 5 μm, about 3 μm to about 3.5 μm, about 3.5 μm to about 4 μm, about 4 μm to about 4.5 μm, about 3.2 μm to about 3.8 μm, about 3.8 μm to about 4.3 μm, about 4.2 μm to about 6 μm, or about 4.2 μm to about 4.8 μm. In some embodiments, the width of the constriction is about 4.5 μm. In some embodiments, the width of the constriction is about or less than any one of 2 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, 10.5 μm, 11 μm, 11.5 μm, 12 μm, 12.5 μm, 13 μm, 13.5 μm, 14 μm, 14.5 μm or 15 μm. In some embodiments, the cell suspension comprising the input nucleated cells are passed through multiple constrictions wherein the multiple constrictions are arranged in series and/or in parallel.

In some embodiments according to any one of the methods, uses or compositions described herein, the nucleated cells (e.g., PBMCs) are incubated with the adjuvant for a sufficient time for the nucleated cells to condition. In some embodiments, the nucleated cells are incubated with the adjuvant for about 1 to about 24 hours for the nucleated cells to condition. In some embodiments, the nucleated cells are incubated with the adjuvant for about 2 to about 10 hours for the nucleated cells to condition. In some embodiments, the nucleated cells are incubated with the adjuvant for about 3 to about 6 hours for the nucleated cells to condition. In some embodiments, the nucleated cells are incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the nucleated cells to condition. In some embodiments, the nucleated cells are incubated with the adjuvant for about 4 hours for the nucleated cells to condition. In some embodiments, the nucleated cells are conditioned before introducing the mutated Ras antigen or the nucleic acid encoding the mutated Ras antigen into the nucleated cells. In some embodiments, the nucleated cells are conditioned after introducing the mutated Ras antigen or the nucleic acid encoding the mutated Ras antigen into the nucleated cells. In some embodiments, the adjuvant used for conditioning is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic (poly I:C), R837, R848, a TLR3 agonist, a TLR4 agonist or a TLR9 agonist. In some embodiments, the adjuvant is a CpG oligodeoxynucleotide (ODN). In some embodiments, the adjuvant is CpG 7909.

In some embodiments, wherein the nucleated cells comprise B cells, one or more co-stimulatory molecules is upregulated in the B cells of the conditioned nucleated cells compared to the B cells of the unconditioned nucleated cells. In some embodiments, the nucleated cells are a plurality of peripheral blood mononuclear cells (PBMCs). In some embodiments, wherein the nucleated cells are a plurality of PBMCs, one or more co-stimulatory molecules is upregulated in the B cells of the conditioned plurality of PBMCs compared to the B cells of the unconditioned plurality of PBMCs. In some embodiments, the co-stimulatory molecule is CD80 and/or CD86. In some embodiments, the conditioned plurality of PBMCs has increased expression of one or more of IFN-γ, IL-6, MCP-1, MIP-1β, IP-10, or TNF-α compared to an unconditioned plurality of PBMCs. In some embodiments, the expression of one or more of IFN-γ, IL-6, MCP-1, MIP-1β, IP-10, or TNF-α is increased by more than about 1.2-fold, 1.5-fold, 1.8-fold, 2-fold, 3-fold, 4-fold, 5-fold, 8-fold, or more than 10-fold compared to an unconditioned plurality of PBMCs In some embodiments according to any one of the methods, uses or compositions described herein, the nucleated cells are immune cells. In some embodiments, the nucleated cells are human cells. In some embodiments, the nucleated cells are human cells with a haplotype of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16. In some embodiments, the nucleated cells are a plurality of PBMCs. In some embodiments, the conditioned nucleated cells are a conditioned plurality of modified PBMCs. In some embodiments, the plurality of PBMCs comprises two or more of T cell, B cell, NK cell, monocytes, dendritic cells or NK-T cells. In some embodiments, the nucleated cells are one or more of T cells, B cells, NK cells, monocytes, dendritic cells and/or NK-T cells.

In some embodiments, the plurality of PBMCs are further modified to increase expression of one or more of co-stimulatory molecules. In some embodiments, the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112. In some embodiments, the plurality of PBMCs are further modified to increase expression of one or more cytokines. In some embodiments, the cytokine is IL-10, IL-15, IL-12, IL-2, IFN-α, IFN-γ, or IL 21.

In some embodiments, the mutated Ras antigen is a pool of multiple polypeptides that elicit a response against the same and or different mutated Ras antigens. In some embodiments, the mutated Ras antigen is a polypeptide comprising one or more antigenic mutated Ras epitope and one or more heterologous peptide sequences. In some embodiments, the mutated Ras antigen complexes with other antigens or with an adjuvant. In some embodiments, the mutated Ras antigen comprises a G12D mutation, a G12V mutation, a G12C mutation or a G13D mutation. In some embodiments, the mutated Ras antigen is a polypeptide comprising one or more antigenic mutated Ras epitopes that is flanked on the N-terminus and/or the C-terminus by one or more heterologous peptide sequences. In some embodiments, the mutated Ras antigen is a polypeptide comprising one or more antigenic mutated Ras epitopes that is not flanked on the N-terminus and/or the C-terminus by one or more heterologous peptide sequences. In some embodiments, the mutated Ras antigen is one or more of a $G12D^{1-16}$, a $G12D^{2-19}$, a $G12D^{2-22}$, a $G12D^{2-29}$ a $G12V^{1-16}$, a $G12V^{2-19}$, a $G12V^{3-17}$, or a $G12V^{3-42}$ antigen. In some embodiments, the mutated Ras antigen comprises an amino acid sequence with at least 90% similarity to any one of SEQ ID NOs: 1-8. In some embodiments, the mutated Ras antigen comprises an amino acid sequence with at least any one of: 80%, 85%, 90%, or 95% similarity to any one of SEQ ID NOs: 1-8. In some embodiments, the mutated Ras antigen comprises an amino acid sequence of SEQ ID NOs: 1-8. In some embodiments, the mutated Ras antigen comprises an amino acid sequence with at least 90% similarity to any one of SEQ ID NOs: 9-15. In some embodiments, the mutated Ras antigen comprises an amino acid sequence of SEQ ID NOs: 9-15. In some embodiments, the mutated Ras antigen is capable of being processed into an MHC class I-restricted peptide. In some embodiments, the mutated Ras antigen is capable of being processed into an MHC class II-restricted peptide.

In some embodiments, the method comprises multiple administrations of the nucleated cells comprising the mutated Ras antigen. In some embodiments, the method comprises about 3 to about 9 administrations of the nucleated cells comprising the mutated Ras antigen. In some embodiments, the method comprises about any one of 1, 2, 3, 4, 5, 6, 7, 8, 9, 10, 11, 12, 13, 14 or 15 administrations of the nucleated cells comprising the mutated Ras antigen. In some embodiments, the method comprises continuous administrations of the modified PBMCs as needed. In some embodiments, the time interval between two successive administrations of the nucleated cells comprising the mutated Ras antigen is between about 1 day and about 30 days. In some embodiments, the time interval between two successive administrations of nucleated cells comprising the mutated Ras antigen is about 21 days. In some embodiments, the time the time interval between two successive administrations of the nucleated cells comprising the mutated Ras antigen is about any one of 1, 2, 3, 4, 5, 6, 7, 8, 10, 12, 14, 16, 20, 25, 30, 35, 40, 45, 50, 55, 60, 65, 70, 75, 80, 85, 90, 95, 100, or 150 days. In some embodiments, the time interval between the first two successive administrations of the nucleated cells comprising the mutated Ras antigen is 1 day or 2 days. In some embodiments, the time interval between the first two successive administrations of the nucleated cells comprising the mutated Ras antigen is 1 day or 2 days, wherein the method comprises more than 2 administration of the nucleated cells comprising the mutated Ras antigen (such as but not limited to 3, 4, 5, 6, 7, 8, 9, 10, 11, 12, 13, 14, 15 or more administrations). In some embodiments, the nucleated cells comprising the mutated Ras antigen are administered intravenously, intratumorally and/ or subcutaneously. In some embodiments, the nucleated cells comprising the mutated Ras antigen are administered intravenously.

In some embodiments, the composition further comprises an adjuvant. In some embodiments, the adjuvant is a CpG oligodeoxynucleotide (ODN), LPS, IFN-α, IFNγ, STING agonists, cyclic dinucleotides (CDN), alpha-Galactosyl Ceramide, RIG-I agonists, polyinosinic-polycytidylic, R837, R848, a TLR3 agonist, a TLR4 agonist or a TLR9 agonist. In some embodiments, the adjuvant is a CpG oligodeoxynucleotide. In some embodiments, the adjuvant is CpG 7909.

In some embodiments, the composition comprising the nucleated cells comprising the mutated Ras antigen and the adjuvant are administered simultaneously. In some embodiments, the composition comprising nucleated cells comprising the mutated Ras antigen and the adjuvant are administered sequentially. In some embodiments, the adjuvant and/or the nucleated cells comprising the mutated Ras antigen are administered intravenously, intratumorally and/or subcutaneously. In some embodiments, the adjuvant and/or the nucleated cells comprising the mutated Ras antigen are administered intravenously.

In some embodiments, the composition comprising nucleated cells comprising the mutated Ras antigen is administered prior to administering the adjuvant. For example, the composition comprising the nucleated cells comprising the mutated Ras antigen is administered from about 1 hour to about 1 week prior to administration of the adjuvant. For example, in some embodiments, the composition comprising the nucleated cells comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the adjuvant. In some embodiments, the composition comprising the nucleated cells comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the adjuvant.

In some embodiments, the composition comprising the nucleated cells comprising the mutated Ras antigen is administered following administration of the adjuvant. For example, the composition comprising the nucleated cells comprising the mutated Ras antigen is administered from about 1 hour to about 1 week following administration of the adjuvant. For example, in some embodiments, the composition comprising the nucleated cells comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the adjuvant. In some embodiments, the composition comprising the nucleated cells comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the adjuvant.

In some embodiments, the individual is positive for expression of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16. In some embodiments, the individual is positive for expression of HLA-A2. In some embodiments, at least one cell in the nucleated cells comprising the mutated Ras antigen is positive for expression of HLA-A2. In some embodiments, at least about any one of 10%, 20%, 30%, 40%, 50%, 60%, 70%, 80%, 90%, or 99% of the nucleated cells comprising the mutated Ras antigen is positive for expression of HLA-A2. In some embodiments, wherein the nucleated cells are a plurality of PBMCs, at least about any one of 10%, 20%, 30%, 40%, 50%, 60%, 70%, 80%, 90%, or 99% of T cells within the modified PBMCs comprising the mutated Ras antigen are positive for expression of HLA-A2. In some embodiments, at least about any one of 10%, 20%, 30%, 40%, 50%, 60%, 70%, 80%, 90%, or 99% of B cells within the modified PBMCs comprising the mutated Ras antigen are positive for expression of HLA-A2. In some embodiments, at least about any one of 10%, 20%, 30%, 40%, 50%, 60%, 70%, 80%, 90%, or 99% of NK cells within the modified PBMCs comprising the mutated Ras antigen are positive for expression of HLA-A2. In some embodiments, at least about any one of 10%, 20%, 30%, 40%, 50%, 60%, 70%, 80%, 90%, or 99% of monocytes within the modified PBMCs comprising the mutated Ras antigen are positive for expression of HLA-A2.

In some embodiments according to any one of the methods, uses or compositions described herein, the nucleated cells comprising the mutated Ras antigen are administered prior to, concurrently with, or following administration of a therapeutic agent. In some embodiments, the therapeutic agent comprises one or more of an immune checkpoint inhibitor, a chemotherapy, or a radiotherapy. In some embodiments, the therapeutic agent comprises one or more cytokines. In some embodiments, the therapeutic agent comprises one or more antibodies. In some embodiments, the therapeutic agent comprises one or more bispecific polypeptides used in immuno-oncology (e.g., an immuno-conjugate).

Immune checkpoints are regulators of the immune system and keep immune responses in check. Immune checkpoint inhibitors can be employed to facilitate the enhancement of immune response. In some embodiments, the composition comprising the nucleated cells comprising the mutated Ras antigen is administered in combination with administration of an immune checkpoint inhibitor. In some embodiments, the composition comprising the nucleated cells comprising the mutated Ras antigen and the immune checkpoint inhibitor are administered simultaneously. In some embodiments, the composition comprising the nucleated cells comprising the mutated Ras antigen and the immune checkpoint inhibitor are administered sequentially. In some embodiments, the immune checkpoint inhibitor and/or the nucleated cells comprising the mutated Ras antigen are administered intravenously, intratumorally and/or subcutaneously. In some embodiments, the immune checkpoint inhibitor and/or the nucleated cells comprising the mutated Ras antigen are administered intravenously.

In some embodiments, the composition comprising the nucleated cells comprising the mutated Ras antigen is administered prior to administration of the immune checkpoint inhibitor. In some embodiments, the composition comprising the nucleated cells comprising the mutated Ras antigen is administered following administration of the immune checkpoint inhibitor. For example, the composition comprising the nucleated cells comprising the mutated Ras antigen is administered from about 1 hour to about 1 week prior to administration of the immune checkpoint inhibitor. For example, in some embodiments, the composition comprising the nucleated cells comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the immune checkpoint inhibitor. In some embodiments, the composition comprising the nucleated cells comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the immune checkpoint inhibitor.

In some embodiments, the composition comprising the nucleated cells comprising the mutated Ras antigen is administered about 7 days, about 10 days, about 14 days, about 18 days, about 21 days, about 24 days, about 28 days, about 30 days, about 35 days, about 40 days, about 45 days, or about 50 days prior to administration of the immune checkpoint inhibitor. In some embodiments, the composition comprising the nucleated cells comprising the mutated Ras antigen is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days prior to administration of the immune checkpoint inhibitor.

In some embodiments, the composition comprising the nucleated cells comprising the mutated Ras antigen is administered following administration of the immune checkpoint inhibitor. For example, the composition comprising the nucleated cells comprising the mutated Ras antigen is administered from about 1 hour to about 1 week following administration of the immune checkpoint inhibitor. For example, in some embodiments, the composition comprising the nucleated cells comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the immune checkpoint inhibitor. In some embodiments, the composition comprising the nucleated cells comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the immune checkpoint inhibitor.

In some embodiments, the composition comprising the nucleated cells comprising the mutated Ras antigen is administered about 7 days, about 10 days, about 14 days, about 18 days, about 21 days, about 24 days, about 28 days, about 30 days, about 35 days, about 40 days, about 45 days, or about 50 days following administration of the immune checkpoint inhibitor. In some embodiments, the composition comprising the nucleated cells comprising the mutated Ras antigen is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days following administration of the immune checkpoint inhibitor.

In some embodiments, the method comprises multiple administration of the composition comprising the nucleated cells comprising the mutated Ras antigen and/or multiple administration of the immune checkpoint inhibitor. For example, in some embodiments, the method comprises two administrations, three administrations, four administrations, five administrations, six administrations, seven administrations, eight administrations, nine administrations, ten administrations, eleven administrations, twelve administrations, thirteen administrations, fourteen administrations, or fifteen administrations of the composition comprising the nucleated cells comprising the mutated Ras antigen and/or the immune checkpoint inhibitor. For example, in some embodiments, the method comprises less than five administrations, less than ten administrations, less than fifteen administrations, less than twenty administrations, less than twenty-five administrations, less than thirty administrations, less than fifty administrations, less than seventy-five administrations, less than one hundred, or less than two hundred administrations of the composition comprising the nucleated cells comprising the mutated Ras antigen and/or the immune checkpoint inhibitor.

Exemplary immune checkpoint inhibitor is targeted to, without limitation, PD-1, PD-L1, CTLA-4, LAG3, TIM-3, TIGIT, VISTA, TIM1, B7-H4 (VTCN1) or BTLA. In some embodiments, the immune checkpoint inhibitor is targeted to one or more of PD-1, PD-L1, CTLA-4, LAG3, TIM-3, TIGIT, VISTA, TIM1, B7-H4 (VTCN1) or BTLA. In some embodiments, the immune checkpoint inhibitor is one or more of: an antibody that binds to PD-1, an antibody that binds PD-L1, an antibody that binds CTLA-4, an antibody that binds LAG3, or an antibody that binds TIM-3, an antibody that binds TIGIT, an antibody that binds VISTA, an antibody that binds TIM-1, an antibody that binds B7-H4, or an antibody that binds BTLA. In further embodiments, the antibody can be a full-length antibody or any variants, for example but not limited to, an antibody fragment, a single chain variable fragment (ScFv), or a fragment antigen-binding (Fab). In further embodiments, the antibody can be bispecific, trispecific or multispecific. In some embodiments, the immune checkpoint inhibitor is one or more chemical compounds that binds to and/or inhibits one or more of PD-1, PD-L1, CTLA-4, LAG3, TIM-3, TIGIT, VISTA, TIM1, B7-H4 (VTCN1) or BTLA. In some embodiments, the immune checkpoint inhibitor is one or more peptides that binds to and/or inhibits one or more of PD-1, PD-L1, CTLA-4, LAG3, TIM-3, TIGIT, VISTA, TIM1, B7-H4 (VTCN1) or BTLA. In some embodiments, the immune checkpoint inhibitor is targeted to PD-1. In some embodiments, the immune checkpoint inhibitor is targeted to PD-L1.

Cytokines can be used in combination with any one of the pluralities of modified PBMCs described herein to achieve additive or synergistic effects against cancers, for example, mutated Ras-associated cancers. In some embodiments, the composition comprising the nucleated cells comprising the mutated Ras antigen is administered in combination with administration of one or more cytokines. In some embodiments, the composition comprising the nucleated cells comprising the mutated Ras antigen and the cytokine are administered simultaneously. In some embodiments, the composition comprising the nucleated cells comprising the mutated Ras antigen and the cytokine are administered sequentially.

In some embodiments, the composition comprising the nucleated cells comprising the mutated Ras antigen is administered prior to administration of the cytokine In some embodiments, the composition comprising the nucleated cells comprising the mutated Ras antigen is administered following administration of the cytokine. For example, the composition comprising the nucleated cells comprising the mutated Ras antigen is administered from about 1 hour to about 1 week prior to administration of the cytokine. For example, in some embodiments, the composition comprising the nucleated cells comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the cytokine. In some embodiments, the composition comprising the nucleated cells comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the cytokine.

In some embodiments, the composition comprising the nucleated cells comprising the mutated Ras antigen is administered about 7 days, about 10 days, about 14 days, about 18 days, about 21 days, about 24 days, about 28 days, about 30 days, about 35 days, about 40 days, about 45 days, or about 50 days prior to administration of the cytokine. In some embodiments, the composition comprising the nucleated cells comprising the mutated Ras antigen is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days prior to administration of the cytokine.

In some embodiments, the composition comprising the nucleated cells comprising the mutated Ras antigen is administered following administration of the cytokine. For example, the composition comprising the nucleated cells comprising the mutated Ras antigen is administered from about 1 hour to about 1 week following administration of the cytokine. For example, in some embodiments, the composition comprising the nucleated cells comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the cytokine. In some embodiments, the composition comprising the nucleated cells comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the cytokine.

Exemplary cytokines include but are not limited to chemokines, interferons, interleukins, lymphokines, and tumor necrosis factors, or functional derivatives thereof. In some embodiments, the cytokine enhances cellular immune responses. In some embodiments, the cytokine enhances antibody responses. In some embodiments, the cytokine is a type I cytokine. In some embodiments, the cytokine is a type 2 cytokine. In some embodiments, the cytokine comprises one or more of: IL-2, IL-15, IL-10, IL-12, IFN-α, or IL-21. In some embodiments, the cytokine comprises IL-15.

In some embodiments, the composition comprising the nucleated cells comprising the mutated Ras antigen is administered prior to administration of a bispecific polypeptide comprising a cytokine moiety. In some embodiments, the composition comprising the nucleated cells comprising the mutated Ras antigen is administered prior to administration of a bispecific polypeptide comprising a cytokine moiety and an immune checkpoint inhibitor moiety. In some embodiments, the bispecific polypeptide comprises a CD3 targeting moiety and a tumor antigen targeting moiety. In some embodiments, the bispecific polypeptide comprises moieties that target two immune checkpoints. In some embodiments, the bispecific polypeptide comprises a moiety that targets antigens found in stroma or expressed on cancer-associated fibroblasts. In some embodiments, the bispecific polypeptide comprises a moiety that targets antigens found in stroma or expressed on cancer-associated fibroblasts and a cytokine moiety.

Chemotherapy can be used in combination with any one of the pluralities of modified PBMCs described herein to achieve additive or synergistic effects against cancers, for example, mutated Ras-associated cancers. In some embodiments, the composition comprising the nucleated cells comprising the mutated Ras antigen is administered in combination with administration of a chemotherapy. In some embodiments, the composition comprising the nucleated cells comprising the mutated Ras antigen and the chemotherapy are administered simultaneously. In some embodiments, the composition comprising the nucleated cells comprising the mutated Ras antigen and the chemotherapy are administered sequentially.

In some embodiments, the composition comprising the nucleated cells comprising the mutated Ras antigen is administered prior to administration of the chemotherapy. In some embodiments, the composition comprising the nucleated cells comprising the mutated Ras antigen is administered following administration of the chemotherapy. For example, the composition comprising the nucleated cells comprising the mutated Ras antigen is administered from about 1 hour to about 1 week prior to administration of the chemotherapy. For example, in some embodiments, the composition comprising the nucleated cells comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the chemotherapy. In some embodiments, the composition comprising the nucleated cells comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the chemotherapy.

In some embodiments, the composition comprising the nucleated cells comprising the mutated Ras antigen is administered following administration of the chemotherapy. For example, the composition comprising the nucleated cells comprising the mutated Ras antigen is administered from about 1 hour to about 1 week following administration of the chemotherapy. For example, in some embodiments, the composition comprising the nucleated cells comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the chemotherapy. In some embodiments, the composition comprising the nucleated cells comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the chemotherapy.

In some embodiments, the composition comprising the nucleated cells comprising the mutated Ras antigen is administered about 7 days, about 10 days, about 14 days, about 18 days, about 21 days, about 24 days, about 28 days, about 30 days, about 35 days, about 40 days, about 45 days, or about 50 days following administration of the chemotherapy. In some embodiments, the composition comprising the nucleated cells comprising the mutated Ras antigen is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days following administration of the chemotherapy.

In some embodiments, the method comprises multiple administration of the administration of the chemotherapy. For example, in some embodiments, the method comprises two administrations, three administrations, four administrations, five administrations, six administrations, seven administrations, eight administrations, nine administrations, ten administrations, eleven administrations, twelve administrations, thirteen administrations, fourteen administrations, or fifteen administrations of the composition comprising the nucleated cells comprising the mutated Ras antigen and/or the chemotherapy. For example, in some embodiments, the method comprises less than five administrations, less than ten administrations, less than fifteen administrations, less than twenty administrations, less than twenty-five administrations, less than thirty administrations, less than fifty administrations, less than seventy-five administrations, less than one hundred, or less than two hundred administrations of the composition comprising the nucleated cells comprising the mutated Ras antigen and/or the chemotherapy.

Exemplary chemotherapy can be cell cycle dependent or cell cycle independent. In some embodiments, the chemotherapy comprises one or more chemotherapeutic agents. In some embodiments, a chemotherapeutic agent can target one or more of cell division, DNA, or metabolism in cancer. In some embodiments, the chemotherapeutic agent is a platinum-based agent, such as but not limited to cisplatin, oxaliplatin or carboplatin. In some embodiments, the chemotherapeutic agent is a taxane (such as docetaxel or paclitaxel). In some embodiments, the chemotherapeutic agent is 5-fluorouracil, doxorubicin, or irinotecan. In some embodiments, the chemotherapeutic agent is one or more of: an alkylating agent, an antimetabolite, an antitumor antibiotic, a topoisomerase inhibitor or a mitotic inhibitor. In some embodiments, the chemotherapy comprises cisplatin.

Radiotherapy can be used in combination with any one of the pluralities of modified PBMCs described herein to achieve additive or synergistic effects against cancers, for example, mutated Ras-associated cancers. In some embodiments, the composition comprising the nucleated cells comprising the mutated Ras antigen is administered in combination with administration of a radiotherapy. In some embodiments, the composition comprising the nucleated cells comprising the mutated Ras antigen and the radiotherapy are administered simultaneously. In some embodiments, the composition comprising the nucleated cells comprising the mutated Ras antigen and the radiotherapy are administered sequentially. In some embodiments, the composition comprising the nucleated cells comprising the mutated Ras antigen is administered in combination with administration of a radiotherapy, in combination with a chemotherapy, and/or in combination with an immune checkpoint inhibitor.

In some embodiments, the composition comprising the nucleated cells comprising the mutated Ras antigen is administered prior to administration of the radiotherapy. In some embodiments, the composition comprising the nucleated cells comprising the mutated Ras antigen is administered following administration of the radiotherapy. For example, the composition comprising the nucleated cells comprising the mutated Ras antigen is administered from about 1 hour to about 1 week prior to administration of the radiotherapy. For example, in some embodiments, the composition comprising the nucleated cells comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the radiotherapy. In some embodiments, the composition comprising the nucleated cells comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the radiotherapy.

In some embodiments, the composition comprising the nucleated cells comprising the mutated Ras antigen is administered following administration of the radiotherapy. For example, the composition comprising the nucleated cells comprising the mutated Ras antigen is administered from about 1 hour to about 1 week following administration of the radiotherapy. For example, in some embodiments, the composition comprising the nucleated cells comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the radiotherapy. In some embodiments, the composition comprising the nucleated cells comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the radiotherapy.

In some embodiments, the composition comprising the nucleated cells comprising the mutated Ras antigen is administered about 7 days, about 10 days, about 14 days, about 18 days, about 21 days, about 24 days, about 28 days, about 30 days, about 35 days, about 40 days, about 45 days, or about 50 days following administration of the radiotherapy. In some embodiments, the composition comprising the nucleated cells comprising the mutated Ras antigen is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days following administration of the radiotherapy.

In some embodiments, the method comprises multiple administration of the administration of the radiotherapy. For example, in some embodiments, the method comprises two administrations, three administrations, four administrations, five administrations, six administrations, seven administrations, eight administrations, nine administrations, ten administrations, eleven administrations, twelve administrations, thirteen administrations, fourteen administrations, or fifteen administrations of the composition comprising the nucleated cells comprising the mutated Ras antigen and/or the radiotherapy. For example, in some embodiments, the method comprises less than five administrations, less than ten administrations, less than fifteen administrations, less than twenty administrations, less than twenty-five administrations, less than thirty administrations, less than fifty administrations, less than seventy-five administrations, less than one hundred, or less than two hundred administrations of the composition comprising the nucleated cells comprising the mutated Ras antigen and/or the radiotherapy.

In some embodiments, there is provided a plurality of nucleated cells (e.g. PBMCs) comprising a mutated Ras antigen for use in a method of stimulating an immune response in an individual according to any one of the methods described herein.

Ras Antigens

In some embodiments, provided are methods for stimulating an immune response in an individual to a mutated Ras protein, the method comprising a) administering an effective amount of a composition comprising nucleated cells (e.g., PBMCs) to an individual, wherein the nucleated cells comprise a constriction-delivered mutated Ras antigen intracellularly.

In some embodiments, the mutated Ras antigen comprise one or more mutations compared to the corresponding wild type Ras protein. In some embodiments, the mutated Ras antigen is a mutated K-Ras antigen (e.g, a mutated K-Ras4A or mutated K-Ras4B), a mutated H-Ras antigen, or a mutated N-Ras antigen. In some embodiments, the mutated Ras antigen is a disease-associated antigen (such as cancer-associated antigen). In some embodiments, the mutated Ras antigen is derived from peptides or mRNA isolated from a diseased cell (such as cancer cells). In some embodiments, the mutated Ras antigen is a non-self antigen. In some embodiments, the mutated Ras antigen is derived from a lysate, such as a lysate of disease cells. In some embodiments, the mutated Ras antigen is derived from a tumor lysate. In some embodiments, the mutated Ras antigen is a tumor antigen or a tumor associated antigen. In some embodiments, the mutated Ras antigen is associated with a cancer. In some embodiments, the cancer is a pancreatic cancer, a colon cancer, a small intestine cancer, a biliary tract cancer, an endometrial cancer, a lung cancer, a skin cancer, an ovarian cancer, a stomach cancer, an esophageal cancer, a cervical cancer or a urinary tract cancer. In some embodiments, the mutated Ras antigen is a pancreatic cancer antigen, a colon cancer antigen, a small intestine cancer antigen, a biliary tract cancer antigen, an endometrial cancer antigen, a lung cancer antigen, a skin cancer antigen, an ovarian cancer, a stomach cancer, an esophageal cancer, a cervical cancer antigen or a urinary tract cancer antigen. In some embodiments, the cancer is a solid cancer. In some embodiments, the cancer is a liquid cancer. In some embodiments, the cancer is a hematologic cancer. In some embodiments, the cancer is a virus-associated cancer. In some embodiments, the mutated Ras antigen is a cancer antigen found in a Ras-associated cancer. In some embodiments, the cancer is a localized cancer. In some embodiments, the cancer is a metastatic cancer.

In some embodiments according to the methods described herein, the mutated Ras antigen comprises one or more proteins. In some embodiments, the mutated Ras antigen is encoded by one or more nucleic acids and enters the nucleated cells in the form of one or more nucleic acids, such as but not limited to DNAs, cDNAs, mRNAs, and plasmids. In some embodiments, the mutated Ras antigen is encoded by one or more mRNAs and enters the nucleated cells in the form of one or more mRNAs.

K-Ras belongs to a group of small guanosine triphosphate (GTP) binding proteins, known as RAS superfamily or RAS-like GTPases. Members of RAS superfamily are divided into families and subfamilies based on their structure, sequence and function. In humans, three RAS genes encode highly homologous RAS proteins, H-Ras, N-Ras and K-Ras. Ras is one of the most frequently mutated oncogenes in human cancer, and K-Ras is the isoform most frequently mutated, which constitutes 86% of RAS mutations. The K-Ras-4B splice variant is the dominant isoform with mutations in human cancers, and it is present in approximately 90% of pancreatic cancers, 30% to 40% of colon cancers, and 15% to 20% of lung cancers, mostly non-small-cell lung cancer (NSCLC). It is also present in biliary tract malignancies, endometrial cancer, cervical cancer, bladder cancer, liver cancer, myeloid leukemia and breast cancer. The mutations found most frequently in the K-Ras gene are primarily at codons 12, 13, or 61. K-Ras mutations also occur in codons 63, 117, 119, and 146 but with less frequency. In details, mutation of glycine 12 (G12) causes RAS activation by interfering with GAP binding and GAP-stimulated GTP hydrolysis. Mutations at residue 13 sterically clash with the arginine and decrease GAP binding and hydrolysis. Mutations at residues 12, 13 and 61 were reported to decrease the affinity for the RAS-binding domain (RBD) of RAF as well but with different extent. In some embodiments, the mutated Ras antigen is a mutated K-Ras antigen, a mutated H-Ras antigen, and/or a mutated N-Ras antigen. In some embodiments, the mutated K-Ras antigen is a mutated K-Ras-4A antigen, and/or a K-Ras-4B antigen.

In some embodiments, the mutated Ras antigen is a pool of multiple polypeptides that elicit a response against the same and or different mutated Ras antigens. In some embodiments, an antigen in the pool of multiple antigens does not decrease the immune response directed toward other antigens in the pool of multiple antigens. In some embodiments, the mutated Ras antigen is a polypeptide comprising an antigenic mutant Ras epitope and one or more heterologous peptide sequences. In some embodiments, the mutated Ras antigen complexes with itself, with other antigens, or with the adjuvant. In some embodiments, the mutated Ras antigen is comprised of an HLA-A2-specific epitope. In some embodiments, the mutated Ras antigen is comprised of an HLA-A11-specific epitope. In some embodiments, the mutated Ras antigen is comprised of an HLA-B7-specific epitope. In some embodiments, the mutated Ras antigen is comprised of an HLA-C8-specific epitope. In some embodiments, the mutated Ras antigen is a mutated Ras antigen comprising an mutation in its N-terminus. In some embodiments, the mutated Ras antigen is a mutated Ras antigen comprising a G12D mutation, a G12V mutation, a G12C mutation or a G13D mutation. In some embodiments, the mutated Ras antigen comprises part or all of the N-terminal domain of a full-length mutated Ras protein. In some embodiments, a mutant Ras protein (such as mutant K-Ras) having its 12th residue in the N-terminal domain mutated from Glycine (G) to Aspartic Acid (D) is referred to Ras-G12D. In some embodiments, a mutant K-Ras protein having its 12th residue in the N-terminal domain mutated from Glycine (G) to Aspartic Acid (D) is referred to as K-Ras-G12D. As used herein, a mutant Ras protein (such as mutant K-Ras) having its 12th residue in the N-terminal domain mutated from Glycine to Valine (V) is referred to as Ras-G12V. As used herein, a mutant K-Ras protein having its 12th residue in the N-terminal domain mutated from Glycine (G) to Valine (V) is referred to as K-Ras-G12V. As used herein, a mutant Ras protein (such as mutant K-Ras) having its 12th residue in the N-terminal domain mutated from Glycine to Cysteine (C) is referred to as Ras-G12C. As used herein, a mutant K-Ras protein having its 12th residue in the N-terminal domain mutated from Glycine (G) to Cysteine (C) is referred to as K-Ras-G12C. As used herein, a mutant Ras protein (such as mutant K-Ras) having its 13th residue in the N-terminal domain mutated from Glycine to Aspartic Acid (D) is referred to as Ras-G13D. As used herein, a mutant K-Ras protein having its 13th residue in the N-terminal domain mutated from Glycine (G) to Aspartic Acid (D) is referred to as K-Ras-G13D.

In some embodiments, the sequence of an antigen or an antigenic epitope comprising residue X to residue Y of the N-terminal domain of a mutant Ras-G12D protein is referred to as $G12D^{X-Y}$ or Ras-$G12D^{X-Y}$. As a non-limiting example, the sequence of an antigen or an antigen epitope comprising residue 1 to residue 16 of the N-terminal domain of a mutant K-Ras-G12D protein is referred to as $G12D^{1-16}$ or K-Ras-$G12D^{1-16}$. In some embodiments, the sequence of an antigen or an antigenic epitope comprising residue X to residue Y of the N-terminal domain of a mutant Ras-G12V protein is referred to as $G12D^{X-Y}$ or Ras-$G12D^{X-Y}$. As a non-limiting example, the sequence of an antigen or an antigenic epitope comprising residue 2 to residue 22 of the N-terminal domain of a mutant K-Ras-G12V protein is referred to as $G12V^{2-22}$ or K-Ras-$G12V^{2-22}$.

In some embodiments, the mutated Ras antigen comprises a peptide derived from K-Ras comprising one or more of a G12D mutation (K-Ras-G12D), a peptide from K-Ras comprising a G12V mutation (K-Ras-G12V)), a peptide from K-Ras comprising a G12C mutation (K-Ras-G12C), a peptide from K-Ras comprising a G13D mutation (K-Ras-G13D). In some embodiments, the antigen comprises an HLA-A2-restricted peptide derived from K-Ras-G12D, a HLA-A2-restricted peptide derived from K-Ras-G12V, an HLA-A2-restricted peptide derived from K-Ras-G12C, and/or an HLA-A2-restricted peptide derived from K-Ras-G13D. In some embodiments, the antigen comprises a $G12D^{1-16}$, a $G12D^{2-19}$, a $G12D^{2-22}$, a $G12D^{2-29}$ $G12V^{1-16}$, a $G12V^{2-19}$, a $G12V^{3-17}$, or a $G12V^{3-42}$ sequence. In some embodiments, the HLA-A2-restricted peptide comprises the amino acid sequence of any one of SEQ ID NOs: 1-8. In some embodiments, the mutated Ras antigen comprises an amino acid sequence with at least 90% similarity to any one of SEQ ID NOs: 1-8. In some embodiments, the mutated Ras antigen comprises an amino acid sequence from the N-terminal domain of the corresponding mutated K-Ras protein (e.g. K-Ras-G12D, K-Ras-G12V, K-Ras-G12C, K-Ras-G13D). In some embodiments, the mutated Ras antigen is one or more of a $G12D^{1-16}$, a $G12D^{2-19}$, a $G12D^{2-22}$, or a $G12D^{2-29}$, a $G12V^{1-16}$, a $G12V^{2-19}$, a $G12V^{3-17}$, or a $G12V^{3-42}$ antigen. In some embodiments, the N-terminal domain is identical in the three Ras isoforms of K-Ras, N-Ras and H-Ras. In some embodiments, wherein the mutated Ras antigen is a mutated K-Ras antigen, the mutated K-Ras antigen comprises an amino acid sequence from the N-terminal domain of the corresponding mutated K-Ras protein (e.g. K-Ras-G12D, K-Ras-G12V, K-Ras-G12C, K-Ras-G13D), which is the same as the amino acid sequence from the N-terminal domain of the corresponding mutated H-Ras protein (e.g. H-Ras-G12D, H-Ras-G12V, H-Ras-G12C, H-Ras-G13D) or mutated N-Ras protein (e.g. N-Ras-G12D, N-Ras-G12V, N-Ras-G12C, N-Ras-G13D). In some embodiments, the mutated Ras antigen comprises an amino acid sequence with at least 90% similarity to SEQ ID NO:1-8. In some embodiments, the mutated Ras antigen comprises an amino acid sequence with at least any one of: 80%, 85%, 90%, or 95%, similarity to any one of SEQ ID NOs: 1-8. In some embodiments, the mutated Ras antigen comprises an amino acid sequence with at least 90% similarity to SEQ ID NO:1. In some embodiments, the mutated Ras antigen comprises the amino acid sequence of SEQ ID NO:2. In a some embodiment, the mutated Ras antigen comprises the amino acid sequence of SEQ ID NO:3. In some embodiments, the mutated Ras antigen comprises the amino acid sequence of SEQ ID NO:4. In a some embodiments, the mutated Ras antigen comprises the amino acid sequence of SEQ ID NO: 5. In a some embodiments, the mutated Ras antigen comprises the amino acid sequence of SEQ ID NO:6. In a some embodiments, the mutated Ras antigen consists of the amino acid sequence of SEQ ID NO:7. In a some embodiments, the mutated Ras antigen consists of the amino acid sequence of SEQ ID NO:8. In some embodiments, the mutated Ras antigen comprises the amino acid sequence of any one of SEQ ID NOs: 9-15. In some embodiments, the mutated Ras antigen is a plurality of mutated Ras epitopes. In some embodiments, the mutated Ras antigen is a plurality of mutated Ras epitopes comprising at least one of the amino acid sequences of any one of SEQ ID NOs: 9-15. In some embodiments, the mutated Ras antigen comprises a plurality of Ras epitopes wherein the mutated Ras antigen comprises about 9 to about 200 amino acids. In some embodiments, the mutated Ras antigen is a plurality of antigens comprising at least one of the amino acid sequences of any one of SEQ ID NOs: 1-8. In some embodiments, the mutated Ras antigen comprises about 9 to about 200 amino acids. In some embodiments, the mutated Ras antigen is a plurality of antigens comprising 2, 3, 4, 5, 6, 7 or 8 of the amino acid sequences of any one of SEQ ID NOs: 1-8. In some embodiments, the plurality of antigens is contained within a pool of non-covalently linked peptides. In some embodiments, the plurality of antigens is contained within a pool of non-covalently linked peptides, wherein each peptide comprises no more than one antigen In some embodiments according to any one of the methods described herein, the nucleated cells (e.g., PBMCs) comprise a plurality of Ras antigens that comprise a plurality of immunogenic epitopes. In further embodiments, following administration to an individual of the nucleated cells comprising the plurality of antigens that comprise the plurality of immunogenic epitopes, none of the plurality of immunogenic epitopes decreases an immune response in the individual to any of the other immunogenic epitopes. In some embodiments, the Ras antigen is a polypeptide and the immunogenic epitope is an immunogenic peptide epitope. In some embodiments, the immunogenic peptide epitope is fused to an N-terminal flanking polypeptide and/or a C-terminal flanking polypeptide. In some embodiments, the mutant Ras antigen is a polypeptide comprising an immunogenic peptide epitope and one or more heterologous peptide sequences. In some embodiments, the mutant Ras antigen is a polypeptide comprising an immunogenic peptide epitope that is flanked on the N-terminus and/or the C-terminus by heterologous peptide sequences. In some embodiments, the flanking heterologous peptide sequences are derived from disease-associated immunogenic peptides. In some embodiments, the flanking heterologous peptide sequences are non-naturally occurring sequence. In some embodiments, the flanking heterologous peptide sequences are derived from an immunogenic synthetic long peptide (SLP). In some embodiments, the mutated Ras antigen is capable of being processed into an MHC class I-restricted peptide and/or an MHC class II-restricted peptide.

Methods of Generating Compositions of Nucleated Cells Comprising Mutated a Ras Antigen In some aspects, provided are methods for generating a composition of nucleated cells comprising a mutated Ras antigen, wherein the mutated Ras antigen is delivered to the nucleated cell intracellularly. In some embodiments, there is provided a method for generating a composition of nucleated cells comprising a mutated Ras-G12D antigen, wherein the mutated Ras-G12D antigen is delivered to the nucleated cell intracellularly. In some embodiments, there is provided a method for generating a composition of nucleated cells comprising a mutated Ras-G12V antigen, wherein the mutated Ras-G12V antigen is delivered to the nucleated cell intracellularly. In some embodiments, there is provided a method for generating a composition of nucleated cells comprising a mutated Ras-G12C antigen, wherein the mutated Ras-G12C antigen is delivered to the nucleated cell intracellularly. In some embodiments, there is provided a method for generating a composition of nucleated cells comprising a mutated Ras-G13D antigen, wherein the mutated Ras-G13D antigen is delivered to the nucleated cell intracellularly. In some embodiments, there is provided a method for generating a composition of nucleated cells comprising a mutated Ras antigen, wherein the mutated Ras antigen is delivered to the nucleated cell intracellularly, wherein the Ras antigen comprises the amino acid sequence of any one of SEQ ID NOs: 1-15. In some embodiments, there is provided a method for generating a composition of conditioned nucleated cells, wherein the nucleated cells comprise a mutated Ras antigen; wherein the mutated Ras antigen is delivered to the nucleated cell intracellularly.

In some aspects, provided are methods for generating a composition of nucleated cells comprising a mutated Ras antigen, wherein the mutated Ras antigen is delivered to the nucleated cell intracellularly my mechanical disruption of the nucleated cell membrane. In some embodiments, the mutated Ras antigen is delivered to the cell intracellularly by constriction mediated delivery; for example, by constriction mediated disruption of the membrane of the nucleated cell. In some embodiments, the mutated Ras antigen is a Ras G12D antigen, Ras G12V antigen, Ras G12C antigen, or Ras G13D antigen.

In some aspects, there is provided a method for generating a composition of nucleated cells comprising a mutated Ras antigen, comprising: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mutated Ras antigen to pass through to form a perturbed input nucleated cells; and b) incubating the perturbed input nucleated cells with the mutated Ras antigen for a sufficient time to allow the mutated Ras antigen to enter the perturbed input nucleated cells; thereby generating nucleated cells comprising the mutated Ras antigen. In some embodiments, the mutated Ras antigen is a mutated Ras antigen. In some embodiments, the mutated Ras antigen comprises the amino acid sequence of any one of SEQ ID NOs: 1-15. In some embodiments, the mutated Ras antigen comprises an amino acid sequence with at least 90% identity to any one of SEQ ID NOs: 1-15.

In some embodiments, there is provided a method for generating a composition comprising nucleated cells comprising a mutated Ras antigen, comprising: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for a nucleic acid encoding the mutated Ras antigen to pass through to form a perturbed input nucleated cells; and b) incubating the perturbed input nucleated cells with the nucleic acid encoding the mutated Ras antigen for a sufficient time to allow the nucleic acid encoding the mutated Ras antigen to enter the perturbed input nucleated cells, wherein the nucleic acid expressed the mutated Ras antigen; thereby generating nucleated cells comprising the mutated Ras antigen. In some embodiments, the mutated Ras antigen is a mutated Ras antigen. In some embodiments, the mutated Ras antigen comprises the amino acid sequence of any one of SEQ ID NOs: 1-15. In some embodiments, the mutated Ras antigen comprises an amino acid sequence with at least 90% identity to any one of SEQ ID NOs: 1-15.

In some aspects, there is provided a method for generating a composition comprising conditioned nucleated cells comprising a mutated Ras antigen, comprising: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mutated Ras antigen to pass through to form a perturbed input nucleated cells; b) incubating the perturbed input nucleated cells with the mutated Ras antigen for a sufficient time to allow the mutated Ras antigen to enter the perturbed input nucleated cells; thereby generating nucleated cells comprising the mutated Ras antigen; and c) incubating the nucleated cells with the adjuvant for a sufficient time for the nucleated cells to condition. In some aspects, there is provided a method for generating a composition comprising conditioned nucleated cells comprising a mutated Ras antigen, comprising: a) incubating the input nucleated cells with an adjuvant for a sufficient time for the nucleated cells to condition, thereby generating conditioned input nucleated cells; b) passing a cell suspension comprising the conditioned input nucleated cells through a cell-deforming constriction, wherein a diameter of the constriction is a function of a diameter of the conditioned input nucleated cells in the suspension, thereby causing perturbations of the conditioned input nucleated cells large enough for the mutated Ras antigen to pass through to form perturbed conditioned input nucleated cells; c) incubating the perturbed conditioned input nucleated cells with the mutated Ras antigen for a sufficient time to allow the mutated Ras antigen to enter the perturbed conditioned input nucleated cells; thereby generating conditioned nucleated cells comprising the mutated Ras antigen. In some embodiments, the mutated Ras antigen is a mutated Ras antigen. In some embodiments, the mutated Ras antigen comprises the amino acid sequence of any one of SEQ ID NOs: 1-15. In some embodiments, the mutated Ras antigen comprises an amino acid sequence with at least 90% identity to any one of SEQ ID NOs: 1-15.

In some aspects, there is provided a method for generating a composition comprising conditioned nucleated cells comprising a mutated Ras antigen, comprising: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for a nucleic acid encoding the mutated Ras antigen to pass through to form a perturbed input nucleated cells; b) incubating the perturbed input nucleated cells with the nucleic acid encoding the mutated Ras antigen for a sufficient time to allow the nucleic acid encoding the mutated Ras antigen to enter the perturbed input nucleated cells; thereby generating nucleated cells comprising the nucleic acid encoding mutated Ras antigen, wherein the nucleic acid encoding the mutated Ras antigen is expressed thereby generating a nucleated cell comprising a mutated Ras antigen; and c) incubating the nucleated cells with the adjuvant for the nucleated cells for a sufficient time to condition. In some aspects, there is provided a method for generating a composition comprising conditioned nucleated cells comprising a mutated Ras antigen, comprising: a) incubating the input nucleated cells with an adjuvant for a sufficient time for the nucleated cells to condition, thereby generating conditioned input nucleated cells; b) passing a cell suspension comprising the conditioned input nucleated cells through a cell-deforming constriction, wherein a diameter of the constriction is a function of a diameter of the conditioned input nucleated cells in the suspension, thereby causing perturbations of the conditioned input nucleated cells large enough for a nucleic acid encoding the mutated Ras antigen to pass through to form perturbed conditioned input nucleated cells; c) incubating the perturbed conditioned input nucleated cells with the nucleic acid encoding the mutated Ras antigen for a sufficient time to allow the nucleic acid encoding the mutated Ras antigen to enter the perturbed input nucleated cells; thereby generating conditioned nucleated cells comprising the nucleic acid encoding mutated Ras antigen, wherein the nucleic acid encoding the mutated Ras antigen is expressed thereby generating conditioned nucleated cells comprising a mutated Ras antigen. In some embodiments, the mutated Ras antigen is a mutated Ras antigen. In some embodiments, the mutated Ras antigen comprises the amino acid sequence of any one of SEQ ID NOs: 1-15. In some embodiments, the mutated Ras antigen comprises an amino acid sequence with at least 90% identity to any one of SEQ ID NOs: 1-15.

In some embodiments, the width of the constriction is about 10% to about 99% of the mean diameter of the input nucleated cells. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input nucleated cells having the smallest diameter within the population of nucleated cells. In some embodiments, the width of the constriction about 3 μm to about 5 μm, about 3 μm to about 3.5 μm, about 3.5 μm to about 4 μm, about 4 μm to about 4.5 μm, about 3.2 μm to about 3.8 μm, about 3.8 μm to about 4.3 μm, about 4.2 μm to about 6 μm, or about 4.2 μm to about 4.8 μm. In some embodiments, the width of the constriction is about 4.5 μm. In some embodiments, the width of the constriction is about or less than any one of 2 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, 10.5 μm, 11 μm, 11.5 μm, 12 μm, 12.5 μm, 13 μm, 13.5 μm, 14 μm, 14.5 μm or 15 μm. In some embodiments, the cell suspension comprising the input nucleated cells are passed through multiple constrictions wherein the multiple constrictions are arranged in series and/or in parallel. In some embodiments according to any one of the methods described herein, the nucleated cells are incubated with the adjuvant for a sufficient time for the nucleated cells to condition. In some embodiments, the nucleated cells are incubated with the adjuvant for about 1 to about 24 hours for the nucleated cells to condition. In some embodiments, the nucleated cells are incubated with the adjuvant for about 2 to about 10 hours for the nucleated cells to condition. In some embodiments, the nucleated cells are incubated with the adjuvant for about 3 to about 6 hours for the nucleated cells to condition. In some embodiments, the nucleated cells are incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the nucleated cells to condition. In some embodiments, the nucleated cells are incubated with the adjuvant for about 4 hours for the nucleated cells to condition. In some embodiments, the nucleated cells are conditioned before introducing the mutated Ras antigen or the nucleic acid encoding the mutated Ras antigen into the nucleated cells. In some embodiments, the nucleated cells are conditioned after introducing the mutated Ras antigen or the nucleic acid encoding the mutated Ras antigen into the nucleated cells. In some embodiments, the adjuvant used for conditioning is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist. In some embodiments, the adjuvant is a CpG oligodeoxynucleotide (ODN). In some embodiments, the adjuvant is CpG 7909.

In some embodiments, wherein the nucleated cells comprise B cells, one or more co-stimulatory molecules is upregulated in the B cells of the conditioned nucleated cells compared to the B cells of the unconditioned nucleated cells. In some embodiments, the nucleated cells are a plurality of peripheral blood mononuclear cells (PBMCs). In some embodiments, wherein the nucleated cells are a plurality of PBMCs, one or more co-stimulatory molecules is upregulated in the B cells of the conditioned plurality of PBMCs compared to the B cells of the unconditioned plurality of PBMCs. In some embodiments, the co-stimulatory molecule is CD80 and/or CD86. In some embodiments, the conditioned plurality of PBMCs has increased expression of one or more of IFN-γ, IL-6, MCP-1, MIP-1β, IP-10, or TNF-α compared to an unconditioned plurality of PBMCs. In some embodiments, the expression of one or more of IFN-γ, IL-6, MCP-1, MIP-1β, IP-10, or TNF-α is increased by more than about 1.2-fold, 1.5-fold, 1.8-fold, 2-fold, 3-fold, 4-fold, 5-fold, 8-fold, or more than 10-fold compared to an unconditioned plurality of PBMCs In some embodiments according to any one of the methods described herein, the nucleated cells are immune cells. In some embodiments, the nucleated cells are human cells. In some embodiments, the nucleated cells are human cells with a haplotype of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16. In some embodiments, the nucleated cells are a plurality of PBMCs. In some embodiments, the conditioned nucleated cells are a conditioned plurality of modified PBMCs. In some embodiments, the plurality of PBMCs comprises two or more of T cell, B cell, NK cell, monocytes, dendritic cells or NK-T cells. In some embodiments, the nucleated cells are one or more of T cells, B cells, NK cells, monocytes, dendritic cells and/or NK-T cells.

In some embodiments, the plurality of PBMCs are further modified to increase expression of one or more of co-stimulatory molecules. In some embodiments, the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112. In some embodiments, the plurality of PBMCs are further modified to increase expression of one or more cytokines. In some embodiments, the cytokine is IL-15, IL-12, IL-2, IL-10, IFN-α, or IL 21.

In some embodiments, the mutated Ras antigen is a pool of multiple polypeptides that elicit a response against the same and or different mutated Ras antigens. In some embodiments, the mutated Ras antigen is a polypeptide comprising one or more antigenic mutated Ras epitope and one or more heterologous peptide sequences. In some embodiments, the mutated Ras antigen complexes with other antigens or with an adjuvant. In some embodiments, the mutated Ras antigen comprises a G12D mutation, a G12V mutation, a G12C mutation or a G13D mutation. In some embodiments, the mutated Ras antigen is a mutated K-Ras antigen, the mutated K-Ras antigen comprises an amino acid sequence from the N-terminal domain of the corresponding mutated K-Ras protein (e.g. K-Ras-G12D, K-Ras-G12V, K-Ras-G12C, K-Ras-G13D), which is the same as the amino acid sequence from the N-terminal domain of the corresponding mutated H-Ras protein (e.g. H-Ras-G12D, H-Ras-G12V, H-Ras-G12C, H-Ras-G13D) or mutated N-Ras protein (e.g. N-Ras-G12D, N-Ras-G12V, N-Ras-G12C, N-Ras-G13D). In some embodiments, the mutated Ras antigen is a polypeptide comprising one or more antigenic mutated Ras epitopes that is flanked on the N-terminus and/or the C-terminus by one or more heterologous peptide sequences. In some embodiments, the mutated Ras antigen is a polypeptide comprising one or more antigenic mutated Ras epitopes that is not flanked on the N-terminus and/or the C-terminus by one or more heterologous peptide sequences. In some embodiments, the mutated Ras antigen is one or more of a $G12D^{1-16}$, a $G12D^{2-19}$, a $G12D^{2-22}$, $G12D^{2-29}$, a $G12V^{1-16}$, a $G12V^{2-19}$, a $G12V^{3-17}$, or a $G12V^{3-42}$ antigen. In some embodiments, the mutated Ras antigen comprises an amino acid sequence with at least 90% similarity to any one of SEQ ID NOs1-8. In some embodiments, the mutated Ras antigen comprises an amino acid sequence with at least any one of: 80%, 85%, 90%, or 95% similarity to any one of SEQ ID NOs1-8. In some embodiments, the mutated Ras antigen comprises an amino acid sequence of SEQ ID NOs: 1-8. In some embodiments, the mutated Ras antigen comprises an amino acid sequence with at least 90% similarity to any one of SEQ ID NOs: 9-15. In some embodiments, the mutated Ras antigen comprises an amino acid sequence with at least any one of: 90 similarity to any one of SEQ ID NOs: 9-15. In some embodiments, the mutated Ras antigen comprises an amino acid sequence of SEQ ID NOs: 9-15. In some embodiments, the mutated Ras antigen is capable of being processed into an MHC class I-restricted peptide. In some embodiments, the mutated Ras antigen is capable of being processed into an MHC class II-restricted peptide.

In some embodiments, the composition further comprises an adjuvant. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist. In some embodiments, the adjuvant is a CpG oligodeoxynucleotide. In some embodiments, the adjuvant is CpG 7909.

Compositions of Nucleated Cells Comprising Mutated Ras Antigen

In some aspects, provided are compositions of nucleated cells comprising a mutated Ras antigen, wherein the mutated Ras antigen is delivered to the nucleated cell intracellularly. In some embodiments, there is provided a composition of nucleated cells comprising a mutated Ras-G12D antigen, wherein the mutated Ras-G12D antigen is delivered to the nucleated cell intracellularly. In some embodiments, there is provided a composition of nucleated cells comprising a mutated Ras-G12V antigen, wherein the mutated Ras-G12V antigen is delivered to the nucleated cell intracellularly. In some embodiments, there is provided a composition of nucleated cells comprising a mutated Ras-G12C antigen, wherein the mutated Ras-G12C antigen is delivered to the nucleated cell intracellularly. In some embodiments, there is provided a composition of nucleated cells comprising a mutated Ras-G13D antigen, wherein the mutated Ras-G13D antigen is delivered to the nucleated cell intracellularly. In some embodiments, there is provided a composition of nucleated cells comprising a mutated Ras antigen, wherein the mutated Ras antigen is delivered to the nucleated cell intracellularly, wherein the Ras antigen comprises the amino acid sequence of any one of SEQ ID NOs: 1-8. In some embodiments, there is provided a composition of comprising conditioned nucleated cells, wherein the nucleated cells comprise a mutated Ras antigen; wherein the mutated Ras antigen is delivered to the nucleated cell intracellularly.

In some aspects, there is provided a composition of nucleated cells comprising a mutated Ras antigen, wherein the nucleated cells comprising the mutated Ras antigen are prepared by: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mutated Ras antigen to pass through to form a perturbed input nucleated cells; and b) incubating the perturbed input nucleated cells with the mutated Ras antigen for a sufficient time to allow the mutated Ras antigen to enter the perturbed input nucleated cells; thereby generating nucleated cells comprising the mutated Ras antigen. In some embodiments, the mutated Ras antigen comprises the amino acid sequence of any one of SEQ ID NOs: 1-15. In some embodiments, the mutated Ras antigen comprises an amino acid sequence with at least 90% identity to any one of SEQ ID NOs: 1-15.

In some embodiments, there is provided a composition comprising nucleated cells comprising a mutated Ras antigen, wherein the nucleated cells comprising the mutated Ras antigen are prepared by: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for a nucleic acid encoding the mutated Ras antigen to pass through to form a perturbed input nucleated cells; and b) incubating the perturbed input nucleated cells with the nucleic acid encoding the mutated Ras antigen for a sufficient time to allow the nucleic acid encoding the mutated Ras antigen to enter the perturbed input nucleated cells, wherein the nucleic acid expressed the mutated Ras antigen; thereby generating nucleated cells comprising the mutated Ras antigen. In some embodiments, the mutated Ras antigen comprises the amino acid sequence of any one of SEQ ID NOs: 1-15 In some embodiments, the mutated Ras antigen comprises an amino acid sequence with at least 90% identity to any one of SEQ ID NOs: 1-15

In some aspects, there is provided a composition comprising conditioned nucleated cells comprising a mutated Ras antigen, wherein the conditioned nucleated cells comprising the mutated Ras antigen are prepared by: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mutated Ras antigen to pass through to form a perturbed input nucleated cells; b) incubating the perturbed input nucleated cells with the mutated Ras antigen for a sufficient time to allow the mutated Ras antigen to enter the perturbed input nucleated cells; thereby generating nucleated cells comprising the mutated Ras antigen; and c) incubating the nucleated cells with the adjuvant for a sufficient time for the nucleated cells to condition. In some aspects, there is provided a composition comprising conditioned nucleated cells comprising a mutated Ras antigen, wherein the conditioned nucleated cells comprising the mutated Ras antigen are prepared by: a) incubating the input nucleated cells with an adjuvant for a sufficient time for the nucleated cells to condition, thereby generating conditioned input nucleated cells; b) passing a cell suspension comprising the conditioned input nucleated cells through a cell-deforming constriction, wherein a diameter of the constriction is a function of a diameter of the conditioned input nucleated cells in the suspension, thereby causing perturbations of the conditioned input nucleated cells large enough for the mutated Ras antigen to pass through to form perturbed conditioned input nucleated cells; c) incubating the perturbed conditioned input nucleated cells with the mutated Ras antigen for a sufficient time to allow the mutated Ras antigen to enter the perturbed conditioned input nucleated cells; thereby generating conditioned nucleated cells comprising the mutated Ras antigen. In some embodiments, the mutated Ras antigen comprises the amino acid sequence of any one of SEQ ID NOs: 1-15. In some embodiments, the mutated Ras antigen comprises an amino acid sequence with at least 90% identity to any one of SEQ ID NOs: 1-15.

In some aspects, there is provided a composition comprising conditioned nucleated cells comprising a mutated Ras antigen, wherein the conditioned nucleated cells comprising the mutated Ras antigen are prepared by: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for a nucleic acid encoding the mutated Ras antigen to pass through to form a perturbed input nucleated cells; b) incubating the perturbed input nucleated cells with the nucleic acid encoding the mutated Ras antigen for a sufficient time to allow the nucleic acid encoding the mutated Ras antigen to enter the perturbed input nucleated cells; thereby generating nucleated cells comprising the nucleic acid encoding mutated Ras antigen, wherein the nucleic acid encoding the mutated Ras antigen is expressed thereby generating a nucleated cell comprising a mutated Ras antigen; and c) incubating the nucleated cells with the adjuvant for the nucleated cells for a sufficient time to condition. In some aspects, there is provided a composition comprising conditioned nucleated cells comprising a mutated Ras antigen, wherein the conditioned nucleated cells comprising the mutated Ras antigen are prepared by: a) incubating the input nucleated cells with an adjuvant for a sufficient time for the nucleated cells to condition, thereby generating conditioned input nucleated cells; b) passing a cell suspension comprising the conditioned input nucleated cells through a cell-deforming constriction, wherein a diameter of the constriction is a function of a diameter of the conditioned input nucleated cells in the suspension, thereby causing perturbations of the conditioned input nucleated cells large enough for a nucleic acid encoding the mutated Ras antigen to pass through to form perturbed conditioned input nucleated cells; c) incubating the perturbed conditioned input nucleated cells with the nucleic acid encoding the mutated Ras antigen for a sufficient time to allow the nucleic acid encoding the mutated Ras antigen to enter the perturbed input nucleated cells; thereby generating conditioned nucleated cells comprising the nucleic acid encoding mutated Ras antigen, wherein the nucleic acid encoding the mutated Ras antigen is expressed thereby generating conditioned nucleated cells comprising a mutated Ras antigen. In some embodiments, the mutated Ras antigen comprises the amino acid sequence of any one of SEQ ID NOs: 1-15. In some embodiments, the mutated Ras antigen comprises an amino acid sequence with at least 90% identity to any one of SEQ ID NOs: 1-15.

In some embodiments, there is provided the use of a composition for stimulating an immune response to mutated Ras protein in an individual, wherein the composition comprises an effective amount of any one of the compositions comprising nucleated cells comprising a mutated antigens described herein. In some embodiments, there is provided a composition for reducing tumor growth, wherein the composition comprises an effective amount of any one of the compositions comprising nucleated cells comprising a mutated antigen described herein. In some embodiments, the individual has cancer. In some embodiments, there is provided a composition for treating cancer in an individual, wherein the composition comprises an effective amount of any one of the compositions comprising nucleated cells comprising a mutated antigen described herein. In some embodiments, the cancer is a pancreatic cancer, a colon cancer, a small intestine cancer, a biliary tract cancer, an endometrial cancer, a lung cancer, a skin cancer, an ovarian cancer, a stomach cancer, an esophageal cancer, a cervical cancer or a urinary tract cancer.

In some embodiments, the width of the constriction is about 10% to about 99% of the mean diameter of the input nucleated cells. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input nucleated cells having the smallest diameter within the population of nucleated cells. In some embodiments, the width of the constriction about 3 μm to about 5 μm, about 3 μm to about 3.5 μm, about 3.5 μm to about 4 μm, about 4 μm to about 4.5 μm, about 3.2 μm to about 3.8 μm, about 3.8 μm to about 4.3 μm, about 4.2 μm to about 6 μm, or about 4.2 μm to about 4.8 μm. In some embodiments, the width of the constriction is about 4.5 μm. In some embodiments, the width of the constriction is about or less than any one of 2 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, 10.5 μm, 11 μm, 11.5 μm, 12 μm, 12.5 μm, 13 μm, 13.5 μm, 14 μm, 14.5 μm or 15 μm. In some embodiments, the cell suspension comprising the input nucleated cells are passed through multiple constrictions wherein the multiple constrictions are arranged in series and/or in parallel.

In some embodiments according to any one of the compositions described herein, the nucleated cells are incubated with the adjuvant for a sufficient time for the nucleated cells to condition. In some embodiments, the nucleated cells are incubated with the adjuvant for about 1 to about 24 hours for the nucleated cells to condition. In some embodiments, the nucleated cells are incubated with the adjuvant for about 2 to about 10 hours for the nucleated cells to condition. In some embodiments, the nucleated cells are incubated with the adjuvant for about 3 to about 6 hours for the nucleated cells to condition. In some embodiments, the nucleated cells are incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the nucleated cells to condition. In some embodiments, the nucleated cells are incubated with the adjuvant for about 4 hours for the nucleated cells to condition. In some embodiments, the nucleated cells are conditioned before introducing the mutated Ras antigen or the nucleic acid encoding the mutated Ras antigen into the nucleated cells. In some embodiments, the nucleated cells are condition/ned after introducing the mutated Ras antigen or the nucleic acid encoding the mutated Ras antigen into the nucleated cells. In some embodiments, the adjuvant used for conditioning is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist. In some embodiments, the adjuvant is a CpG oligodeoxynucleotide (ODN). In some embodiments, the adjuvant is CpG 7909.

In some embodiments, wherein the nucleated cells comprise B cells, one or more co-stimulatory molecules is upregulated in the B cells of the conditioned nucleated cells compared to the B cells of the unconditioned nucleated cells. In some embodiments, the nucleated cells are a plurality of peripheral blood mononuclear cells (PBMCs). In some embodiments, wherein the nucleated cells are a plurality of PBMCs, one or more co-stimulatory molecules is upregulated in the B cells of the conditioned plurality of PBMCs compared to the B cells of the unconditioned plurality of PBMCs. In some embodiments, the co-stimulatory molecule is CD80 and/or CD86. In some embodiments, the conditioned plurality of PBMCs has increased expression of one or more of IFN-γ, IL-6, MCP-1, MIP-1β, IP-10, or TNF-α compared to an unconditioned plurality of PBMCs. In some embodiments, the expression of one or more of IFN-γ, IL-6, MCP-1, MIP-1β, IP-10, or TNF-α is increased by more than about 1.2-fold, 1.5-fold, 1.8-fold, 2-fold, 3-fold, 4-fold, 5-fold, 8-fold, or more than 10-fold compared to an unconditioned plurality of PBMCs In some embodiments according to any one of the compositions described herein, the nucleated cells are immune cells. In some embodiments, the nucleated cells are human cells. In some embodiments, the nucleated cells are human cells with a haplotype of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16. In some embodiments, the nucleated cells are a plurality of PBMCs. In some embodiments, the conditioned nucleated cells are a conditioned plurality of modified PBMCs. In some embodiments, the plurality of PBMCs comprises two or more of T cell, B cell, NK cell, monocytes, dendritic cells or NK-T cells. In some embodiments, the nucleated cells are one or more of T cells, B cells, NK cells, monocytes, dendritic cells and/or NK-T cells.

In some embodiments, the plurality of PBMCs are further modified to increase expression of one or more of co-stimulatory molecules. In some embodiments, the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112. In some embodiments, the plurality of PBMCs are further modified to increase expression of one or more cytokines. In some embodiments, the cytokine is IL-15, IL-12, IL-2, IFN-α, or IL 21.

In some embodiments, the mutated Ras antigen is a pool of multiple polypeptides that elicit a response against the same and or different mutated Ras antigens. In some embodiments, the mutated Ras antigen is a polypeptide comprising one or more antigenic mutated Ras epitope and one or more heterologous peptide sequences. In some embodiments, the mutated Ras antigen complexes with other antigens or with an adjuvant. In some embodiments, the mutated Ras antigen comprises a G12D mutation, a G12V mutation, a G12C mutation or a G13D mutation. In some embodiments, the mutated Ras antigen is a polypeptide comprising one or more antigenic mutated Ras epitopes that is flanked on the N-terminus and/or the C-terminus by one or more heterologous peptide sequences. In some embodiments, the mutated Ras antigen is a polypeptide comprising one or more antigenic mutated Ras epitopes that is not flanked on the N-terminus and/or the C-terminus by one or more heterologous peptide sequences. In some embodiments, the mutated Ras antigen is one or more of a $G12D^{1-16}$, a $G12D^{2-19}$, a $G12D^{2-22}$, a $G12D^{2-29}$, a $G12V^{1-16}$, a $G12V^{2-19}$, a $G12V^{3-17}$, or a $G12V^{3-42}$ antigen. In some embodiments, the mutated Ras antigen comprises an amino acid sequence with at least 90% similarity to any one of SEQ ID NOs: 1-8. In some embodiments, the mutated Ras antigen comprises an amino acid sequence with at least any one of: 80%, 85%, 90%, or 95% similarity to any one of SEQ ID NOs: 1-8. In some embodiments, the mutated Ras antigen comprises an amino acid sequence of SEQ ID NOs: 1-8. In some embodiments, the mutated Ras antigen comprises an amino acid sequence with at least 90% similarity to any one of SEQ ID NOs: 9-15. In some embodiments, the mutated Ras antigen comprises an amino acid sequence of SEQ ID NOs: 9-15. In some embodiments, the mutated Ras antigen is capable of being processed into an MHC class I-restricted peptide. In some embodiments, the mutated Ras antigen is capable of being processed into an MHC class II-restricted peptide.

In some embodiments, the composition further comprises an adjuvant. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist. In some embodiments, the adjuvant is a CpG oligodeoxynucleotide. In some embodiments, the adjuvant is CpG 7909.

In some embodiments, there is provided a composition for stimulating an immune response to mutated Ras protein in an individual, wherein the composition comprises an effective amount of any one of the compositions comprising nucleated cells comprising a mutated antigens described herein.

Constituent Cells within the Input Nucleated Cells

In some embodiments, the methods disclosed herein provide for the administration to an individual in need thereof an effective amount of compositions of nucleated cells comprising a mutated Ras antigen, wherein the mutated Ras antigen is delivered intracellularly. In some embodiments, the composition of nucleated cells is a composition of immune cells. In some embodiments, the composition of nucleated cells comprises a plurality of PBMCs. In some embodiments, the nucleated cells are one or more of T cells, B cells, NK cells, monocytes, dendritic cells and/or NK-T cells.

In a particular embodiment of the invention, the nucleated cells comprising a mutated Ras antigen of the composition are PBMCs. As used herein, PBMCs may be isolated by apheresis such as leukapheresis from whole blood obtained from an individual. Also provided are PBMC compositions reconstituted by mixing different pools of PBMCs from the same individual or different individuals. In other examples, PBMCs may also be reconstituted by mixing different populations of cells into a mixed cell composition with a generated profile. In some embodiments, the populations of cells used for reconstituting PBMCs are mixed populations of cells (such as a mixture of one or more of T cells, B cells, NK cells or monocytes). In some embodiments, the populations of cells used for reconstituting PBMCs are purified populations of cells (such as purified T cells, B cells, NK cells or monocytes). In additional examples, the different populations of cells used in reconstituting a PBMC composition can be isolated from the same individual (e.g. autologous) or isolated from different individuals (e.g. allogenic and/or heterologous).

Therefore, in some embodiments according to the methods described herein, the plurality of PBMCs comprises one or more of T cells, B cells, NK cells, monocytes, dendritic cells or NK-T cells. In some embodiments, the plurality of PBMCs comprises T cells, B cells, NK cells, monocytes, dendritic cells or NK-T cells. In some embodiments, the plurality of PBMCs comprises one or more of CD3+ T cells, CD20+ B cells, CD14+ monocytes, CD56+NK cells. In some embodiments, the plurality of PBMCs comprises T cells, B cells, NK cells and monocytes, and the ratio of T cells, B cells, NK cells and monocytes to the total number of PBMCs in the plurality of PBMCs is essentially the same as the ratio of T cells, B cells, NK cells and monocytes to the total number of PBMCs in whole blood. In some embodiments, the plurality of PBMCs comprises T cells, B cells, NK cells and monocytes, and the ratio of T cells, B cells, NK cells and monocytes to the total number of PBMCs in the plurality of PBMCs is essentially the same as the ratio of T cells, B cells, NK cells and monocytes to the total number of PBMCs in a leukapheresis product from whole blood. In some embodiments, the plurality of PBMCs comprises T cells, B cells, NK cells and monocytes, and the ratio of T cells, B cells, NK cells and monocytes to the total number of PBMCs in the plurality of PBMCs differs by not more than any one of 1%, 2%, 5%, 10% 15%, 20%, 25%, 30%, 40%, or 50% from the ratio of T cells, B cells, NK cells and monocytes to the total number of PBMCs in whole blood. In some embodiments, the plurality of PBMCs comprises T cells, B cells, NK cells and monocytes, and the ratio of T cells, B cells, NK cells and monocytes to the total number of PBMCs in the plurality of PBMCs differs by not more than any one of 10% from the ratio of T cells, B cells, NK cells and monocytes to the total number of PBMCs in whole blood. In some embodiments, the plurality of PBMCs comprises T cells, B cells, NK cells and monocytes, and the ratio of T cells, B cells, NK cells and monocytes to the total number of PBMCs in the plurality of PBMCs differs by not more than any one of 1%, 2%, 5%, 10% 15%, 20%, 25%, 30%, 40%, or 50% from the ratio of T cells, B cells, NK cells and monocytes to the total number of PBMCs in a leukapheresis product from whole blood. In some embodiments, the plurality of PBMCs comprises T cells, B cells, NK cells and monocytes, and the ratio of T cells, B cells, NK cells and monocytes to the total number of PBMCs in the plurality of PBMCs differs by not more than any one of 10% from the ratio of T cells, B cells, NK cells and monocytes to the total number of PBMCs in a leukapheresis product from whole blood.

In some embodiments according to the methods described herein, about 25% to about 70% of the modified PBMCs are T cells. In some embodiments, about 2.5% to about 14% of the modified PBMCs are B cells. In some embodiments, about 3.5% to about 35% of the modified PBMCs are NK cells. In some embodiments, about 4% to about 25% of the modified PBMCs are NK cells.

In some embodiments according to the methods described herein, at least about any one of 15%, 20%, 25%, 30%, 35%, 40%, 45%, 50%, 55%, 60%, 65%, 70%, or 75% of the PBMCs are T cells. In some embodiments, at least about 25% of the PBMCs are T cells. In some embodiments, at least about any one of 0.5%, 1%, 1.5%, 2%, 2.5%, 3%, 4%, 5%, 6%, 7%, 7.5%, 8%, 9%, 10%, 11%, 12%, 13%, 14%, 15%, 16%, 17%, 18%, 19%, 20%, 25%, or 30% of the PBMCs are B cells. In some embodiments, at least about 2.5% of the PBMCs are B cells. In some embodiments, at least about any one of 0.5%, 1%, 1.5%, 2%, 2.5%, 3%, 4%, 5%, 6%, 7%, 7.5%, 8%, 9%, 10%, 11%, 12%, 13%, 14%, 15%, 16%, 17%, 18%, 19%, 20%, 25%, or 30% of the PBMCs are NK cells. In some embodiments, at least about 3.5% of the PBMCs are NK cells. In some embodiments, at least about any one of 1%, 2%, 3%, 4%, 5%, 6%, 7%, 8%, 9%, 10%, 12%, 14%, 16%, 18%, 20%, 25%, 30%, 35% or 40% of the PBMCs are monocytes. In some embodiments, at least about 4% of the PBMCs are monocytes. In some embodiments, at least about 25% of the PBMCs are T cells; at least about 2.5% of the PBMCs are B cells; at least about 3.5% of the PBMCs are NK cells; and at least about 4% of the PBMCs are monocytes.

In some embodiments according to the methods described herein, not more than about any one of 40%, 45%, 50%, 55%, 60%, 65%, 70%, 75%, 80%, 85%, or 90% of the PBMCs are T cells. In some embodiments, not more than about 70% of the PBMCs are T cells. In some embodiments, not more than about any one of 5%, 10%, 12%, 14%, 16%, 18%, 20%, 22%, 25%, 30%, 35%, 40%, or 50% of the PBMCs are B cells. In some embodiments, not more than about 14% of the PBMCs are B cells. In some embodiments, not more than about any one of 10%, 15%, 20%, 25%, 30%, 35%, 40%, 45%, 50% or 60% of the PBMCs are NK cells. In some embodiments, not more than about 35% of the PBMCs are NK cells. In some embodiments, not more than about any one of 5%, 10%, 12%, 14%, 16%, 18%, 20%, 22%, 25%, 30%, 35%, 40%, or 50% of the PBMCs are monocytes. In some embodiments, not more than about 4% of the PBMCs are monocytes. In some embodiments, not more than about 25% of the PBMCs are T cells; not more than about 2.5% of the PBMCs are B cells; not more than about 3.5% of the PBMCs are NK cells; and not more than about 4% of the PBMCs are monocytes.

In some embodiments according to the methods described herein, about any one of 20% to 25%, 25% to 30%, 30% to 35%, 35% to 40%, 40% to 45%, 45% to 50%, 50% to 55%, 55% to 60%, 60% to 65%, 65% to 70%, or 70% to 75% of the modified PBMCs are T cells. In some embodiments, about 25% to about 70% of the modified PBMCs are T cells. In some embodiments, about any one of 1% to 2.5%, 2.5% to 4%, 4% to 6%, 6% to 8%, 8% to 10%, 10% to 12%, 12% to 14%, 14% to 16%, 16% to 20% or 20% to 25% of the modified PBMCs are B cells. In some embodiments, about 2.5% to about 14% of the modified PBMCs are B cells. In some embodiments, about any one of 1% to 2%, 2% to 3.5%, 3.5% to 5%, 5% to 8%, 8% to 10%, 10% to 12%, 12% to 14%, 14% to 16%, 16% to 20%, 20% to 25%, 25% to 30%, 30% to 35%, or 35% to 40% of the modified PBMCs are NK cells. In some embodiments, about 3.5% to about 35% of the modified PBMCs are NK cells. In some embodiments, about any one of 2% to 4%, 4% to 6%, 6% to 8%, 8% to 10%, 10% to 12%, 12% to 14%, 14% to 16%, 16% to 20%, 20% to 25%, 25% to 30%, 30% to 35%, or 35% to 40% of the modified PBMCs are monocytes. In some embodiments, about 4% to about 25% of the modified PBMCs are monocytes. In some embodiments, about 25% to about 70% of the modified PBMCs are T cells, about 2.5% to about 14% of the modified PBMCs are B cells, about 3.5% to about 35% of the modified PBMCs are NK cells, and about 4% to about 25% of the modified PBMCs are NK cells.

As used herein, PBMCs can also be generated after manipulating the composition of a mixed cell population of mononuclear blood cells (such as lymphocytes and monocytes). In some instances, the PBMCs are generated after reducing (such as depleting) certain subpopulations (such as B cells) within a mixed cell population of mononuclear blood cells. The composition in a mixed cell population of mononuclear blood cells in an individual can be manipulated to make the cell population more closely resemble a leukapheresis product from whole blood in the same individual. In other examples, the composition in a mixed cell population of mononuclear blood cells (for example, mouse splenocytes) can also be manipulated to make the cell population more closely resemble human PBMCs isolated from a leukapheresis product from human whole blood.

In some embodiments of the invention, the composition of nucleated cells comprising a mutated Ras antigen is a population of cells found in PBMCs. In some embodiments, the composition of nucleated cells comprising a mutated Ras antigen comprises one or more of T cells, B cells, NK cells, monocytes, dendritic cells or NK-T cells. In some embodiments, the composition of nucleated cells comprising a mutated Ras antigen comprises one or more of CD3+ T cells, CD20+ B cells, CD14+ monocytes, CD56+NK cells. In some embodiments, the composition of nucleated cells comprising a mutated Ras antigen comprises at least about any of 70%, 75%, 80%, 85%, 90%, 95%, or 99% T cells. In some embodiments, the composition of nucleated cells comprising a mutated Ras antigen comprises 100% T cells. In some embodiments, the composition of nucleated cells comprising a mutated Ras antigen comprises at least about any of 70%, 75%, 80%, 85%, 90%, 95%, or 99% B cells. In some embodiments, the composition of nucleated cells comprising an mutated Ras antigen comprises 100% B cells. In some embodiments, the composition of nucleated cells comprising a mutated Ras antigen comprises at least about any of 70%, 75%, 80%, 85%, 90%, 95%, or 99% NK cells. In some embodiments, the composition of nucleated cells comprising a mutated Ras antigen comprises 100% NK cells. In some embodiments, the composition of nucleated cells comprising a mutated Ras antigen comprises at least about any of 70%, 75%, 80%, 85%, 90%, 95%, or 99% monocytes. In some embodiments, the composition of nucleated cells comprising a Ras antigen comprises 100% monocytes. In some embodiments, the composition of nucleated cells comprising a mutated Ras antigen comprises at least about any of 70%, 75%, 80%, 85%, 90%, 95%, or 99% dendritic cells. In some embodiments, the composition of nucleated cells comprising a Ras antigen comprises 100% dendritic cells. In some embodiments, the composition of nucleated cells comprising a mutated Ras antigen comprises at least about any of 70%, 75%, 80%, 85%, 90%, 95%, or 99% NK-T cells. In some embodiments, the composition of nucleated cells comprising a mutated Ras antigen comprises 100% NK-T cells.

Further Modifications of Nucleated Cells Comprising Mutated Ras Antigen

In some embodiments according to any one of the methods described herein, the composition of nucleated cells (e.g., PBMCs) further comprises an agent that enhances the viability and/or function of the nucleated cells as compared to a corresponding composition of nucleated cells that does not comprise the agent. In some embodiments, the composition of nucleated cells further comprises an agent that enhances the viability and/or function of the nucleated cells upon freeze-thaw cycle as compared to a corresponding composition of nucleated cells that does not comprise the agent. In some embodiments, the agent is a cryopreservation agent and/or a hypothermic preservation agent. In some embodiments, the cryopreservation agent nor the hypothermic preservation agent cause not more than 10% or 20% of cell death in a composition of nucleated cells comprising the agent compared to a corresponding composition of nucleated cells that does not comprise the agent before any freeze-thaw cycles. In some embodiments, at least about 70%, about 80%, or about 90% of the nucleated cells are viable after up to 1, 2, 3, 4, 5 freeze-thaw cycles. In some embodiments, the agent is a compound that enhances endocytosis, a stabilizing agent or a co-factor. In some embodiments, the agent is albumin. In some embodiments, the albumin is mouse, bovine, or human albumin. In some embodiments, the agent is human albumin. In some embodiments, the agent is one or more of: a divalent metal cation, glucose, ATP, potassium, glycerol, trehalose, D-sucrose, PEG1500, L-arginine, L-glutamine, or EDTA. In some embodiments, the divalent metal cation is one more of Mg2+, Zn2+ or Ca2+. In some embodiments, the agent is one or more of: sodium pyruvate, adenine, trehalose, dextrose, mannose, sucrose, human serum albumin (HSA), DMSO, HEPES, glycerol, glutathione, inosine, dibasic sodium phosphate, monobasic sodium phosphate, sodium metal ions, potassium metal ions, magnesium metal ions, chloride, acetate, gluoconate, sucrose, potassium hydroxide, or sodium hydroxide. In some embodiments, the agent is one or more of: Sodium pyruvate, adenine, Rejuvesol®, trehalose, dextrose, mannose, sucrose, human serum albumin (HSA), PlasmaLyte®, DMSO, Cryostor® CS2, Cryostor® CS5, Cryostor® CS10, Cryostor® CS15, HEPES, glycerol, glutathione, HypoThermosol®.

In some embodiments according to any one of the methods described herein, the composition of nucleated cells comprises a plurality of modified PBMCs that are further modified to increase expression of one or more of co-stimulatory molecules. In some embodiments, the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112. In some embodiments, the plurality of modified PBMCs comprises a nucleic acid that results in increased expression of the one or more co-stimulatory molecules. In some embodiments, the plurality of modified PBMCs comprises an mRNA that results in increased expression of the one or more co-stimulatory molecules. In some embodiments, the co-stimulatory molecule is a Signal 2 effector in stimulating T cell activation.

In some embodiments according to any one of the methods described herein, the modified PBMCs are further modified to increase expression of one or more cytokines. In some embodiments, the cytokine is one or more of IL-2, IL-12, IL-21, or IFNα2. In some embodiments, the plurality of modified PBMCs comprises a nucleic acid that results in increased expression and/or secretion of the one or more cytokines. In some embodiments, the cytokine is a Signal 3 effector in stimulating T cell activation.

In some embodiments according to any one of the methods described herein, at least one cell in the plurality of modified PBMCs is positive for expression of HLA-A2. In some embodiments, the modified PBMCs comprise a further modification to modulate MHC class I expression. In some embodiments, the modified PBMCs comprise a further modification to modulate expression of HLA-A02 MHC class I. In some embodiments, the modified PBMCs comprise a further modification to modulate expression of HLA-A*11 MHC class I. In some embodiments, the modified PBMCs comprise a further modification to modulate expression of HLA-B*07 MHC class I. In some embodiments, the modified PBMCs comprise a further modification to modulate expression of HLA-C*08 MHC class I. Agents that can lead to the upregulation of HLA expression include, but are not limited to, IFNγ, IFNα, IFNβ and radiation. In some embodiments, the modified PBMCs comprise a further modification to modulate MHC class II expression. In some embodiments, an innate immune response mounted in an individual in response to administration, in an allogeneic context, of the modified PBMCs is reduced compared to an innate immune response mounted in an individual in response to administration, in an allogeneic context, of corresponding modified PBMCs that do not comprise the further modification. In some embodiments, the circulating half-life of the modified PBMCs in an individual to which they were administered is increased compared to the circulating half-life of corresponding modified PBMCs that do not comprise the further modification in an individual to which they were administered. In some embodiments, the circulating half-life of the modified PBMCs in an individual to which they were administered is increased by about any one of 10%, 25%, 50%, 75%, 100%, 2-fold, 3-fold, 4-fold, 5-fold, 10-fold, 25-fold, 50-fold, 100-fold, 200-fold, or 500-fold or more compared to the circulating half-life of corresponding modified PBMCs that do not comprise the further modification in an individual to which they were administered. In some embodiments, the circulating half-life of the modified PBMCs in an individual to which they were administered is essentially the same as the circulating half-life of corresponding modified PBMCs that do not comprise the further modification in an individual to which they were administered.

In some embodiments according to any one of the methods described herein, the process further comprises a step of incubating the composition of nucleated cells with an agent that enhances the viability and/or function of the nucleated cells compared to corresponding nucleated cells prepared without the further incubation step.

Adjuvants

As used herein, the term "adjuvant" can refer to a substance which either directly or indirectly modulates and/or engenders an immune response. In some embodiments of the invention, an adjuvant is used to condition a population of nucleated cells such as a population of PBMCs (i.e, the cells are incubated with an adjuvant prior to administration to an individual). In some instances, the adjuvant is administered in conjunction with a mutated Ras antigen to effect enhancement of an immune response to the mutated Ras antigen as compared to mutated Ras antigen alone. Therefore, adjuvants can be used to boost elicitation of an immune cell response (e.g. T cell response) to a mutated Ras antigen. Exemplary adjuvants include, without limitation, stimulator of interferon genes (STING) agonists, retinoic acid-inducible gene I (RIG-I) agonists, and agonists for TLR3, TLR4, TLR7, TLR8 and/or TLR9. Exemplary adjuvants include, without limitation, CpG ODN, interferon-α (IFN-α), polyinosinic: polycytidylic acid (polyI:C), imiquimod (R837), resiquimod (R848), or lipopolysaccharide (LPS). In some embodiments, the adjuvant is CpG ODN, LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist. In particular embodiments, the adjuvant is a CpG ODN. In some embodiments, the adjuvant is a CpG ODN. In some embodiments, the CpG ODN is a Class A CpG ODN, a Class B CpG ODN, or a Class C CpG ODN. In some embodiments, the CpG ODN adjuvant comprise of a selection from the group of CpG ODN 1018, CpG ODN 1585, CpG ODN 2216, CpG ODN 2336, CpG ODN 1668, CpG ODN 1826, CPG ODN 2006, CpG ODN 2007, CpG ODN BW006, CpG ODN D-SL01, CpG ODN 2395, CpG ODN M362, CpG ODN D-SL03. In some embodiments, the CpG ODN adjuvant is CpG ODN 1826 (TCCATGACGTTCCTGACGTT (SEQ ID NO:16)) or CpG ODN 2006 (also known as CpG 7909) (TCGTCGTTTTGTCGTTTTGTCGTT (SEQ ID NO: 17)) oligonucleotide. In some embodiments, the adjuvant is CpG 7909. In some embodiments, the RIG-I agonist comprises polyinosinic: polycytidylic acid (polyI:C). Multiple adjuvants can also be used in conjunction with mutated Ras antigens to enhance the elicitation of immune response. In some embodiments, the modified PBMCs comprise more than one adjuvant. Multiple adjuvants can also be used in conjunction with mutated Ras antigens to enhance the elicitation of immune response. In some embodiments, the modified PBMCs comprise more than one adjuvant. In some embodiments, the modified PBMCs comprise any combination of the adjuvants CpG ODN, LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist.

Constrictions Used in Generating Compositions of Nucleated Cells Comprising Mutated Ras Antigen In some embodiments, the invention provides compositions of nucleated cells comprising a mutated Ras antigen for stimulating an immune response. In some embodiments, the nucleated cells are immune cells; for example, a plurality of PBMCs or one or more of T cell, B cell, NK cell, monocytes, dendritic cells or NK-T cells. In some embodiments, the mutated Ras antigen is delivered to the nucleated cells intracellularly. Methods of introducing mutated Ras antigens to nucleated cells are known in the art.

In some embodiments, the mutated Ras antigen is introduced into the nucleated cells by passing the cell through a constriction such that transient pores are introduced to the membrane of the cell thereby allowing the mutated Ras antigen to enter the cell. Examples of constriction-based delivery of compounds into a cell are provided by WO 2013/059343, WO 2015/023982, WO 2016/070136, WO2017041050, WO2017008063, WO 2017/192785, WO 2017/192786, WO 2019/178005, WO 2019/178006, WO 2020/072833, PCT/US2020/15098, and PCT/US2020/020194.

In some embodiments, the mutated Ras antigen is delivered into the nucleated cells to produce the nucleated cells of the invention by passing a cell suspension comprising the nucleated cells (e.g., PBMCs) through a constriction, wherein the constriction deforms the cells thereby causing a perturbation of the cells such that a mutated Ras antigen enters the cells. In some embodiments, the constriction is contained within a microfluidic channel. In some embodiments, multiple constrictions can be placed in parallel and/or in series within the microfluidic channel.

In some embodiments, the constriction within the microfluidic channel includes an entrance portion, a center point, and an exit portion. In some embodiments, the length, depth, and width of the constriction within the microfluidic channel can vary. In some embodiments, the width of the constriction within the microfluidic channel is a function of the diameter of the nucleated cells. Methods to determine the diameter of nucleated cells are known in the art; for example, high-content imaging, cell counters or flow cytometry.

In some embodiments of the constriction-based delivery of a mutated Ras antigen to nucleated cells, the width of the constriction is about 3 μm to about 15 μm. In some embodiments, the width of the constriction is about 3 μm to about 10 μm. In some embodiments, the width of the constriction is about 3 μm to about 6 μm. In some embodiments, the width of the constriction is about 4.2 μm to about 6 μm. In some embodiments, the width of the constriction is about 4.2 μm to about 4.8 μm. In some embodiments, the width of the constriction is about 3 μm to about 5 μm. In some embodiments, the width of the constriction is about 3 μm to about 3.5 μm. In some embodiments, the width of the constriction is about 3.5 μm to about 4 μm. In some embodiments, the width of the constriction is about 4 μm to about 4.5 μm. In some embodiments, the width of the constriction is about 3.2 μm to about 3.8 μm. In some embodiments, the width of the constriction is about 3.8 μm to about 4.3 μm. In some embodiments, the width of the constriction is about or less than any one of 2 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, 10.5 μm, 11 μm, 11.5 μm, 12 μm, 12.5 μm, 13 μm, 13.5 μm, 14 μm, 14.5 μm or 15 μm. In some embodiments, the width of the constriction is about or less than any one of 3.0 μm, 3.1 μm, 3.2 μm, 3.3 μm, 3.4 μm, 3.5 μm, 3.6 μm, 3.7 μm, 3.8 μm, 3.9 μm, 4.0 μm, 4.1 μm, 4.2 μm, 4.3 μm, 4.4 μm, 4.5 μm, 4.6 μm, 4.7 μm, 4.8 μm, 4.9 μm, or 5.0 μm. In some embodiments, the width of the constriction is about 4.5 μm.

In some embodiments of the invention, the composition comprises a plurality of nucleated cells (e.g., a plurality of PBMCs) within the population of nucleated cells. In some embodiments, the width of the constriction is about 10% to about 99% of the mean diameter of a subpopulation of nucleated cells having the smallest diameter within the population of nucleated cells. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of a subpopulation of nucleated cells having the smallest diameter within the population of nucleated cells. In some embodiments, the width of the constriction is any one of about 10% to about 20%, about 20% to about 30%, about 30% to about 40%, about 40% to about 50%, about 50% to about 60%, about 60% to about 70%, about 70% to about 80%, about 80% to about 90%, or about 90% to about 99% of the mean diameter of a subpopulation of nucleated cells having the smallest diameter within the population of nucleated cells. In some embodiments, the width of the constriction is any one of about 10%, 15%, 20%, 25%, 30%, 35%, 40%, 45%, 50%, 55%, 60%, 65%, 70%, 75%, 80%, 85%, 90%, 95%, or 99% of the mean diameter of a subpopulation of nucleated cells having the smallest diameter within the population of nucleated cells. In some embodiments, the subpopulation of nucleated cells having the smallest mean diameter within a plurality of input PBMCs is a population of lymphocytes, wherein the diameter of the population of lymphocytes is about 6 μm to about 10 μm. In some embodiments, the mean diameter of the population of lymphocytes is about 7 μm. In some embodiments, the population of lymphocytes is a population of T cells. In some embodiments, the lymphocytes are T cells. In some embodiments, the subpopulation of nucleated cells having the smallest mean diameter within the plurality of input PBMCs are T cells.

In some embodiments of the invention, the composition comprises a plurality of nucleated cells (e.g., a plurality of PBMCs) within the population of nucleated cells. In some embodiments, the width of the constriction is about 10% to about 99% of the mean diameter of a subpopulation of nucleated cells having the largest diameter within the population of nucleated cells. In some embodiments, the width of the constriction is any one of about 10% to about 90%, about 10% to about 80%, about 10% to about 70%, about 20% to about 60%, about 40% to about 60%, about 30% to about 45%, about 15% to about 30%, about 15% to about 20%, about 20% to about 25%, about 25% to about 30%, about 20% to about 30%, about 30% to about 70%, or about 30% to about 60% of the mean diameter of a subpopulation of nucleated cells having the largest diameter within the population of nucleated cells. In some embodiments, the width of the constriction is any one of about 5% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to about 99% of the mean diameter of a subpopulation of nucleated cells having the largest diameter within the population of nucleated cells. In some embodiments, the width of the constriction is any one of about 5%, 10%, 15%, 20%, 25%, 30%, 35%, 40%, 45%, 50%, 55%, 60%, 65%, 70%, 75%, 80%, 85%, 90%, 95%, or 99% of the mean diameter of a subpopulation of nucleated cells having the largest diameter within the population of nucleated cells. In some embodiments, the subpopulation of nucleated cells having the largest mean diameter within a plurality of input PBMCs is a population of monocytes, wherein the diameter of the population of monocytes is about 15 μm to about 25 μm. In some embodiments, the mean diameter of the population of monocytes is about 18 μm. In some embodiments, the subpopulation of nucleated cells having the largest mean diameter within the plurality of input PBMCs are monocytes.

A number of parameters may influence the delivery of a compound to nucleated cells for stimulating an immune response by the methods described herein. In some embodiments, the cell suspension is contacted with the compound before, concurrently, or after passing through the constriction. The nucleated cells may pass through the constriction suspended in a solution that includes the compound to deliver, although the compound can be added to the cell suspension after the nucleated cells pass through the constriction. In some embodiments, the compound to be delivered is coated on the constriction.

Examples of parameters that may influence the delivery of the compound into the nucleated cells include, but are not limited to, the dimensions of the constriction, the entrance angle of the constriction, the surface properties of the constrictions (e.g., roughness, chemical modification, hydrophilic, hydrophobic, etc.), the operating flow speeds (e.g., cell transit time through the constriction), the cell concentration, the concentration of the compound in the cell suspension, buffer in the cell suspension, and the amount of time that the nucleated cells recover or incubate after passing through the constrictions can affect the passage of the delivered compound into the nucleated cells. Additional parameters influencing the delivery of the compound into the nucleated cells can include the velocity of the nucleated cells in the constriction, the shear rate in the constriction, the viscosity of the cell suspension, the velocity component that is perpendicular to flow velocity, and time in the constriction. In addition, multiple chips comprising channels in series and/or in parallel may impact delivery to nucleated cells. Multiple chips in parallel may be useful to enhance throughput. Such parameters can be designed to control delivery of the compound. In some embodiments, the cell concentration ranges from about 10 to at least about $10^{12}$ cells/mL or any concentration or range of concentrations therebetween. In some embodiments, delivery compound concentrations can range from about 10 ng/mL to about 1 g/mL or any concentration or range of concentrations therebetween. In some embodiments, delivery compound concentrations can range from about 1 μM to at least about 2 M or any concentration or range of concentrations therebetween.

In some embodiments, the concentration of mutated Ras antigen incubated with the nucleated cells is between about 0.01 μM and about 10 mM. For example, in some embodiments, the concentration of mutated Ras antigen incubated with the nucleated cells is any of less than about 0.01 μM, about 0.1 μM, about 1 μM, about 10 μM, about 100 μM, about 1 mM or about 10 mM. In some embodiments, the concentration of mutated Ras antigen incubated with the nucleated cells is greater than about 10 mM. In some embodiments, the concentration of mutated Ras antigen incubated with the nucleated cells is any of between about 0.01 UM and about 0.1 μM, between about 0.1 μM and about 1 μM, between about 1 μM and about 10 μM, between about 10 μM and about 100 μM, between about 100 μM and about 1 mM, or between 1 mM and about 10 mM. In some embodiments, the concentration of mutated Ras antigen incubated with the nucleated cells is between about 0.1 μM and about 1 mM. In some embodiments, the concentration of mutated Ras antigen incubated with the nucleated cells is between about 0.1 μM and about 10 μM. In some embodiments, the concentration of mutated Ras antigen incubated with the nucleated cells is 1 μM.

In some embodiments, the nucleated cells comprise the nucleic acid encoding the mutated Ras antigen at a concentration between about 1 nM and about 1 mM. In some embodiments, the nucleated cells comprises the nucleic acid encoding the mutated Ras antigen at a concentration of any of less than about 0.1 nM, about 1 nM, about 0.01 μM, about 0.1 μM, about 1 μM, about 10 μM, about 100 μM, about 1 mM or about 10 mM. In some embodiments, the nucleated cells comprise the nucleic acid encoding the mutated Ras antigen at a concentration of greater than about 10 mM. In some embodiments, the nucleated cells comprise the nucleic acid encoding the mutated Ras antigen at a concentration of any of between about 0.1 nM to about 1 nM, about 1 nM to about 10 nM, about 10 nM to about 100 nM, about 0.1 μM and about 1 μM, between about 1 μM and about 10 μM, between about 10 UM and about 100 μM, between about 100 μM and about 1 mM, or between 1 mM and about 10 mM. In some embodiments, the nucleated cells comprise the nucleic acid encoding the mutated Ras antigen at a concentration between about 10 nM and about 100 nM. In some embodiments, the nucleated cells comprise the nucleic acid encoding the mutated Ras antigen at a concentration between about 1 nM and about 10 nM. In some embodiments, the nucleated cells comprise the mutated Ras antigen at a concentration of about 50 nM. In some embodiments, the nucleic acid is an mRNA.

Conditioning of Nucleated Cells

In some embodiments according to any one of methods described herein; the nucleated cells (e.g., PBMCs) comprising a mutated Ras antigen are conditioned. In further embodiments, the nucleated cells are matured. In some embodiments, the nucleated cells are conditioned subsequent to constriction mediated delivery. In some embodiments, the nucleated cells comprising the mutated Ras antigen is incubated with an adjuvant for a sufficient time for the cells comprising the constriction-delivered mutated Ras antigen to condition, thereby generating a composition of conditioned cells comprising the mutated Ras antigen. In some embodiments, the nucleated cells are conditioned subsequent to constriction-mediated delivery. In some embodiments, the nucleated cells comprising the constriction-delivered mutated Ras antigen are incubated with an adjuvant for a sufficient time for the nucleated cells comprising the constriction-delivered mutated Ras antigen to condition, thereby generating a composition of conditioned nucleated cells comprising the mutated Ras antigen. In some aspects, there is provided a composition of conditioned nucleated cells comprising an mutated Ras antigen, prepared by a process comprising the steps of: a) passing a cell suspension through a cell-deforming constriction, wherein a width of the constriction is a function of the nucleated cells in the suspension, thereby causing perturbations of the nucleated cells large enough for the mutated Ras antigen to pass through to form perturbed nucleated cells; b) incubating the perturbed nucleated cells with the mutated Ras antigen for a sufficient time to allow the mutated Ras antigen to enter the perturbed nucleated cells, thereby generating modified nucleated cells comprising the mutated Ras antigen; and c) incubating the modified nucleated cells comprising the constriction-delivered mutated Ras antigen with an adjuvant for a sufficient time for the modified nucleated cells comprising the constriction-delivered mutated Ras antigen to condition, thereby generating the composition of conditioned nucleated cells comprising the mutated Ras antigen. In some embodiments, the process further comprises isolating the modified nucleated cells comprising the mutated Ras antigen from the cell suspension before incubation with the adjuvant to condition the modified nucleated cells.

In some embodiments, the nucleated cells (e.g., PBMCs) are conditioned prior to constriction-mediated delivery. In some embodiments, the nucleated cells are incubated with an adjuvant for a sufficient time for the nucleated cells to condition, thereby conditioning nucleated cells. In some embodiments, there is provided a composition of conditioned nucleated cells comprising a mutated Ras antigen, prepared by a process comprising the steps of: a) incubating nucleated cells with an adjuvant for a sufficient time for the nucleated cells to condition, thereby generating conditioned nucleated cells; b) passing a cell suspension comprising the conditioned nucleated cells through a cell-deforming constriction, wherein a width of the constriction is a function of a diameter of the nucleated cells in the suspension, thereby causing perturbations of the nucleated cells large enough for the mutated Ras antigen to pass through to form conditioned perturbed nucleated cells; and c) incubating the conditioned perturbed nucleated cells with the mutated Ras antigen for a sufficient time to allow the mutated Ras antigen to enter the conditioned perturbed nucleated cells, thereby generating the conditioned nucleated cells comprising the mutated Ras antigen. In some embodiments, the process further comprises isolating the conditioned nucleated cells from the adjuvant before passing the conditioned nucleated cells through a cell-deforming constriction.

In some embodiments according to any one of methods described herein, the nucleated cells (e.g., PBMCs) comprising the mutated Ras antigen are incubated with the adjuvant for about 1 to about 24 hours for the nucleated cells to condition. In some embodiments, the nucleated cells are incubated with the adjuvant for about 2 to about 10 hours for the nucleated cells to condition. In some embodiments, the nucleated cells are incubated with the adjuvant for about 3 to about 6 hours for the nucleated cells to condition. In some embodiments, the nucleated cells are incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the nucleated cells to condition. In some embodiments, the nucleated cells are incubated with the adjuvant for about 4 hours for the nucleated cells to condition.

In some embodiments, there is provided a conditioned plurality of PBMCs comprising a mutated Ras antigen, prepared by incubating the plurality of PBMCs comprising the mutated Ras antigen with an adjuvant for a sufficient time for the PBMCs to condition, thereby generating the conditioned plurality of PBMCs comprising the mutated Ras antigen. In some embodiments, there is provided a conditioned plurality of PBMCs comprising a mutated Ras antigen, prepared by incubating the plurality of PBMCs with an adjuvant for a sufficient time for the PBMCs to condition prior to introducing the mutated Ras antigen to the PBMCs, thereby generating the conditioned plurality of PBMCs comprising the mutated Ras antigen.

In some embodiments according to any of the conditioned plurality of PBMCs described herein, the plurality of PBMCs is incubated with the adjuvant for about 1 to about 24 hours for the PBMCs to condition. In some embodiments, the plurality of PBMCs is incubated with the adjuvant for about 2 to about 10 hours for the PBMCs to condition. In some embodiments, the plurality of PBMCs is incubated with the adjuvant for about 3 to about 6 hours for the PBMCs to condition. In some embodiments, the plurality of PBMCs is incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the PBMCs to condition. In some embodiments, the plurality of PBMCs is incubated with the adjuvant for about 4 hours for the PBMCs to condition.

In some embodiments according to any one of the conditioned plurality of PBMCs described herein, one or more co-stimulatory molecules are upregulated in the conditioned plurality of modified PBMCs compared to an unconditioned plurality of modified PBMCs. In some embodiments, one or more co-stimulatory molecules are upregulated in a subpopulation of cells in the conditioned plurality of modified PBMCs compared to the subpopulation of cells in an unconditioned plurality of modified PBMCs. In some embodiments, one or more co-stimulatory molecules are upregulated in the B cells of the conditioned plurality of modified PBMCs compared to the B cells in an unconditioned plurality of modified PBMCs. In some embodiments, the co-stimulatory molecule is CD80 and/or CD86. In some embodiments, the co-stimulatory molecule is CD86. In some embodiments, the CD80 and/or CD86 is upregulated in the B cells of the conditioned plurality of modified PBMCs by more than about 1.2-fold, 1.5-fold, 1.8-fold, 2-fold, 3-fold, 4-fold, 5-fold, 8-fold, or more than 10-fold compared to the B cells in an unconditioned plurality of modified PBMCs. In some embodiments, the CD80 and/or CD86 is upregulated in the B cells of the conditioned plurality of modified PBMCs by any of about 1.2-fold to about 1.5-fold, about 1.5-fold to about 1.8-fold, about 1.8-fold to about 2-fold, about 2-fold to about 3-fold, about 3-fold to about 4-fold, about 4-fold to about 5-fold, about 5-fold to about 8-fold, about 8-fold to about 10-fold, about 10-fold to about 20-fold, about 20-fold to about 50-fold, about 50-fold to about 100-fold, about 100-fold to about 200-fold, about 200-fold to about 500-fold, or more than about 500-fold compared to the B cells in an unconditioned plurality of modified PBMCs. In some embodiments, the expression of one or more of IFN-γ, IL-6, MCP-1, MIP-1β, IP-10, or TNF-α is increased in the conditioned plurality of modified PBMCs compared to an unconditioned plurality of modified PBMCs. In some embodiments, the expression of one or more of IFN-γ, IL-6, MCP-1, MIP-1β, IP-10, or TNF-α is increased a subpopulation of cells in the conditioned plurality compared to the subpopulation of cells in an unconditioned plurality of modified PBMCs. In some embodiments, the expression of one or more of IFN-γ, IL-6, MCP-1, MIP-1β, IP-10, or TNF-α is increased by about 1.2-fold, 1.5-fold, 1.8-fold, 2-fold, 3-fold, 4-fold, 5-fold, 8-fold, or more than 10-fold in the conditioned plurality of modified PBMCs compared to an unconditioned plurality of modified PBMCs. In some embodiments, the expression of one or more of IFN-γ, IL-6, MCP-1, MIP-1β, IP-10, or TNF-α is increased by any of about 1.2-fold to about 1.5-fold, about 1.5-fold to about 1.8-fold, about 1.8-fold to about 2-fold, about 2-fold to about 3-fold, about 3-fold to about 4-fold, about 4-fold to about 5-fold, about 5-fold to about 8-fold, about 8-fold to about 10-fold, about 10-fold to about 20-fold, about 20-fold to about 50-fold, about 50-fold to about 100-fold, about 100-fold to about 200-fold, about 200-fold to about 500-fold, or more than about 500-fold in the conditioned plurality of modified PBMCs compared to an unconditioned plurality of modified PBMCs.

Systems and Kits

In some aspects, the invention provides a system comprising one or more of the constriction, an immune cell suspension, mutated Ras antigens or adjuvants for use in the methods disclosed herein. The system can include any embodiment described for the methods disclosed above, including microfluidic channels or a surface having pores to provide cell-deforming constrictions, cell suspensions, cell perturbations, delivery parameters, compounds, and/or applications etc. In some embodiment, the cell-deforming constrictions are sized for delivery to immune cells. In some embodiments, the delivery parameters, such as operating flow speeds, cell and compound concentration, velocity of the cell in the constriction, and the composition of the cell suspension (e.g., osmolarity, salt concentration, serum content, cell concentration, pH, etc.) are optimized for maximum response of a compound for suppressing an immune response or inducing tolerance.

Also provided are kits or articles of manufacture for use in treating individuals with a cancer associated with a Ras mutation. In some embodiments, the kit comprises a modified immune cell comprising intracellularly a mutated antigen and intracellularly an adjuvant. In some embodiments, the kit comprises one or more of the constriction, an immune cell suspension, mutated Ras antigens or adjuvants for use in generating modified immune cells for use in treating an individual with a cancer associated with a Ras mutation, such as cancer. In some embodiments, the kits comprise the compositions described herein (e.g. a microfluidic channel or surface containing pores, cell suspensions, and/or compounds) in suitable packaging. Suitable packaging materials are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The invention also provides kits comprising components of the methods described herein and may further comprise instructions for performing said methods treat an individual with a cancer associated with a Ras mutation and/or instructions for introducing a mutated Ras antigen and an adjuvant into an immune cell. The kits described herein may further include other materials, including other buffers, diluents, filters, needles, syringes, and package inserts with instructions for performing any methods described herein; e.g., instructions for treating an individual with a cancer associated with a Ras mutation or instructions for modifying an immune cell to contain intracellularly a mutated Ras antigen and intracellularly an adjuvant.

EXEMPLARY EMBODIMENTS

Embodiment 1. A method for stimulating an immune response to a mutated Ras protein in an individual, the method comprising administering an effective amount of a composition comprising nucleated cells to an individual, wherein the nucleated cells comprise a mutated Ras antigen; wherein the mutated Ras antigen is delivered to the nucleated cell intracellularly.

Embodiment 2. A method for reducing tumor growth in an individual, the method comprising administering an effective amount of a composition comprising nucleated cells to an individual, wherein the nucleated cells comprise a mutated Ras antigen; wherein the mutated Ras antigen is delivered to the nucleated cell intracellularly.

Embodiment 3. A method for vaccinating an individual in need thereof, the method comprising administering an effective amount of a composition comprising nucleated cells to an individual, wherein the nucleated cells comprise a mutated Ras antigen; wherein the mutated Ras antigen is delivered to the nucleated cell intracellularly.

Embodiment 4. The method of any one of embodiments 1-3, wherein the individual has cancer.

Embodiment 5. A method for treating cancer in an individual, the method comprising administering an effective amount of a composition comprising nucleated cells to an individual, wherein the nucleated cells comprise a mutated Ras antigen; wherein the mutated Ras antigen is delivered to the nucleated cell intracellularly.

Embodiment 6. The method of embodiment 4 or 5, wherein the cancer is a pancreatic cancer, a colon cancer, a small intestine cancer, a biliary tract cancer, an endometrial cancer, a lung cancer, a skin cancer, an ovarian cancer, a stomach cancer, an esophageal cancer, a cervical cancer or a urinary tract cancer.

Embodiment 7. The method of any one of embodiments 1-6, wherein the mutated Ras antigen is a mutated K-Ras antigen, a mutated H-Ras antigen, or a mutated N-Ras antigen.

Embodiment 8. The method of any one of embodiments 1-7, wherein the mutated Ras antigen is a mutated K-Ras4A antigen or a mutated K-Ras4B antigen.

Embodiment 9. The method of any one of embodiments 1-8, wherein the mutated Ras antigen is a single polypeptide that elicits a response against the same and or different mutated Ras antigens.

Embodiment 10. The method of any one embodiments 1-8, wherein the mutated Ras antigen is a pool of multiple polypeptides that elicit a response against the same and or different mutated Ras antigens.

Embodiment 11. The method of any one of embodiments 1-10, wherein the mutated Ras antigen is a polypeptide comprising one or more antigenic mutated Ras epitopes and one or more heterologous peptide sequences.

Embodiment 12. The method of any one of embodiments 1-11, wherein the mutated Ras antigen complexes with other antigens or with an adjuvant.

Embodiment 13. The method of any one of embodiments 1-12, wherein the mutated Ras antigen comprises a G12D mutation, a G12V mutation, a G12C mutation or a G13D mutation.

Embodiment 14. The method of any one of embodiments 1-13, wherein the mutated Ras antigen comprises an amino acid sequence with at least 90% similarity to any one of SEQ ID NOs: 9-15.

Embodiment 15. The method of any one of embodiments 1-14, wherein the mutated Ras antigen comprises an amino acid sequence of SEQ ID NOs: 9-15.

Embodiment 16. The method of any one of embodiments 1-15, wherein the mutated Ras antigen is one or more of a $G12D^{1-16}$, a $G12D^{2-19}$, a $G12D^{2-22}$, a $G12D^{2-29}$, a $G12V^{1-16}$, a $G12V^{2-19}$, a $G12V^{3-17}$, or a $G12V^{3-42}$ antigen.

Embodiment 17. The method of any one of embodiments 1-16, wherein the mutated Ras antigen comprises an amino acid sequence with at least 90% similarity to any one of SEQ ID NOs: 1-8.

Embodiment 18. The method of any one of embodiments 1-17, wherein the mutated Ras antigen comprises an amino acid sequence of SEQ ID NOs: 1-8.

Embodiment 19. The method of any one of embodiments 1-18, wherein the mutated Ras antigen is a polypeptide comprising one or more antigenic mutated Ras epitopes that is flanked on the N-terminus and/or the C-terminus by one or more heterologous peptide sequences.

Embodiment 20. The method of any one of embodiments 1-19, wherein the mutated Ras antigen is capable of being processed into an MHC class I-restricted peptide.

Embodiment 21. The method of any one of embodiments 1-20, wherein the mutated Ras antigen is capable of being processed into an MHC class II-restricted peptide.

Embodiment 22. The method of any one of embodiments 1-21, wherein the composition further comprises an adjuvant.

Embodiment 23. The method of any one of embodiments 1-22, wherein the composition is administered in conjunction with an adjuvant.

Embodiment 24. The method of embodiment 23, wherein the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist.

Embodiment 25. The method of any one of embodiments 1-24, wherein the nucleated cells comprising the mutated Ras antigen are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mutated Ras antigen to pass through to form a perturbed input nucleated cells; and b) incubating the perturbed input nucleated cells with the mutated Ras antigen for a sufficient time to allow the mutated Ras antigen to enter the perturbed input nucleated cells; thereby generating nucleated cells comprising the mutated Ras antigen.

Embodiment 26. The method of any one of embodiments 1-24, wherein the nucleated cells comprising the mutated Ras antigen are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for a nucleic acid encoding the mutated Ras antigen to pass through to form a perturbed input nucleated cells; and b) incubating the perturbed input nucleated cells with the nucleic acid encoding the mutated Ras antigen for a sufficient time to allow the nucleic acid encoding the mutated Ras antigen to enter the perturbed input nucleated cells; wherein the nucleic acid encoding the mutated Ras is expressed thereby generating nucleated cells comprising the mutated Ras antigen.

Embodiment 27. The method of embodiment 25 or 26, wherein the width of the constriction is about 10% to about 99% of the mean diameter of the input nucleated cells.

Embodiment 28. The method of any one of embodiments 25-27, wherein the width of the constriction is about 3.5 μm to about 4.2 μm or about 3.5 μm to about 4.8 μm or about 3.5 μm to about 6 μm or about 4.2 μm to about 4.8 μm or about 4.2 μm to about 6 μm.

Embodiment 29. The method of any one of embodiments 25-28, wherein the width of the constriction is about 3.5 μm.

Embodiment 30. The method of any one of embodiments 25-28, wherein the width of the constriction is about 4.5 μm.

Embodiment 31. The method of any one of embodiments 25-30, wherein the cell suspension comprising the plurality of input nucleated cells are passed through multiple constrictions wherein the multiple constrictions are arranged in series and/or in parallel.

Embodiment 32. The method of any one of embodiments 1-31, wherein the nucleated cells are immune cells.

Embodiment 33. The method of any one of embodiments 1-32, wherein the nucleated cells are human cells with a haplotype of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16.

Embodiment 34. The method of any one of embodiments 1-33, wherein the nucleated cells are a plurality of peripheral blood mononuclear cells (PBMCs).

Embodiment 35. The method of embodiment 34, wherein the plurality of PBMCs comprise two or more of T cell, B cell, NK cell, monocytes, dendritic cells or NK-T cells.

Embodiment 36. The method of any one of embodiments 1-35, wherein the nucleated cells are one or more of T cells, B cells, NK cells, monocytes, dendritic cells and/or NK-T cells.

Embodiment 37. The method of any one of embodiments 1-36, wherein the nucleated cells are conditioned with an adjuvant to form conditioned cells.

Embodiment 38. The method of embodiment 37, wherein the nucleated cells are incubated with the adjuvant for about 1 hour to about 24 hours, about 2 hours to about 10 hours, about 3 hours to about 6 hours, or about 4 hours for the cells to condition.

Embodiment 39. The method of embodiment 37 or 38, wherein the nucleated cells are conditioned before or after introducing the mutated Ras antigen into the nucleated cells.

Embodiment 40. The method of any one of embodiments 37-39, wherein the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist.

Embodiment 41. The method of any one of embodiments 37-40, wherein the adjuvant is a CpG oligodeoxynucleotide (ODN).

Embodiment 42. The method of any one of embodiments 37-41, wherein the adjuvant is CpG 7909.

Embodiment 43. The method of any one of embodiments 37-42, wherein the conditioned cells are a conditioned plurality of PBMCs.

Embodiment 44. The method of embodiment 43, wherein the plurality of PBMCs are modified to increase expression of one or more of co-stimulatory molecules.

Embodiment 45. The method of embodiment 44, wherein the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112.

Embodiment 46. The method of any one of embodiments 43-45, wherein the plurality of PBMCs are modified to increase expression of one or more cytokines.

Embodiment 47. The method of embodiment 46, wherein the cytokine is IL-15, IL-12, IL-2, IFN-α, or IL-21.

Embodiment 48. The method of any one of embodiment 43-45, wherein one or more co-stimulatory molecules is upregulated in the B cells of the conditioned plurality of PBMCs compared to the B cells in the plurality of nonconditioned PBMCs, wherein the co-stimulatory molecule is CD80 and/or CD86.

Embodiment 49. The method of any one of embodiments 43-48, wherein the plurality of PBMCs have increased expression of one or more of IFN-γ, IL-6, MCP-1, MIP-1β, IP-10, or TNF-α compared to a plurality of unconditioned PBMCs.

Embodiment 50. The method of embodiment 49, wherein the expression of one or more of IFN-γ, IL-6, MCP-1, MIP-1β, IP-10, or TNF-α is increased by more than about 1.2-fold, 1.5-fold, 1.8-fold, 2-fold, 3-fold, 4-fold, 5-fold, 8-fold, or more than 10-fold compared to the plurality of unconditioned PBMCs.

Embodiment 51. The method of any one of embodiments 1-50, wherein the composition comprising nucleated cells is administered a plurality of times.

Embodiment 52. The method of any one of embodiments 1-51, wherein the composition is administered intravenously.

Embodiment 53. The method of any one of embodiments 1-52, wherein the individual is a human.

Embodiment 54. The method of any one of embodiments 1-53, wherein the composition is administered prior to, concurrently with, or following administration of another therapy.

Embodiment 55. The method of embodiment 54, wherein another therapy is a chemotherapy, a radiation therapy, an antibody, a cytokine, an immune checkpoint inhibitor, or a bispecific polypeptide used in immune-oncology therapy.

Embodiment 56. A composition comprising conditioned nucleated cells, wherein the nucleated cells comprise a mutated Ras antigen; wherein the mutated Ras antigen antigen is delivered to the nucleated cell intracellularly.

Embodiment 57. The composition of embodiment 56, wherein the nucleated cells are conditioned with an adjuvant to form conditioned cells.

Embodiment 58. A composition comprising conditioned nucleated cells comprising a mutated Ras antigen, wherein the conditioned nucleated cells comprising the mutated Ras antigen are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mutated Ras antigen to pass through to form a perturbed input nucleated cells;
b) incubating the perturbed input nucleated cells with the mutated Ras antigen for a sufficient time to allow the mutated Ras antigen to enter the perturbed input nucleated cells; thereby generating nucleated cells comprising the mutated Ras antigen; and
c) incubating the nucleated cells with the adjuvant for the nucleated cells to condition.

Embodiment 59. A composition comprising conditioned nucleated cells comprising a mutated Ras antigen, wherein the conditioned nucleated cells comprising the mutated Ras antigen are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for a nucleic acid encoding the mutated Ras antigen to pass through to form a perturbed input nucleated cells;
b) incubating the perturbed input nucleated cells with the nucleic acid encoding the mutated Ras antigen for a sufficient time to allow the nucleic acid encoding the mutated Ras antigen to enter the perturbed input nucleated cells; thereby generating nucleated cells comprising the nucleic acid encoding mutated Ras antigen, wherein the nucleic acid encoding the mutated H-Ras antigen is expressed thereby generating a nucleated cell comprising a mutated H-Ras antigen; and
c) incubating the nucleated cells with the adjuvant for the nucleated cells to condition.

Embodiment 60. The composition of any one of embodiments 57-59, wherein the nucleated cells are incubated with the adjuvant for about 1 hour to about 24 hours, about 2 hours to about 10 hours, about 3 hours to about 6 hours, or about 4 hours for the cells to condition.

Embodiment 61. The composition of any one of embodiments 57-60, wherein the nucleated cells are conditioned before or after introducing the mutated Ras antigen or the nucleic acid encoding the mutated Ras antigen into the nucleated cells.

Embodiment 62. The composition of any one of embodiments 57-61, wherein the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist.

Embodiment 63. The composition of any one of embodiments 57-62, wherein the adjuvant is a CpG oligodeoxynucleotide (ODN).

Embodiment 64. The composition of any one of embodiments 57-63, wherein the adjuvant is CpG 7909.

Embodiment 65. The composition of any one of embodiments 57-64, wherein the nucleated cells are immune cells.

Embodiment 66. The composition of any one of embodiments 57-65, wherein the nucleated cells are human cells with a haplotype of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16.

Embodiment 67. The composition of any one of embodiments 57-66, wherein the conditioned cells are a conditioned plurality of PBMCs.

Embodiment 68. The composition of embodiment 67, wherein the plurality of PBMCs comprise two or more of T cell, B cell, NK cell, monocytes, dendritic cells or NK-T cells.

Embodiment 69. The method of embodiment 67 or 68, wherein the nucleated cells are one or more of T cells, B cells, NK cells, monocytes, dendritic cells and/or NK-T cells.

Embodiment 70. The composition of any one of embodiments 67-69, wherein the plurality of PBMCs are modified to increase expression of one or more of co-stimulatory molecules.

Embodiment 71. The composition of embodiment 70, wherein the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112.

Embodiment 72. The composition of any one of embodiments 67-71, wherein the plurality of PBMCs are modified to increase expression of one or more cytokines.

Embodiment 73. The composition of embodiment 72, wherein the cytokine is IL-15, IL-12, IL-2, IFN-α, or IL 21.

Embodiment 74. The composition of any one of embodiment 67-73, wherein one or more co-stimulatory molecules is upregulated in the B cells of the conditioned plurality of PBMCs compared to the B cells in the plurality of nonconditioned PBMCs, wherein the co-stimulatory molecule is CD80 and/or CD86.

Embodiment 75. The composition of any one of embodiments 67-74, wherein the conditioned plurality of PBMCs have increased expression of one or more of IFN-γ, IL-6, MCP-1, MIP-1β, IP-10, or TNF-α compared to a unconditioned plurality of PBMCs.

Embodiment 76. The composition of embodiment 75, wherein the expression of one or more of IFN-γ, IL-6, MCP-1, MIP-1β, IP-10, or TNF-α is increased by more than about 1.2-fold, 1.5-fold, 1.8-fold, 2-fold, 3-fold, 4-fold, 5-fold, 8-fold, or more than 10-fold compared to the plurality of unconditioned PBMCs.

Embodiment 77. A composition comprising nucleated cells, wherein the nucleated cells comprise a mutated Ras antigen; wherein the mutated Ras antigen is delivered to the nucleated cell intracellularly.

Embodiment 78. A composition comprising nucleated cells comprising a mutated Ras antigen, wherein the nucleated cells comprising the mutated Ras antigen are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mutated Ras antigen to pass through to form perturbed input nucleated cells; and b) incubating the perturbed input nucleated cells with the mutated Ras antigen for a sufficient time to allow the mutated Ras antigen to enter the perturbed input nucleated cells; thereby generating nucleated cells comprising the mutated Ras antigen.

Embodiment 79. A composition comprising nucleated cells comprising a mutated Ras antigen, wherein the nucleated cells comprising the mutated Ras antigen are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for a nucleic acid encoding the mutated Ras antigen to pass through to form perturbed input nucleated cells; and b) incubating the perturbed input nucleated cells with the nucleic acid encoding the mutated Ras antigen for a sufficient time to allow the nucleic acid encoding the mutated Ras antigen to enter the perturbed input nucleated cells, wherein the nucleic acid expressed the mutated Ras antigen; thereby generating nucleated cells comprising the mutated Ras antigen.

Embodiment 80. The composition of any one of embodiments 58, 59, 78 and 79, wherein the width of the constriction is about 10% to about 99% of the mean diameter of the input nucleated cells.

Embodiment 81. The composition of any one of embodiments 58, 59, and 78-80, wherein the width of the constriction is about 4.2 μm to about 6 μm, about 4.2 μm to about 4.8 μm, or about 3.5 μm to about 6 μm or about 4.2 μm to about 4.8 μm or about 4.2 μm to about 6 μm.

Embodiment 82. The composition of any one of embodiments 58, 59, and 78-81, wherein the width of the constriction is about 3.5 μm.

Embodiment 83. The composition of any one of embodiments 58, 59, and 78-82, wherein the width of the constriction is about 4.5 μm.

Embodiment 84. The composition of any one of embodiments 58, 59, and 78-83, wherein the cell suspension comprising the input nucleated cells are passed through multiple constrictions wherein the multiple constrictions are arranged in series and/or in parallel.

Embodiment 85. The composition of any one of embodiments 78-84, wherein the nucleated cells are immune cells.

Embodiment 86. The composition of any one of embodiments 78-81, wherein the nucleated cells are human cells with a haplotype of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16.

Embodiment 87. The composition of any one of embodiments 78-82, wherein the nucleated cells are a plurality of peripheral blood mononuclear cells (PBMCs).

Embodiment 88. The composition of embodiment 87, wherein the plurality of PBMCs comprise two or more of T cell, B cell, NK cell, monocytes, dendritic cells or NK-T cells.

Embodiment 89. The composition of any one of embodiments 78-88, wherein the nucleated cells are one or more of T cells, B cells, NK cells, monocytes, dendritic cells and/or NK-T cells.

Embodiment 90. The composition of any one of embodiments 56-89, wherein the mutated Ras antigen is a mutated K-Ras antigen, a mutated H-Ras antigen, or a mutated N-Ras antigen.

Embodiment 91. The composition of any one of embodiments 56-89, wherein the mutated Ras antigen is a mutated K-Ras4A antigen or a mutated K-Ras4B antigen.

Embodiment 92. The composition of any one of embodiments 56-91, wherein the mutated Ras antigen is a single polypeptide that elicits a response against the same and or different mutated Ras antigens.

Embodiment 93. The composition of any one embodiments 56-91, wherein the mutated Ras antigen is a pool of multiple polypeptides that elicit a response against the same and or different mutated Ras antigens.

Embodiment 94. The composition of any one of embodiments 56-91, wherein the mutated Ras antigen is a polypeptide comprising one or more antigenic mutated Ras epitopes and one or more heterologous peptide sequences.

Embodiment 95. The composition of any one of embodiments 56-94, wherein the mutated Ras antigen complexes with other antigens or with an adjuvant.

Embodiment 96. The composition of any one of embodiments 56-95, wherein the mutated Ras antigen comprises a G12D mutation, a G12V mutation, a G12C mutation or a G13D mutation.

Embodiment 97. The composition of any one of embodiments 56-96, wherein the mutated Ras antigen comprises an amino acid sequence with at least 90% similarity to any one of SEQ ID NOs: 9-15.

Embodiment 98. The composition of any one of embodiments 56-97, wherein the mutated Ras antigen comprises an amino acid sequence of SEQ ID NOs: 9-15.

Embodiment 99. The composition of any one of embodiments 56-98, wherein the mutated Ras antigen is one or more of a $G12D^{1-16}$, a $G12D^{2-19}$, a $G12D^{2-22}$, a $G12D^{2-29}$, a $G12V^{1-16}$, a $G12V^{2-19}$, a $G12V^{3-17}$, or a $G12V^{3-42}$ antigen.

Embodiment 100. The composition of any one of embodiments 56-99, wherein the mutated Ras antigen comprises an amino acid sequence with at least 90% similarity to any one of SEQ ID NOs: 1-8.

Embodiment 101. The composition of any one of embodiments 56-100, wherein the mutated Ras antigen comprises an amino acid sequence of SEQ ID NOs: 1-8.

Embodiment 102. The composition of any one of embodiments 56-101, wherein the mutated Ras antigen is a polypeptide comprising one or more antigenic mutated Ras epitopes that is flanked on the N-terminus and/or the C-terminus by one or more heterologous peptide sequences.

Embodiment 103. The composition of any one of embodiments 56-102, wherein the mutated Ras antigen is capable of being processed into an MHC class I-restricted peptide.

Embodiment 104. The composition of any one of embodiments 56-103, wherein the mutated Ras antigen is capable of being processed into an MHC class II-restricted peptide.

Embodiment 105. The composition of any one of embodiments 56-104, wherein the composition further comprises an adjuvant.

Embodiment 106. The composition of embodiment 99, wherein the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist.

Embodiment 107. A composition for stimulating an immune response to mutated Ras protein in an individual, wherein the composition comprises an effective amount of the composition of any one of embodiments 56-106.

Embodiment 108. A composition for reducing tumor growth in an individual, wherein the composition comprises an effective amount of the composition of any one of embodiments 56-106.

Embodiment 109. The composition of embodiment 107 or 108, wherein the individual has cancer.

Embodiment 110. A composition for treating cancer in an individual, wherein the composition comprises an effective amount of the composition of any one of embodiments 56-106.

Embodiment 111. The composition of embodiment 109 or 110, wherein the cancer is a pancreatic cancer, a colon cancer, a small intestine cancer, a biliary tract cancer, an endometrial cancer, a lung cancer, a skin cancer, an ovarian cancer, a stomach cancer, an esophageal cancer, a cervical cancer or a urinary tract cancer.

Embodiment 112. The composition of any one of embodiments 107-111, wherein the composition further comprises an adjuvant.

Embodiment 113. The composition of any one of embodiments 107-111, wherein the composition is administered in conjunction with an adjuvant.

Embodiment 114. The composition of embodiment 113, wherein the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist.

Embodiment 115. The composition of any one of embodiments 107-114, wherein the composition comprising nucleated cells is administered a plurality of times.

Embodiment 116. The composition of any one of embodiments 107-115, wherein the composition is administered intravenously.

Embodiment 117. The composition of any one of embodiments 107-116, wherein the individual is a human.

Embodiment 118. The composition of any one of embodiments 101-111, wherein the composition is administered prior to, concurrently with, or following administration of another therapy.

Embodiment 119. The composition of embodiment 112, wherein another therapy is a chemotherapy, a radiation therapy, an antibody, a cytokine, an immune checkpoint inhibitor, or a bispecific polypeptide used in immune-oncology therapy.

Embodiment 120. Use of a composition comprising an effective amount of nucleated cells in the manufacture of a medicament for stimulating an immune response to mutated Ras, wherein the composition comprises an effective amount of the composition of any one of embodiments 56-106.

Embodiment 121. Use of a composition comprising an effective amount of nucleated cells in the manufacture of a medicament for reducing tumor growth in an individual, wherein the composition comprises an effective amount of the composition of any one of embodiments 56-106.

Embodiment 122. The use of embodiment 120 or 121, wherein the individual has cancer.

Embodiment 123. Use of a composition comprising an effective amount of nucleated cells in the manufacture of a medicament for treating cancer in an individual, wherein the composition comprises an effective amount of the composition of any one of embodiments 56-106.

Embodiment 124. The use of embodiment 122 or 123, wherein the cancer is a pancreatic cancer, a colon cancer, a small intestine cancer, a biliary tract cancer, an endometrial cancer, a lung cancer, a skin cancer, an ovarian cancer, a stomach cancer, an esophageal cancer, a cervical cancer or a urinary tract cancer.

Embodiment 125. The use of any one of embodiments 120-124, wherein the composition further comprises an adjuvant.

Embodiment 126. The use of any one of embodiments 120-125, wherein the composition is formulated for administration in conjunction with an adjuvant.

Embodiment 127. The use of embodiment 126, wherein the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist.

Embodiment 128. The use of any one of embodiments 120-127, wherein the composition comprising nucleated cells is administered a plurality of times.

Embodiment 129. The use of any one of embodiments 120-128, wherein the composition is administered intravenously.

Embodiment 130. The use of any one of embodiments 120-129, wherein the individual is a human.

Embodiment 131. The use of any one of embodiments 120-130, wherein the composition is administered prior to, concurrently with, or following administration of another therapy.

Embodiment 132. The use of embodiment 131, wherein another therapy is a chemotherapy, a radiation therapy, an antibody, a cytokine, an immune checkpoint inhibitor, or a bispecific polypeptide used in immune-oncology therapy.

Embodiment 133. A kit for use in the method of any one of embodiments 1-55.

Embodiment 134. A kit comprising the composition of any one of embodiments 56-106.

Embodiment 135. The kit of embodiment 133 or 134, wherein the kit further comprises one or more of buffers, diluents, filters, needles, syringes, or package inserts with instructions for administering the composition to an individual to stimulate an immune response to a mutated K-Rad, reduce tumor growth and/or treat cancer.

Embodiment 136. A method for producing a composition of nucleated cells comprising a mutated Ras antigen; the method comprising introducing the mutated Ras antigen to the nucleated cell intracellularly.

Embodiment 137. The method of embodiment 136, wherein introducing the mutated Ras antigen to the nucleate cell intracellularly comprises a) passing a cell suspension comprising input nucleated cells through a cell-deforming constriction, wherein a diameter of the constriction is a function of a diameter of the input nucleated cells in the suspension, thereby causing perturbations of the input nucleate cells large enough for the mutated Ras antigen to pass through to form a perturbed input nucleated cells; and
b) incubating the perturbed input nucleated cells with the mutated Ras antigen for a sufficient time to allow the mutated Ras antigen to enter the perturbed input nucleated cells; thereby generating nucleated cells comprising the mutated Ras antigen.

Embodiment 138. The method of embodiment 136, wherein introducing the mutated Ras antigen to the nucleated cell intracellularly comprises a) passing a cell suspension comprising input nucleated cells through a cell-deforming constriction, wherein a diameter of the constriction is a function of a diameter of the input nucleated cells in the suspension, thereby causing perturbations of the input nucleated cells large enough for a nucleic acid encoding the mutated Ras antigen to pass through to form a perturbed input nucleated cells; and
b) incubating the perturbed input nucleated cells with the nucleic acid encoding the mutated Ras antigen for a sufficient time to allow the nucleic acid encoding the mutated Ras antigen to enter the perturbed input nucleated cells, wherein the nucleic acid expressed the mutated Ras antigen; thereby generating nucleated cells comprising the mutated Ras antigen.

Embodiment 139. The method of any one of embodiments 136-138, wherein the width of the constriction is about 10% to about 99% of the mean diameter of the input nucleated cells.

Embodiment 140. The method of any one of embodiments 136-139, wherein the width of the constriction is about 3.5 μm to about 4.2 μm or about 3.5 μm to about 4.8 μm or about 3.5 μm to about 6 μm or about 4.2 μm to about 4.8 μm or about 4.2 μm to about 6 μm.

Embodiment 141. The method of any one of embodiments 136-140, wherein the width of the constriction is about 3.5 μm.

Embodiment 142. The method of any one of embodiments 136-141, wherein the width of the constriction is about 4.5 μm.

Embodiment 143. The method of any one of embodiments 136-142, wherein the cell suspension comprising the plurality of input nucleated cells are passed through multiple constrictions wherein the multiple constrictions are arranged in series and/or in parallel.

Embodiment 144. The method of any one of embodiments 136-143, wherein the method further comprising conditioning the nucleated cells with an adjuvant to form conditioned cells.

Embodiment 145. The method of embodiment 144, wherein the nucleated cells are incubated with the adjuvant for about 1 hour to about 24 hours, about 2 hours to about 10 hours, about 3 hours to about 6 hours, or about 4 hours for the cells to condition.

Embodiment 146. The method of embodiment 144 or 145, wherein the nucleated cells are conditioned before or after introducing the mutated Ras antigen into the nucleated cells.

EXAMPLES

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

Example 1

In order to determine if immune cells of a specific HLA haplotype SQZ-loaded with a mutant K-Ras antigen can induce an antigen-specific T cell response, human donor HLA-A*11$^{+}$ PBMCs were SQZ-loaded with K-Ras G12D synthetic long peptides and the ability to stimulate G12D-specific responder T cells was measured using an IFN-γ ELISPOT assay.

Methods

Human PBMCs from HLA-A*11$^{+}$ donor were prepared at a density of 10×10$^{6}$/mL, and SQZ-processed at room temperature through a constriction of 4.5 μm width, 10 μm length and 70 μm depth at 60 psi with 100 μM of the respective K-Ras G12D synthetic long peptide (either G12D$^{1-16}$, G12D$^{2-19}$, G12D$^{2-22}$, G12D$^{2-29}$) or with vehicle control (DMSO) in RPMI medium. Following SQZ-processing, the SQZ-loaded PBMCs were centrifuged, and the supernatant was discarded. The cells were subsequently washed once in R10 medium (RPMI+10% FCS+1% Pen/Strep), then washed twice in CTL medium (supplemented with 1% glutamine), before resuspension in fresh CTL medium (supplemented with 1% glutamine).

2×10$^{5}$ SQZ-loaded PBMCs were then placed in co-culture with 5×10$^{4}$ K-Ras G12D responder T cells (generated in transgenic mice) in an IFN-γ ELISPOT plate. As a positive control, 10 μM K-Ras G12D$^{7-16}$ peptide containing the minimal epitope was added directly to untreated PBMCs and responder cells in the ELISPOT plate (peptide spike). The plate was incubated overnight at 37° C. and then developed/quantified according to manufacturer's instructions.

Results

As shown in FIG. 1, HLA-A*11$^{+}$ human PBMCs SQZ-loaded with G12D$^{1-16}$, G12D$^{2-19}$, G12D$^{2-22}$, or G12D$^{2-29}$ SLP led to significant increases in IFN-γ expressing by K-Ras-G12D responder T cells upon co-culture. The results demonstrate HLA-A*11$^{+}$ human PBMCs SQZ-loaded with a mutant K-Ras antigen can induce an antigen-specific T cell response.

Example 2

In order to determine if immune cells of a specific HLA haplotype SQZ-loaded with a mutant K-Ras antigen can induce an antigen-specific T cell response, human donor HLA-A*11$^{+}$ PBMCs were SQZ-loaded with K-Ras G12D synthetic long peptides and the ability to stimulate G12D-specific responder T cells was measured using an IFN-γ ELISPOT assay. The effects of PBMCs SQZ-loaded with K-Ras G12D were compared to PBMCs SQZ-loaded with wild type K-Ras to determine the mutation-specificity of the antigen-specific T cell response.

Methods

Human PBMCs from HLA-A*11$^{+}$ donor were prepared at a density of 10×10$^{6}$/mL, and SQZ processed at room temperature through a constriction of 4.5 μm width, 10 μm length and 70 μm depth at 60 psi with 100 μM of the respective K-Ras synthetic long peptide (either wild type K-Ras$^{1-16}$ or K-Ras-G12D$^{1-16}$) or with vehicle control (DMSO) in RPMI medium. Following SQZ-processing, the SQZ-loaded PMBCs were centrifuged, and the supernatant was discarded. The cells were subsequently washed once in R10 medium (RPMI+10% FCS+1% Pen/Strep), then washed twice in CTL medium (supplemented with 1% glutamine), before resuspension in fresh CTL medium (supplemented with 1% glutamine).

2×10$^{5}$ SQZ-loaded PBMCs were then placed in co-culture with 5×10$^{4}$ K-Ras G12D responder T cells (generated in transgenic mice) in an IFN-γ ELISPOT plate. As a positive control, 10 μM K-Ras G12D$^{7-16}$ peptide containing the minimal epitope was added directly to untreated PBMCs and responder cells in the ELISPOT plate (peptide spike). 10 μM wild type K-Ras7-16 peptide was added to PBMCs and responder cells as another positive control (peptide spike). The plate was incubated overnight at 37° C. and then developed/quantified according to manufacturer's instructions.

Results

Figure 2:
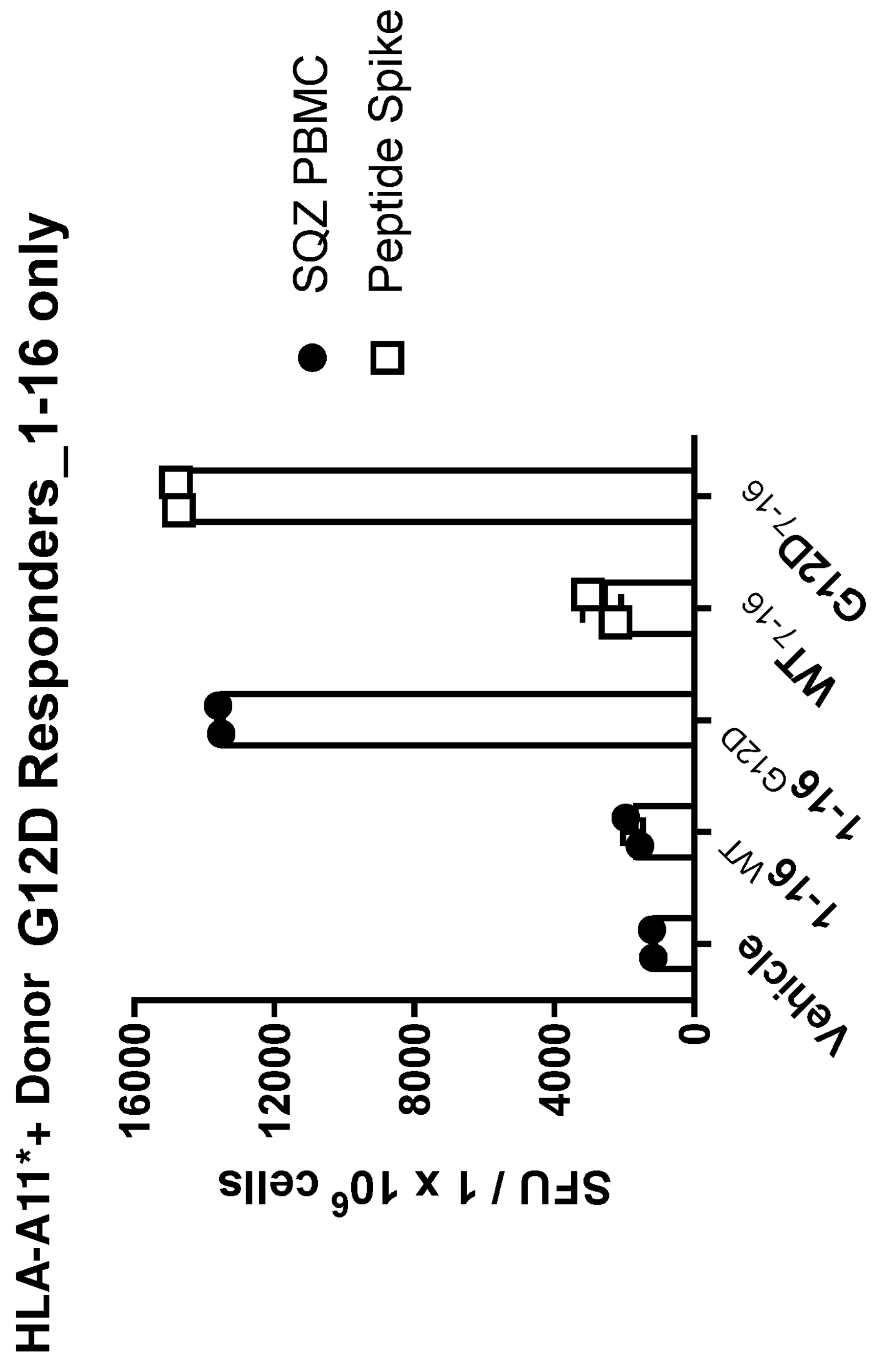
FIG. 2 is a graph showing increased amount of IFN-γ expressing K-Ras-G12D responder T cells upon co-culture with PBMCs loaded with mutated K-Ras-G12D$^{1-16}$.

As shown in FIG. 2, HLA-A*11$^{+}$ human PBMCs SQZ-loaded with G12D$^{1-16}$ SLP led to significant increases in IFN-γ expressing K-Ras-G12D responder T cells upon co-culture, whereas human PBMCs SQZ-loaded with wild type K-Ras$^{1-16}$ did not elicit increases in IFN-γ expressing T cells compared to vehicle control. The results demonstrate HLA-A*11$^{+}$ human PBMCs SQZ-loaded with a mutant K-Ras antigen can induce antigen-specific T cell response that is also mutation specific.

Example 3

In order to determine if immune cells of a specific HLA haplotype SQZ-loaded with a mutant K-Ras antigen can induce an antigen-specific T cell response, human donor HLA-A*11$^{+}$ PBMCs were SQZ-loaded with K-Ras G12D synthetic long peptides and the ability to stimulate G12D-specific T responder cells were measured using an IFN-γ ELISPOT assay. The effects of PBMCs SQZ-loaded with K-Ras G12D were compared to PBMCs SQZ-loaded with wild type K-Ras to determine the mutation-specificity of the antigen-specific T cell response.

Methods

Human PBMCs from HLA-A*11$^{+}$ donor (donor 339) were prepared at a density of 10×10$^{6}$/mL, SQZ processed at room temperature through a constriction of 4.5 μm width, 10 μm length and 70 μm depth at 60 psi with 100 μM of the respective K-Ras synthetic long peptide (either wild type K-Ras$^{2-22}$ or K-Ras G12D$^{2-22}$) or with vehicle control (DMSO) in RPMI medium. Following SQZ-processing, the SQZ-loaded PMBCs were centrifuged, and the supernatant was discarded. The cells were subsequently washed once in R10 medium (RPMI+10% FCS+1% Pen/Strep), then washed twice in CTL medium (supplemented with 1% glutamine), before resuspension in fresh CTL medium (supplemented with 1% glutamine).

2×10$^{5}$ SQZ-loaded PBMCs were then placed in co-culture with 5×10$^{4}$ K-Ras G12D responder T cells (generated in transgenic mice) in an IFN-γ ELISPOT plate. As a positive control, 10 μM K-Ras G12D$^{7-16}$ peptide containing the minimal epitope was added directly to untreated PBMCs and responder cells in the ELISPOT plate (peptide spike). The plate was incubated overnight at 37° C. and then developed/quantified according to manufacturer's instructions.

Results

Figure 3:
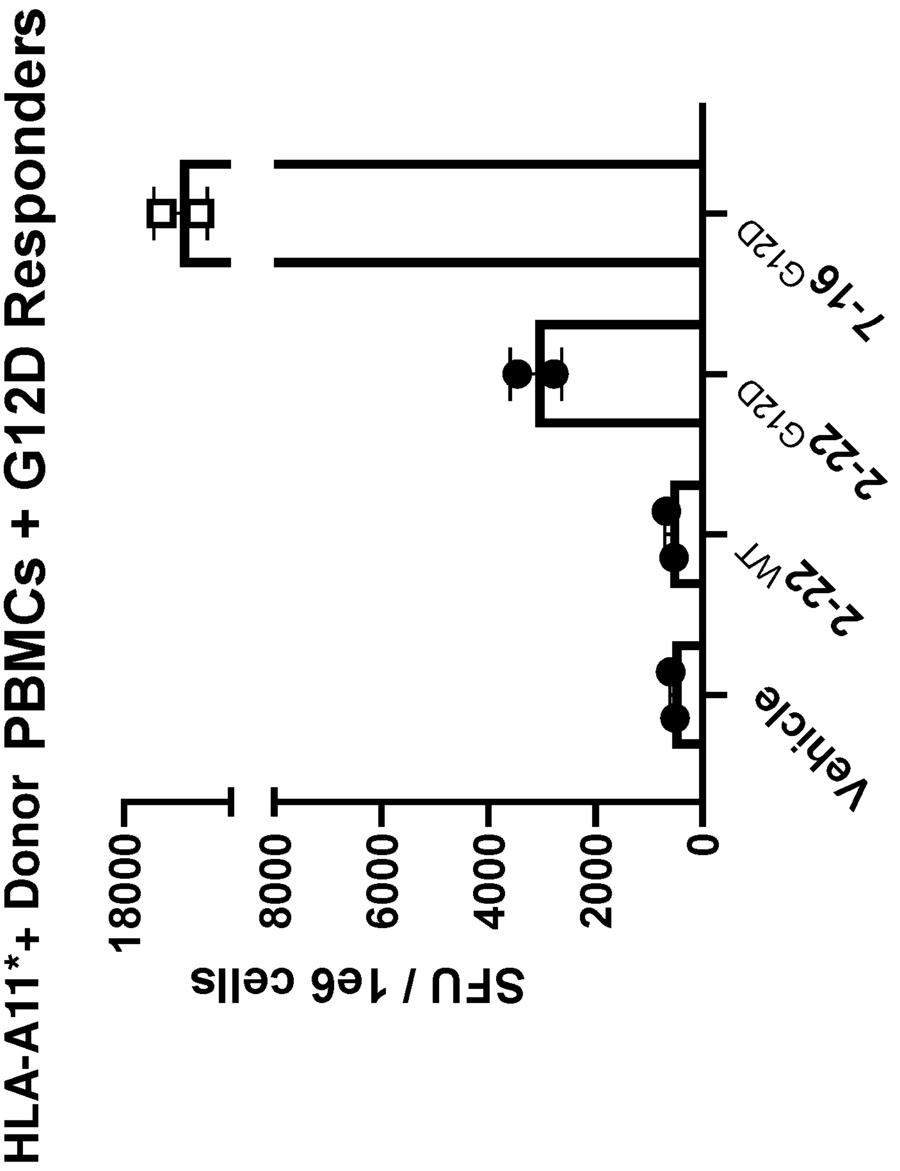
FIG. 3 is a graph showing increased amount of IFN-γ expressing K-Ras-G12D responder T cells upon co-culture with PBMCs loaded with mutated K-Ras-G12D$^{2-22}$.

As shown in FIG. 3, HLA-A*11$^{+}$ human PBMCs SQZ-loaded with G12D$^{2-22}$ SLP led to significantly increased IFN-γ secretion by K-Ras-G12D responder T cells upon co-culture, whereas human PBMCs SQZ-loaded with wild type K-Ras$^{2-22}$ did not elicit increased IFN-γ secretion compared to vehicle control. The results demonstrate HLA-A*11$^{+}$ human PBMCs SQZ-loaded with a mutant K-Ras antigen can induce antigen-specific T cell response that is also mutation specific.

Example 4

In order to determine if immune cells of a specific HLA haplotype SQZ-loaded with a mutant K-Ras antigen can induce an antigen-specific T cell response, human donor HLA-A*11$^{+}$ PBMCs were SQZ-loaded with K-Ras G12V synthetic long peptides and the ability to stimulate G12V-specific T responder cells were measured using an IFN-γ ELISPOT assay.

Methods

Human PBMCs from HLA-A*11$^{+}$ donor (donor 296) were prepared at a density of 10×10$^{6}$/mL, SQZ processed at room temperature through a constriction of 4.5 μm width, 10 μm length and 70 μm depth at 60 psi with 100 μM of the respective K-Ras synthetic long peptide (G12V$^{1-16}$, G12V$^{2-19}$) or with vehicle control (DMSO) in RPMI medium. Following SQZ-processing, the SQZ-loaded PMBCs were centrifuged, and the supernatant was discarded. The cells were subsequently washed once in R10 medium (RPMI+10% FCS+1% Pen/Strep), then washed twice in CTL medium (supplemented with 1% glutamine), before resuspension in fresh CTL medium (supplemented with 1% glutamine).

2×10$^{5}$ SQZ-loaded PBMCs were then placed in co-culture with 5×10$^{4}$ K-Ras G12V responder T cells (generated in transgenic mice) in an IFN-γ ELISPOT plate. As a positive control, 10 μM K-Ras G12V$^{7-16}$ peptide containing the minimal epitope was added directly to untreated PBMCs and responder cells in the ELISPOT plate (peptide spike). The plate was incubated overnight at 37° C. and then developed/quantified according to manufacturer's instructions.

Results

Figure 4:
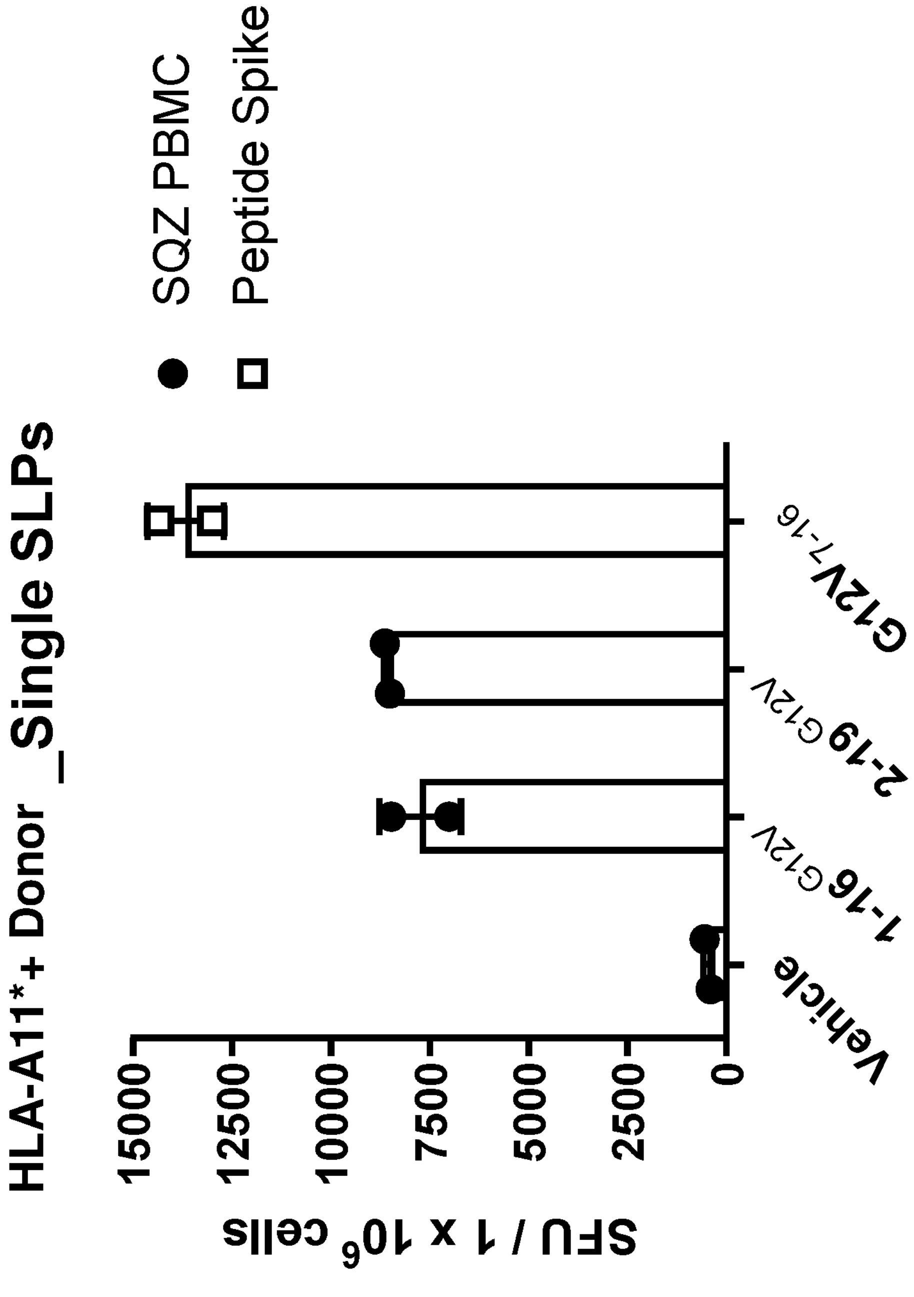
FIG. 4 is a graph showing increased amount of IFN-γ expressing K-Ras-G12V responder T cells upon co-culture with PBMCs loaded with mutated K-Ras-G12V$^{1-16}$ and mutated K-Ras-G12V$^{2-19}$.

As shown in FIG. 4, HLA-A*11$^{+}$ human PBMCs SQZ-loaded with either G12V$^{1-16}$ or G12V$^{2-19}$ SLP led to significantly increased IFN-γ secretion by K-Ras-G12V responder T cells upon co-culture. The results demonstrate HLA-A*11$^{+}$ human PBMCs SQZ-loaded with a mutant K-Ras antigen can induce antigen-specific T cell response.

Example 5

In order to determine if immune cells of a specific HLA haplotype SQZ-loaded with a mutant K-Ras antigen can induce an antigen-specific T cell response, human donor HLA-A*11$^{+}$ PBMCs were SQZ-loaded with K-Ras G12V synthetic long peptides and the ability to stimulate G12V-specific T responder cells were measured using an IFN-γ ELISPOT assay.

Methods

Human PBMCs from HLA-A*11$^{+}$ donor were prepared at a density of 10×10$^{6}$/mL, SQZ processed at room temperature through a constriction with 4.5 μm width, 10 μm length and 70 μm depth at 60 psi with 100 μM of the respective K-Ras synthetic long peptide (K-Ras G12V$^{3-17}$, K-Ras G12V$^{3-42}$) or with vehicle control (DMSO) in RPMI medium. An irrelevant synthetic long peptide (HPV-E7.6) was used as a negative control. Following SQZ-processing, the SQZ-loaded PMBCs were centrifuged, and the supernatant was discarded. The cells were subsequently washed once in R10 medium (RPMI+10% FCS+1% Pen/Strep), then washed twice in CTL medium (supplemented with 1% glutamine), before resuspension in fresh CTL medium (supplemented with 1% glutamine).

2×10$^{5}$ SQZ-loaded PBMCs were then placed in co-culture with 5×10$^{4}$ K-Ras G12V responder T cells (generated in transgenic mice) in an IFN-γ ELISPOT plate. As a positive control, 10 μM K-Ras G12V$^{7-16}$ peptide containing the minimal epitope was added directly to untreated PBMCs and responder cells in the ELISPOT plate (peptide spike). The plate was incubated overnight at 37° C. and then developed/quantified according to manufacturer's instructions.

Results

Figure 5:
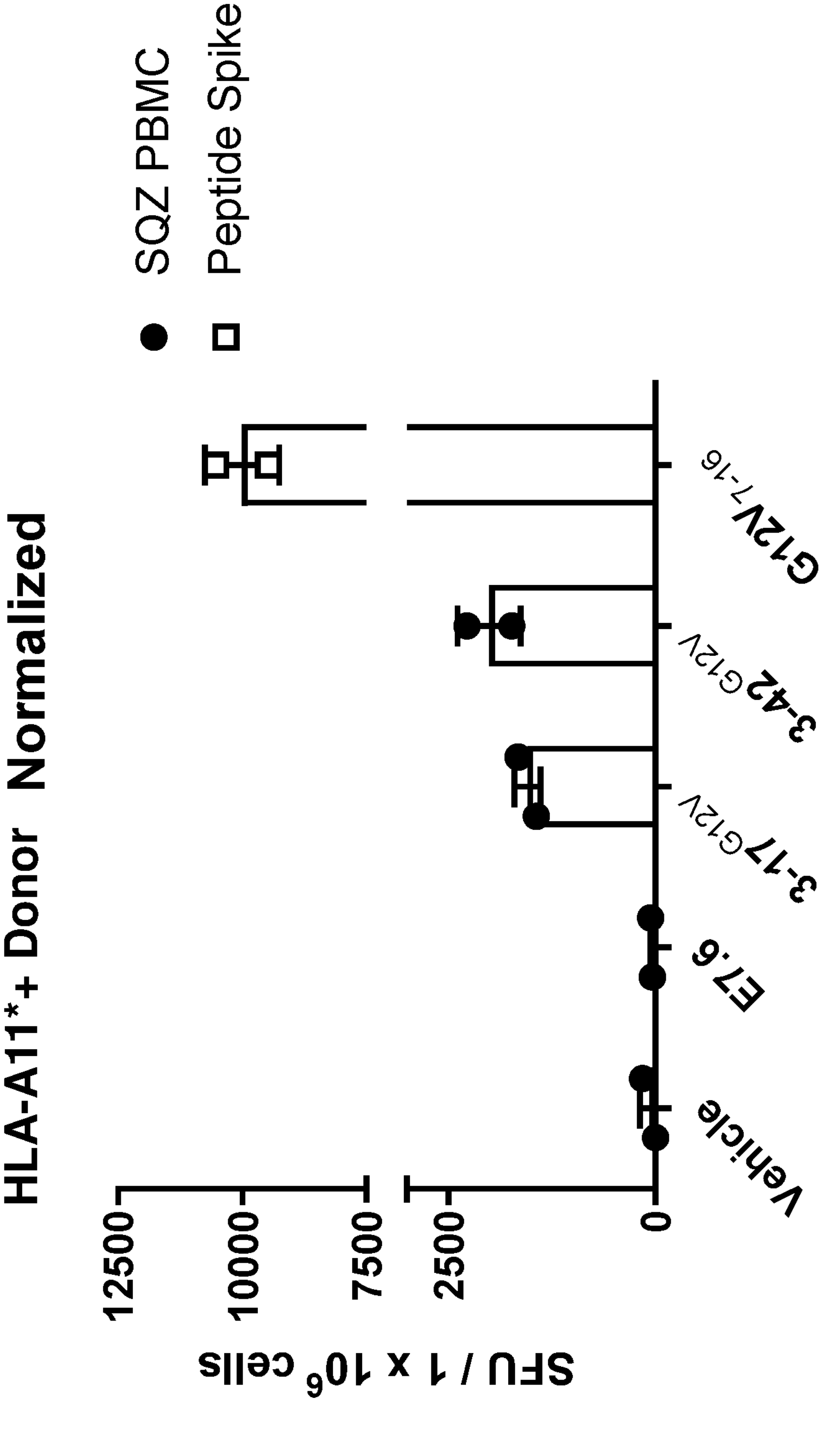
FIG. 5 is a graph showing increased amount of IFN-γ expressing K-Ras-G12V responder T cells upon co-culture with PBMCs loaded with mutated K-Ras-G12V$^{3-17}$ and mutated K-Ras-G12V$^{3-42}$.

As shown in FIG. 5, HLA-A*11$^{+}$ human PBMCs SQZ-loaded with G12V$^{3-17}$ or G12V$^{3-42}$ SLP led to significant increases in IFN-γ expressing K-Ras-G12V responder T cells upon co-culture. In contrast, PBMCs SQZ-loaded with E7.6 did not lead to any increases in IFN-γ expressing by K-Ras-G12V responder T cells. The results demonstrate HLA-A*11$^{+}$ human PBMCs SQZ-loaded with a mutant K-Ras antigen can induce antigen-specific T cell response.

Example 6

In order to determine if immune cells of a specific HLA haplotype SQZ-loaded with a mutant K-Ras antigen can induce an antigen-specific T cell response, human donor HLA-A*11$^{+}$ PBMCs were SQZ-loaded with K-Ras G12V synthetic long peptides and the ability to stimulate G12V-specific T responder cells were measured using an IFN-γ ELISPOT assay. The effects of PBMCs SQZ-loaded with K-Ras G12V were compared to PBMCs SQZ-loaded with wild type K-Ras to determine the mutation-specificity of the antigen-specific T cell response.

Methods

Human PBMCs from HLA-A*11$^{+}$ donor were prepared at a density of 10× 106/mL, SQZ processed at room temperature through a constriction of 4.5 μm width, 10 μm length and 70 μm depth at 60 psi with 100 μM of the respective K-Ras synthetic long peptide (wild type K-Ras$^{1-16}$, G12V$^{1-16}$, wild type K-Ras$^{2-22}$, or G12V$^{2-22}$) or with vehicle control (DMSO) in RPMI medium. Following SQZ-processing, the SQZ-loaded PMBCs were centrifuged, and the supernatant was discarded. The cells were subsequently washed once in R10 medium (RPMI+10% FCS+1% Pen/Strep), then washed twice in CTL medium (supplemented with 1% glutamine), before resuspension in fresh CTL medium (supplemented with 1% glutamine).

$2\times10^5$ SQZ-loaded PBMCs were then placed in co-culture with $5\times10^4$ K-Ras G12V responder T cells (generated in transgenic mice) in an IFN-γ ELISPOT plate. As a positive control, 10 μM K-Ras G12V$^{7-16}$ peptide containing the minimal epitope was added directly to untreated PBMCs and responder cells in the ELISPOT plate (peptide spike). The plate was incubated overnight at 37° C. and then developed/quantified according to manufacturer's instructions.

Results

Figure 6:
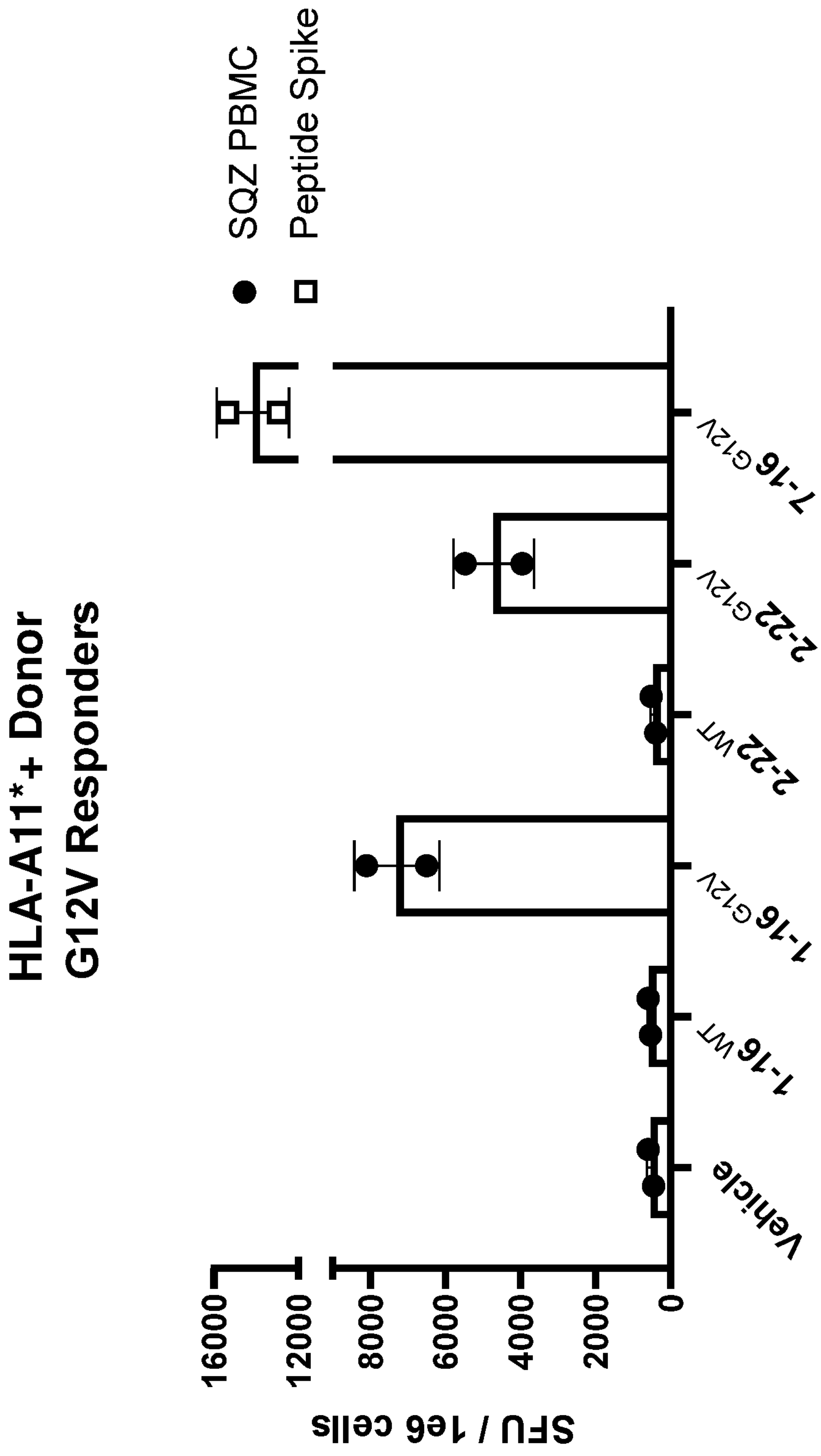
FIG. 6 is a graph showing increased amount of IFN-γ expressing K-Ras-G12V responder T cells upon co-culture with PBMCs loaded with mutated K-Ras-G12V$^{1-16}$ and mutated K-Ras-G12V$^{2-22}$.

As shown in FIG. 6, HLA-A*11$^+$ human PBMCs SQZ-loaded with G12V$^{1-16}$ G12V$^{2-22}$ SLP led to significant increases in IFN-γ expressing K-Ras-G12V responder T cells upon co-culture, whereas human PBMCs SQZ-loaded with either wild type K-Ras1-16 or wild type K-Ras$^{2-22}$ did not elicit increases in IFN-γ expressing T cells compared to vehicle control. The results demonstrate HLA-A*11$^+$ human PBMCs SQZ-loaded with a mutant K-Ras antigen can induce antigen-specific T cell response that is also mutation specific.

Example 7

In order to determine if immune cells of a specific HLA haplotype SQZ-loaded with one or more mutant K-Ras antigens can induce an antigen-specific T cell response, human donor HLA-A*11$^+$ PBMCs were SQZ-loaded with a K-Ras-G12D SLP, or a combination of K-Ras G12V and K-Ras-G12D SLPs, and the ability to stimulate G12D-specific T responder cells were measured using an IFN-γ ELISPOT assay.

Methods

Human PBMCs from HLA-A*11$^+$ donor were prepared at a density of 10× 106/mL, SQZ processed at room temperature through a constriction with 4.5 μm width, 10 μm length and 70 μm depth at 60 psi with 100 μM of a K-Ras G12D$^{1-16}$ synthetic long peptide, or a combination of two K-Ras synthetic long peptides which were each at 100 μM (G12D$^{1-16}$ plus G12V$^{1-16}$ or G12D$^{1-16}$ plus G12V$^{2-19}$) or vehicle control (DMSO) in RPMI medium. Following SQZ-processing, the SQZ-loaded PMBCs were centrifuged, and the supernatant was discarded. The cells were subsequently washed once in R10 medium (RPMI+10% FCS+1% Pen/Strep), then washed twice in CTL medium (supplemented with 1% glutamine), before resuspension in fresh CTL medium (supplemented with 1% glutamine).

$2\times10^5$ SQZ-loaded PBMCs were then placed in co-culture with $5\times10^4$ K-Ras G12D responder T cells (generated in transgenic mice) in an IFN-γ ELISPOT plate. As a positive control, 10 μM K-Ras G12D$^{7-16}$ peptide containing the minimal epitope was added directly to untreated PBMCs and responder cells in the ELISPOT plate (peptide spike). The plate was incubated overnight at 37° C. and then developed/quantified according to manufacturer's instructions.

Results

Figure 7:
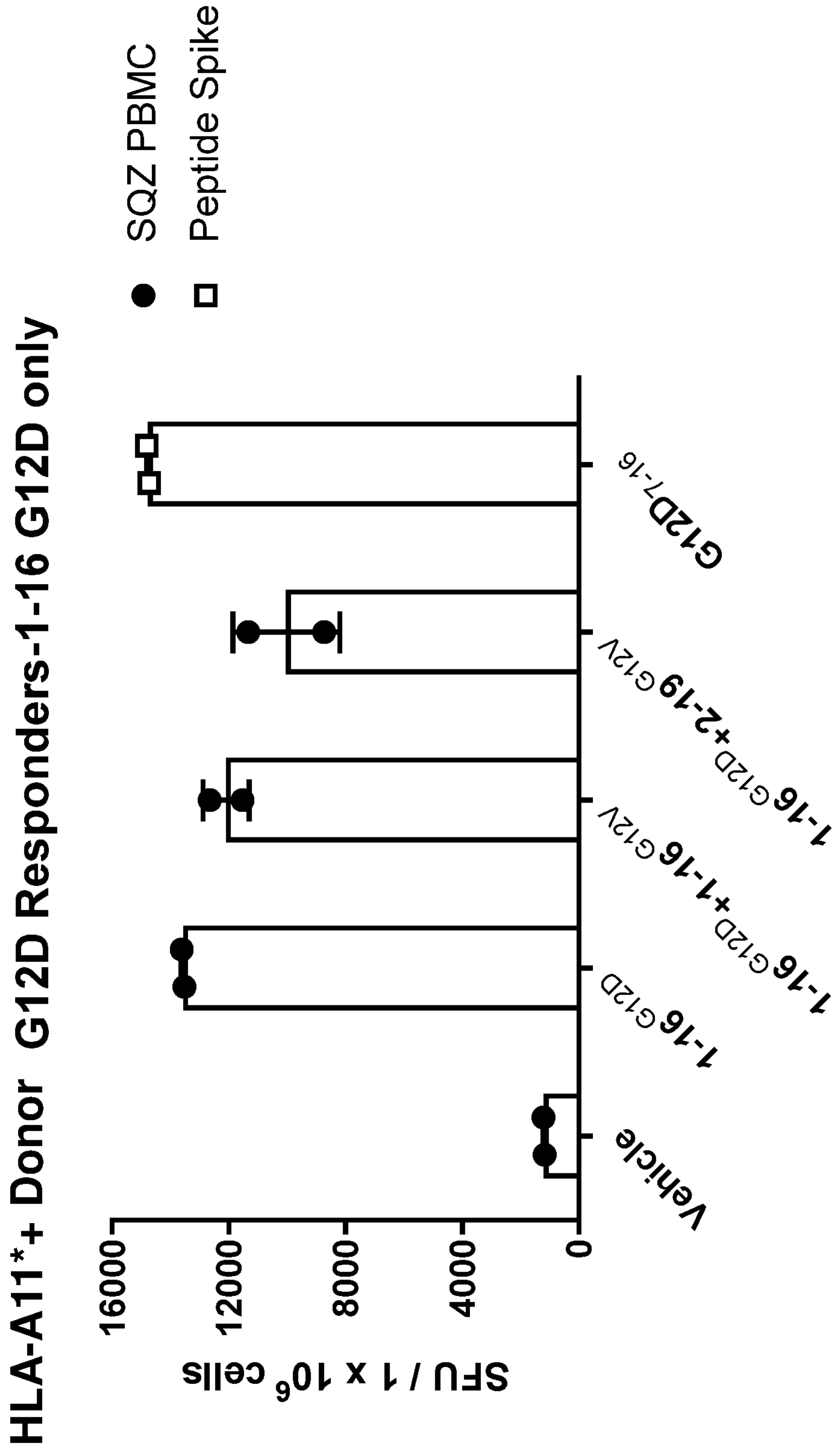
FIG. 7 is a graph showing increased amount of IFN-γ expressing K-Ras-G12V responder T cells upon co-culture with PBMCs loaded with mutated K-Ras-G12D$^{1-16}$ plus mutated K-Ras-G12V$^{1-16}$ or mutated K-Ras-G12D$^{1-16}$ and mutated K-Ras-G12V$^{2-19}$.

As shown in FIG. 7, HLA-A*11$^+$ human PBMCs SQZ-loaded with either the combination of G12D$^{1-16}$ plus G12V$^{1-16}$ or G12D$^{1-16}$ plus G12V$^{2-19}$ SLPs led to significant increases in IFN-γ expressing K-Ras-G12D responder T cells upon co-culture, similar to that induced by PBMCs SQZ-loaded with G12D$^{1-16}$ alone. The results demonstrate HLA-A*11$^+$ human PBMCs SQZ-loaded with a combination of mutant K-Ras-G12D and K-Ras-G12V antigens can induce antigen-specific T cell response to a similar extent as PBMCs SQZ-loaded with a single K-Ras-G12D antigen (G12D$^{1-16}$).

Example 8

In order to determine if immune cells of a specific HLA haplotype SQZ-loaded with one or more mutant K-Ras antigens can induce an antigen-specific T cell response, human donor HLA-A*11$^+$ PBMCs were SQZ-loaded with the combination of K-Ras G12V plus G12D synthetic long peptides and the ability to stimulate G12V-specific T responder cells were measured using an IFN-γ ELISPOT assay.

Methods

Human PBMCs from HLA-A*11$^+$ donor were prepared at a density of $10\times10^6$/mL, SQZ processed at room temperature through a constriction of 4.5 μm width, 10 μm length and 70 μm depth at 60 psi with 100 μM of a single K-Ras synthetic long peptide (G12V$^{1-16}$ or G12V$^{2-19}$), or a combination of two K-Ras synthetic long peptides which are each at 100 μM (G12V$^{1-16}$ plus G12D$^{1-16}$ or G12V$^{2-19}$ plus G12D$^{1-16}$) or vehicle control (DMSO) in RPMI medium. Following SQZ-processing, the SQZ-loaded PMBCs were centrifuged, and the supernatant was discarded. The cells were subsequently washed once in R10 medium (RPMI+10% FCS+1% Pen/Strep), then washed twice in CTL medium (supplemented with 1% glutamine), before resuspension in fresh CTL medium (supplemented with 1% glutamine).

$2\times10^5$ SQZ-loaded PBMCs were then placed in co-culture with $5\times10^4$ K-Ras G12D responder T cells (generated in transgenic mice) in an IFN-γ ELISPOT plate. As a positive control, 10 μM K-Ras G12V$^{7-16}$ peptide containing the minimal epitope was added directly to untreated PBMCs and responder cells in the ELISPOT plate (peptide spike). The plate was incubated overnight at 37° C. and then developed/quantified according to manufacturer's instructions.

Results

Figure 8:
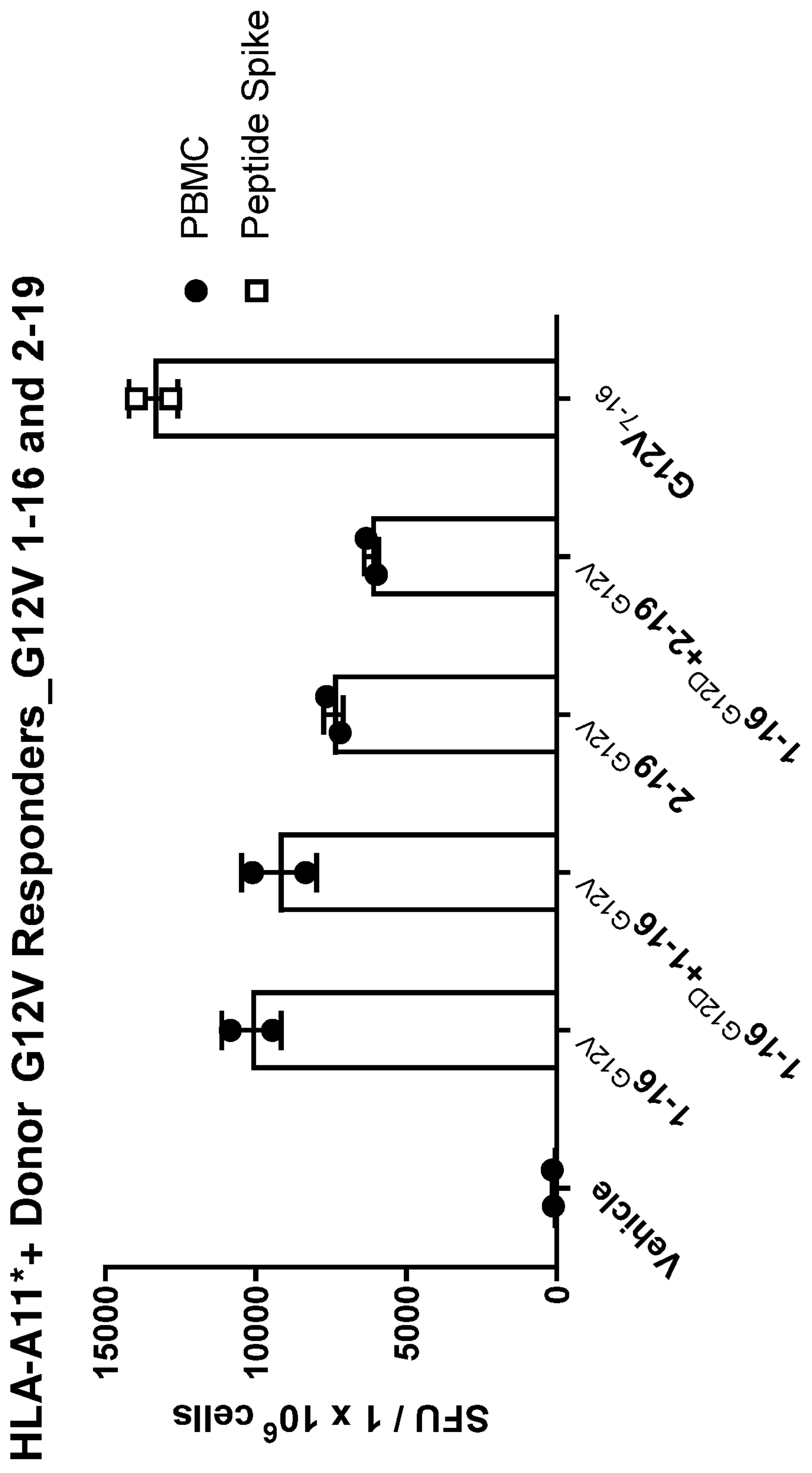
FIG. 8 is a graph showing increased amount of IFN-γ expressing K-Ras-G12V responder T cells upon co-culture with PBMCs loaded with K-Ras-G12D$^{1-16}$ plus mutated K-Ras-G12V$^{1-16}$ or mutated K-Ras-G12D$^{1-16}$ and mutated K-Ras-G12V$^{2-19}$.

As shown in FIG. 8, HLA-A*11$^+$ human PBMCs SQZ-loaded with the combination of G12V$^{1-16}$ plus G12D$^{1-16}$ or G12V$^{2-19}$ plus G12D$^{1-16}$ SLP led to significant increases in IFN-γ expressing K-Ras-G12V responder T cells upon co-culture, similar to that induced by PBMCs SQZ-loaded with G12V$^{1-16}$ alone or by PBMCs SQZ-loaded with G12V$^{2-19}$ alone. The results demonstrate HLA-A*11$^+$ human PBMCs SQZ-loaded with a combination of mutant K-Ras-G12D and K-Ras-G12V antigens can induce antigen-specific T cell response to a similar extent as PBMCs SQZ-loaded with a single K-Ras-G12V antigen (G12V$^{2-19}$).

Example 9

In order to generate HLA-A*11 cell responders specific to respective mutant K-Ras antigens, HLA-A*11 transgenic mice were vaccinated with a mutant K-Ras peptide and the ability of immune cells extracted from the vaccinated mice to respond to mutant K-Ras antigen challenge was measured using an IFN-γ ELISPOT assay.

Methods

HLA-A*11 transgenic mice were vaccinated twice (prime/boost; 1 mouse) or 3 times (prime/boost/boost; 3 mice) at 2-week intervals with an emulsion of K-Ras G12C$^{7-16}$ peptide, hepatitis B virus core peptide (TPPAY-RPPNAPIL; SEQ ID NO:18), and incomplete Freund's Adjuvant. One week after the final vaccination, mice were euthanized, where the spleens and draining lymph nodes were extracted, and tissue extracts were dissociated into single cell suspensions.

In a first experiment, cell extracts were then plated on an ELISpot plate, and cultured overnight at 37° C. with medium only (negative control), or with medium containing wild type K-Ras$^{7-16}$ peptide, or K-Ras G12C$^{7-16}$ peptide. The plate was then developed/quantified according to manufacturer's instructions.

Alternatively, cells extracts were cultured for 6 days at 37° C. in the presence of K-Ras G12C$^{7-16}$ peptide. Following this incubation, cells were then plated on an ELISpot plate, and cultured overnight at 37° C. with medium only (negative control), or with medium containing wild type K-Ras$^{7-16}$ peptide, or K-Ras G12C$^{7-16}$ peptide. The plate was then developed/quantified according to manufacturer's instructions.

Results

Figure 9A:
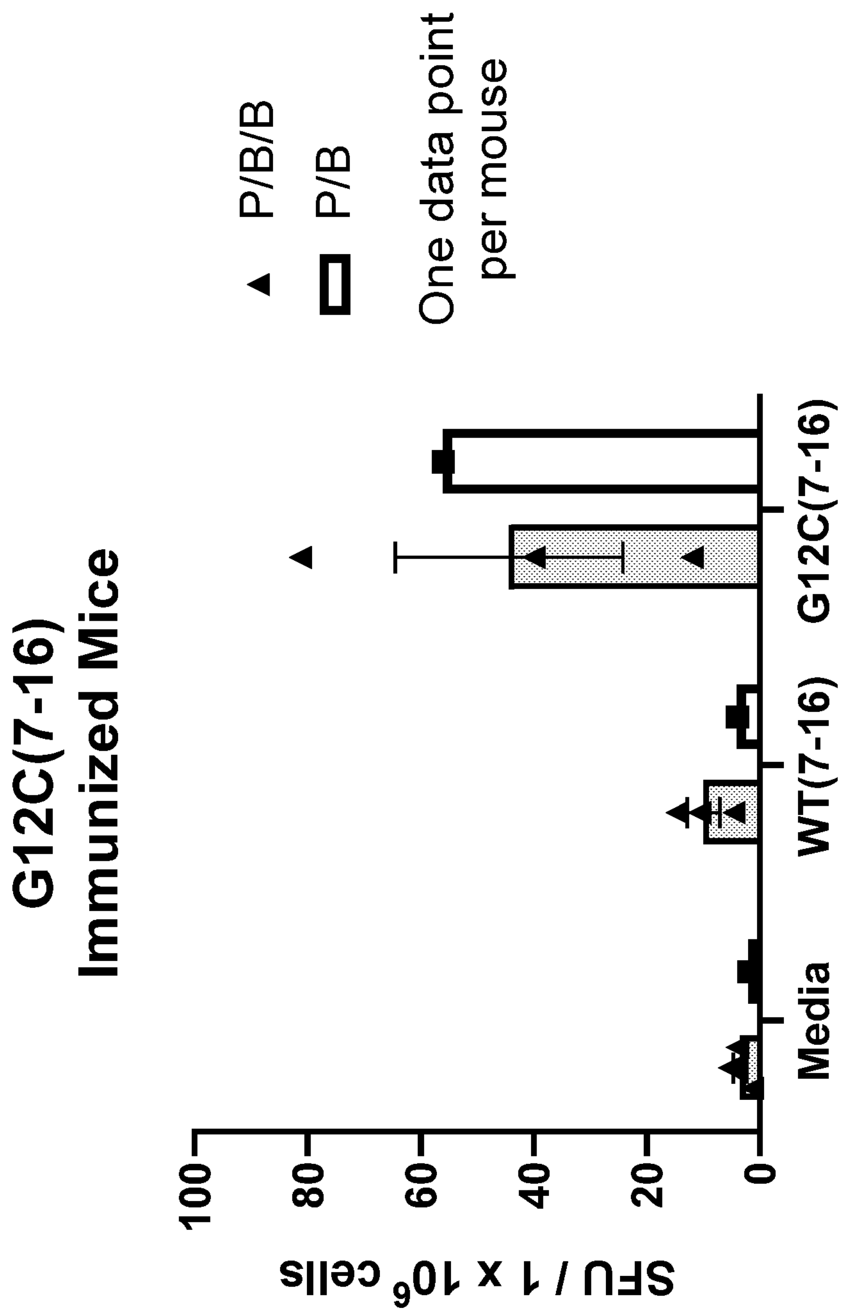
FIG. 9A is a graph showing increased amount of IFN-γ expressing cells upon co-culture of mutant K-Ras G12C$^{7-16}$ peptide and immune cells extracted from HLA-A*11$^{+}$ transgenic mice vaccinated with an emulsion of mutated K-Ras G12C$^{7-16}$.
Figure 9B:
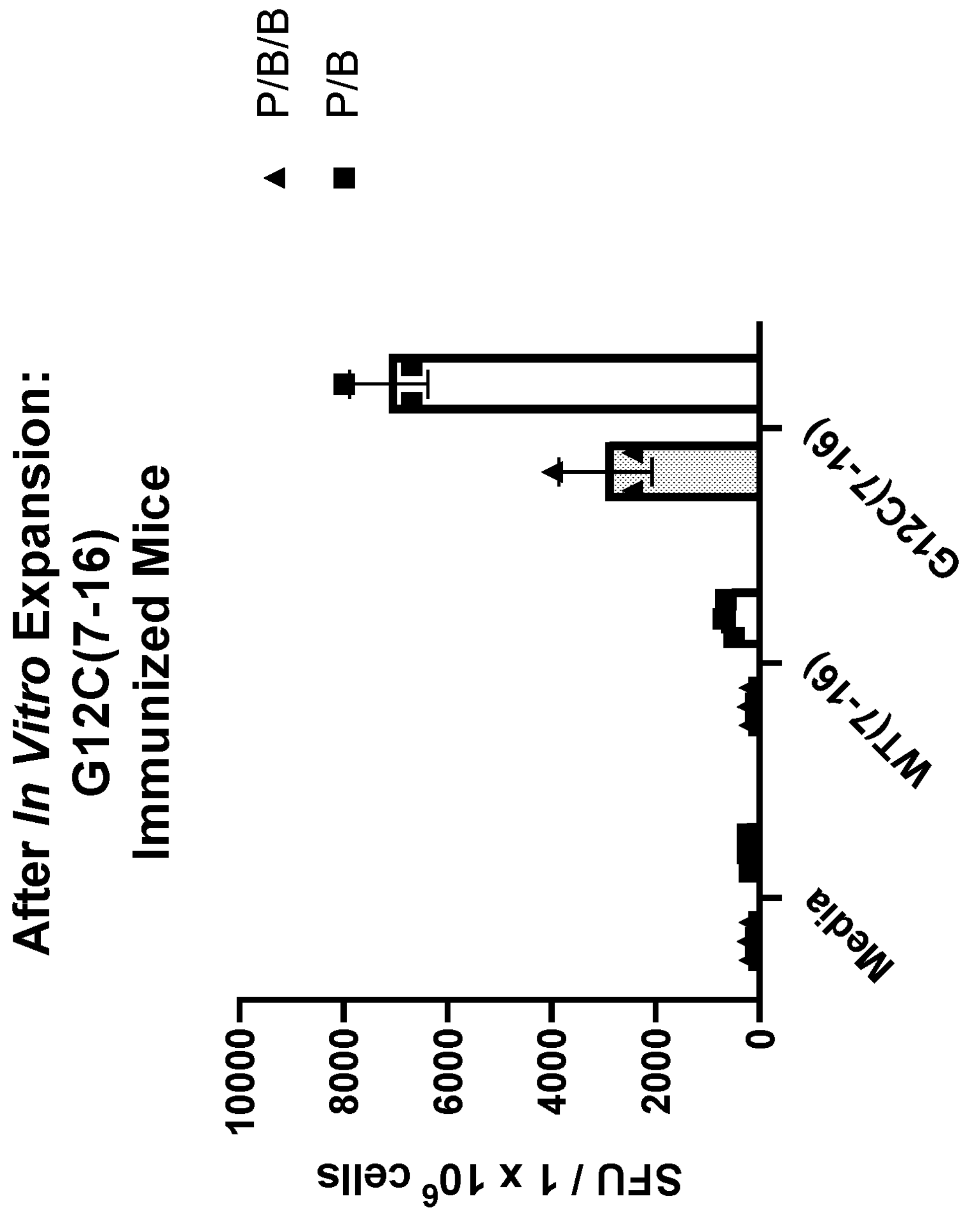
FIG. 9B is a graph showing increased number of IFN-γ expressing cells after 6-days of co-culture with mutant K-Ras G12C$^{7-16}$ peptide and immune cells extracted from HLA-A*11$^{+}$ transgenic mice vaccinated with an emulsion of mutated K-Ras G12C$^{7-16}$.

As shown in FIG. 9A, immune cells extracted from HLA-A*11$^+$ transgenic mice vaccinated with an emulsion of K-Ras G12C$^{7-16}$ showed significantly increased numbers of IFN-γ expressing responder cells upon co-culture with K-Ras G12C$^{7-16}$ peptide. Additionally, as shown in FIG. 9B, immune cells from HLA-A*11$^+$ transgenic mice vaccinated with an emulsion of K-Ras G12C$^{7}$-showed significantly increased numbers of IFN-γ expressing responder cells upon 6 days of co-culture with K-Ras G12C$^{7-16}$ peptide. The results demonstrate that G12C$^{7-16}$ responsive cells can be generated in HLA-A*11 transgenic mice and can be expanded in vitro when stimulated with G12C$^{7-16}$ peptide.

Example 10

In order to determine if immune cells of a specific HLA haplotype SQZ-loaded with a mutant K-Ras antigen can induce an antigen-specific T cell response, human donor HLA-A*11$^+$ PBMCs were SQZ-loaded with K-Ras G12D synthetic long peptides and the ability to stimulate G12D-specific T responder cells were measured using an IFN-γ ELISPOT assay. The effects of PBMCs SQZ-loaded with K-Ras G12D-SLPs were compared to that of the fluid-phase solution from the PBMCs SQZ-loaded with K-Ras G12D-SLP, as well as that of PBMCs incubated with the same K-Ras-G12D SLPs (Endo).

Methods

Human PBMCs from HLA-A*11$^+$ donor were prepared at a density of 10×10$^6$/mL and combined with 100 μM of the respective synthetic long peptide (K-Ras-G12D$^{1-16}$, K-Ras-G12D$^{2-29}$ or HPV-E7.6). For each PBMC sample, half of the PBMCs were SQZ processed at room temperature through a constriction of 4.5 μm width, 10 μm length and 70 μm depth at 60 psi in RPMI medium (SQZ-G12D), whereas the rest of the PBMCs were incubated in room temperature as negative control (Endo-G12D). Following SQZ-processing, the SQZ-loaded PMBCs were centrifuged, and the supernatant was discarded. The cells were subsequently washed once in R10 medium (RPMI+10% FCS+1% Pen/Strep), then washed twice in CTL medium (supplemented with 1% glutamine), before resuspension in CTL medium (supplemented with 1% glutamine). Following the washes, the resulting cell suspension was centrifuged once more, and the resulting supernatant was collected to serve as fluid phase solution (FF-G12D). The SQZ-processed PBMCs were then resuspended in fresh CTL medium (supplemented with 1% glutamine).

2×10$^5$ of either the SQZ-loaded PBMCs (SQZ-G12D) or SLP-incubated PBMCs (Endo-G12D), or an equal volume of the fluid phase solution (FF-G12D) were then placed in co-culture with 5×10$^4$ K-Ras G12D responder T cells (generated in transgenic mice) in an IFN-γ ELISPOT plate. As a positive control, 10 μM K-Ras G12D$^{7-16}$ peptide containing the minimal epitope was added directly to untreated PBMCs and responder cells in the ELISPOT plate (spike). 10 μM wild type K-Ras$^{7-16}$ peptide was added to PBMCs and responder as another positive control (spike). The plate was incubated overnight at 37° C. and then developed/quantified according to manufacturer's instructions.

Results

Figure 10:
FIG. 10 is a graph showing increased amount of IFN-γ expressing K-Ras-G12D responder T cells upon co-culture with PBMCs loaded with K-Ras-G12D$^{1-16}$ or with mutated K-Ras-G12D$^{2-29}$.

As shown in FIG. 10, HLA-A*11$^+$ human PBMCs SQZ-loaded with K-Ras-G12D$^{1-16}$ or K-Ras-G12D$^{2-29}$ SLP (SQZ-G12D) led to significant increases in IFN-γ expressing K-Ras G12D responder T cells upon co-culture, comparable to that induced by K-Ras G12D$^{7-16}$ peptide spike. In contrast, PBMCs incubated with K-Ras-G12D$^{1-16}$ or K-Ras-G12D$^{2-29}$ SLP (Endo-G12D) did not result in increase in IFN-γ expressing responder T cells upon co-culture. In addition, fluid phase solutions from the PBMCs SQZ-loaded with the K-Ras G12D SLPs (FF-G12D) also did not result in IFN-γ expressing responder T cells upon co-culture. These results demonstrate HLA-A*11$^+$ human PBMCs SQZ-loaded with a mutant K-Ras antigen can induce antigen-specific T cell response that is mutation specific, and the immune activation is facilitated by the antigen-comprising PBMCs but not the surrounding fluid phase medium.

SEQUENCE LISTING

| SEQ ID NO | Sequence | Description |
|---|---|---|
| 1 | MTEYKLVVVGADGVGK | G12D(1-16) |
| 2 | TEYKLVVVGADGVGKSAL | G12D(2-19) |
| 3 | TEYKLVVVGADGVGKSALTIQ | G12D(2-22) |
| 4 | TEYKLVVVGADGVGKSALTIQLIQNHFV | G12D(2-29) |
| 5 | MTEYKLVVVGAVGVGK | G12V(1-16) |
| 6 | TEYKLVVVGAVGVGKSAL | G12V(2-19) |
| 7 | EYKLVVVGAVGVGKS | G12V(3-17) |
| 8 | EYKLVVVGAVGVGKSALTIQLIQNHFVDEYD PTIEDSYRK | G12V(3-42) |
| 9 | VVVGADGVGK | 7-16 G12D |
| 10 | VVVGAVGVGK | 7-16 G12V |

-continued

| SEQ ID NO | Sequence | Des-cription |
|---|---|---|
| 11 | VVVGACGVGK | 7-16 G12C |
| 12 | VVGADGVGK | 8-16 G12D |
| 13 | VVGAVGVGK | 8-16 G12V |

-continued

| SEQ ID NO | Sequence | Des-cription |
|---|---|---|
| 14 | KLVVVGADGV | 5-14 G12D |
| 15 | GADGVGKSAL | 10-19 G12D |

What is claimed is:

1. A composition comprising nucleated cells, wherein the nucleated cells comprise an exogenous mutated Ras antigen or an exogenous nucleic acid encoding the mutated Ras antigen intracellularly, wherein the mutated Ras antigen comprises a G12D mutation, a G12V mutation, a G12C mutation or a G13D mutation, and wherein the mutated Ras antigen is one or more of a $G12D^{1-16}$ a $G12D^{2-19}$ a $G12D^{2-22}$, a $G12D^{2-29}$, a $G12V^{1-16}$, a $G12V^{2-19}$, a $G12V^{3-17}$, or a $G12V^{3-42}$ antigen.

2. The composition of claim 1, wherein the exogenous mutated Ras antigen or the exogenous nucleic acid encoding the mutated Ras antigen having entered input nucleated cells through perturbations of the input nucleated cells large enough for the mutated Ras antigen or the nucleic acid encoding the mutated Ras antigen to pass through the perturbations.

3. The composition of claim 2, wherein a cell suspension comprising the input nucleated cells are passed through multiple constrictions arranged in series and/or in parallel.

4. The composition of claim 1, wherein the nucleated cells are immune cells.

5. The composition of claim 1, wherein the nucleated cells are a plurality of peripheral blood mononuclear cells (PBMCs) comprising two or more of T cell, B cell, NK cell, monocytes, dendritic cells or NK-T cells.

6. The composition of claim 1, wherein the nucleated cells are one or more of T cells, B cells, NK cells, monocytes, dendritic cells and/or NK-T cells.

7. The composition of claim 1, wherein the mutated Ras antigen or the nucleic acid encoding the Ras antigen is a mutated K-Ras antigen, a mutated H-Ras antigen, or a mutated N-Ras antigen.

8. The composition of claim 1, further comprising an adjuvant.

9. The composition of claim 8, wherein the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist.

10. A method for producing a composition of nucleated cells comprising an exogenous mutated Ras antigen or an exogenous nucleic acid encoding the mutated Ras antigen intracellularly, wherein the mutated Ras antigen comprises a G12D mutation, a G12V mutation, a G12C mutation or a G13D mutation, and wherein the mutated Ras antigen is one or more of a $G12D^{1-16}$, a $G12D^{2-19}$, a $G12D^{2-22}$, a $G12D^{2-29}$ a $G12V^{1-16}$, a $G12V^{2-19}$, a $G12V^{3-17}$, or a $G12V^{3-42}$ antigen; the method comprising introducing the mutated Ras antigen or the nucleic acid encoding the mutated Ras antigen to the nucleated cell intracellularly.

11. The method of claim 10, wherein introducing the mutated Ras antigen to the nucleated cell intracellularly comprises passing a cell suspension comprising input nucleated cells through a cell-deforming constriction, wherein a diameter of the constriction is a function of a diameter of the input nucleated cells in the suspension, thereby causing perturbations of the input nucleate cells large enough for the mutated Ras antigen or the nucleic acid encoding the mutated Ras antigen to pass through to form a perturbed input nucleated cells; and incubating the perturbed input nucleated cells with the mutated Ras antigen or the nucleic acid encoding the mutated Ras antigen for a sufficient time to allow the mutated Ras antigen or the nucleic acid encoding the mutated Ras antigen to enter the perturbed input nucleated cells; thereby generating nucleated cells comprising the mutated Ras antigen or the nucleic acid encoding the mutated Ras antigen.

12. The method of claim 11, wherein the width of the constriction is about 10% to about 99% of the mean diameter of the input nucleated cells.

13. The method of claim 11, wherein the width of the constriction is about 3.5 μm to about 4.2 μm or about 3.5 μm to about 4.8 μm or about 3.5 μm to about 6 μm or about 4.2 μm to about 4.8 μm or about 4.2 μm to about 6 μm.

14. The method of claim 11, wherein the cell suspension comprising the plurality of input nucleated cells are passed through multiple constrictions arranged in series and/or in parallel.

15. The method of claim 10, further comprising conditioning the nucleated cells with an adjuvant to form conditioned cells.

16. The method of claim 15, wherein the nucleated cells are conditioned before or after introducing the mutated Ras antigen into the nucleated cells.

17. The composition of claim 1, wherein the mutated Ras antigen is a tumor antigen or tumor-associated antigen.

18. The method of claim 10, wherein the mutated Ras antigen is a tumor antigen or a tumor-associated antigen.

* * * * *

SEQUENCE LISTING

<160> NUMBER OF SEQ ID NOS: 18

<210> SEQ ID NO 1
<211> LENGTH: 16
<212> TYPE: PRT
<213> ORGANISM: Artificial Sequence
<220> FEATURE:
<223> OTHER INFORMATION: Synthetic Construct

<400> SEQUENCE: 1

```
Met Thr Glu Tyr Lys Leu Val Val Val Gly Ala Asp Gly Val Gly Lys
1               5                   10                  15
```

<210> SEQ ID NO 2
<211> LENGTH: 18
<212> TYPE: PRT
<213> ORGANISM: Artificial Sequence
<220> FEATURE:
<223> OTHER INFORMATION: Synthetic Construct

<400> SEQUENCE: 2

```
Thr Glu Tyr Lys Leu Val Val Val Gly Ala Asp Gly Val Gly Lys Ser
1               5                   10                  15

Ala Leu
```

<210> SEQ ID NO 3
<211> LENGTH: 21
<212> TYPE: PRT
<213> ORGANISM: Artificial Sequence
<220> FEATURE:
<223> OTHER INFORMATION: Synthetic Construct

<400> SEQUENCE: 3

```
Thr Glu Tyr Lys Leu Val Val Val Gly Ala Asp Gly Val Gly Lys Ser
1               5                   10                  15

Ala Leu Thr Ile Gln
            20
```

<210> SEQ ID NO 4
<211> LENGTH: 28
<212> TYPE: PRT
<213> ORGANISM: Artificial Sequence
<220> FEATURE:
<223> OTHER INFORMATION: Synthetic Construct

<400> SEQUENCE: 4

```
Thr Glu Tyr Lys Leu Val Val Val Gly Ala Asp Gly Val Gly Lys Ser
1               5                   10                  15

Ala Leu Thr Ile Gln Leu Ile Gln Asn His Phe Val
            20                  25
```

<210> SEQ ID NO 5
<211> LENGTH: 16

<212> TYPE: PRT
<213> ORGANISM: Artificial Sequence
<220> FEATURE:
<223> OTHER INFORMATION: Synthetic Construct

<400> SEQUENCE: 5

```
Met Thr Glu Tyr Lys Leu Val Val Val Gly Ala Val Gly Val Gly Lys
1               5                   10                  15
```

<210> SEQ ID NO 6
<211> LENGTH: 18
<212> TYPE: PRT
<213> ORGANISM: Artificial Sequence
<220> FEATURE:
<223> OTHER INFORMATION: Synthetic Construct

<400> SEQUENCE: 6

```
Thr Glu Tyr Lys Leu Val Val Val Gly Ala Val Gly Val Gly Lys Ser
1               5                   10                  15

Ala Leu
```

<210> SEQ ID NO 7
<211> LENGTH: 15
<212> TYPE: PRT
<213> ORGANISM: Artificial Sequence
<220> FEATURE:
<223> OTHER INFORMATION: Synthetic Construct

<400> SEQUENCE: 7

```
Glu Tyr Lys Leu Val Val Val Gly Ala Val Gly Val Gly Lys Ser
1               5                   10                  15
```

<210> SEQ ID NO 8
<211> LENGTH: 40
<212> TYPE: PRT
<213> ORGANISM: Artificial Sequence
<220> FEATURE:
<223> OTHER INFORMATION: Synthetic Construct

<400> SEQUENCE: 8

```
Glu Tyr Lys Leu Val Val Val Gly Ala Val Gly Val Gly Lys Ser Ala
1               5                   10                  15

Leu Thr Ile Gln Leu Ile Gln Asn His Phe Val Asp Glu Tyr Asp Pro
            20                  25                  30

Thr Ile Glu Asp Ser Tyr Arg Lys
        35                  40
```

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

```
Val Val Val Gly Ala Asp Gly Val Gly Lys
1               5                   10
```

<210> SEQ ID NO 10
<211> LENGTH: 10
<212> TYPE: PRT
<213> ORGANISM: Artificial Sequence
<220> FEATURE:
<223> OTHER INFORMATION: Synthetic Construct

<400> SEQUENCE: 10

Val Val Val Gly Ala Val Gly Val Gly Lys
1 5 10

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Val Val Val Gly Ala Cys Gly Val Gly Lys
1 5 10

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Val Val Gly Ala Asp Gly Val Gly Lys
1 5

<210> SEQ ID NO 13
<211> LENGTH: 9
<212> TYPE: PRT
<213> ORGANISM: Artificial Sequence
<220> FEATURE:
<223> OTHER INFORMATION: Synthetic Construct

<400> SEQUENCE: 13

Val Val Gly Ala Val Gly Val Gly Lys
1 5

<210> SEQ ID NO 14
<211> LENGTH: 10
<212> TYPE: PRT
<213> ORGANISM: Artificial Sequence
<220> FEATURE:
<223> OTHER INFORMATION: Synthetic Construct

<400> SEQUENCE: 14

Lys Leu Val Val Val Gly Ala Asp Gly Val
1 5 10

<210> SEQ ID NO 15
<211> LENGTH: 10
<212> TYPE: PRT
<213> ORGANISM: Artificial Sequence
<220> FEATURE:
<223> OTHER INFORMATION: Synthetic Construct

<400> SEQUENCE: 15

Gly Ala Asp Gly Val Gly Lys Ser Ala Leu
1 5 10

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16

-continued

```
tccatgacgt tcctgacgtt                                          20


<210> SEQ ID NO 17
<211> LENGTH: 24
<212> TYPE: DNA
<213> ORGANISM: Artificial Sequence
<220> FEATURE:
<223> OTHER INFORMATION: Synthetic Construct

<400> SEQUENCE: 17

tcgtcgtttt gtcgttttgt cgtt                                     24


<210> SEQ ID NO 18
<211> LENGTH: 13
<212> TYPE: PRT
<213> ORGANISM: Artificial Sequence
<220> FEATURE:
<223> OTHER INFORMATION: Synthetic Construct

<400> SEQUENCE: 18

Thr Pro Pro Ala Tyr Arg Pro Pro Asn Ala Pro Ile Leu
1               5                   10
```